(12) United States Patent
Oscarson et al.

(10) Patent No.: US 8,062,641 B2
(45) Date of Patent: Nov. 22, 2011

(54) IMMUNOGENS FOR MENINGITIDIS-A VACCINES

(75) Inventors: Stefan Oscarson, Stockholm (SE); Peter Teodorovic, Stockholm (SE); Paolo Costantino, Siena (IT)

(73) Assignees: Novartis AG, Basel (CH); Stefan Oscarson, Stockholm (SE); Peter Teodorovic, Stockholm (SE)

( * ) Notice: Subject to any disclaimer, the term of this patent is extended or adjusted under 35 U.S.C. 154(b) by 741 days.

(21) Appl. No.: 11/913,765

(22) PCT Filed: May 8, 2006

(86) PCT No.: PCT/IB2006/001703
§ 371 (c)(1),
(2), (4) Date: Jul. 29, 2008

(87) PCT Pub. No.: WO2006/120576
PCT Pub. Date: Nov. 16, 2006

(65) Prior Publication Data
US 2009/0304734 A1    Dec. 10, 2009

Related U.S. Application Data

(60) Provisional application No. 60/678,289, filed on May 6, 2005.

(51) Int. Cl.
*A61K 39/00* (2006.01)
*A61K 39/02* (2006.01)
*A61K 39/385* (2006.01)

(52) U.S. Cl. ............... 424/184.1; 424/193.1; 424/194.1; 424/197.11; 424/234.1

(58) Field of Classification Search ............ None
See application file for complete search history.

(56) References Cited

U.S. PATENT DOCUMENTS
4,356,170 A    10/1982 Jennings et al.
6,114,309 A *  9/2000 Allanson et al. ............ 514/25

FOREIGN PATENT DOCUMENTS
WO    WO-2004/019992 A1    3/2004
WO    WO-2004/067030      8/2004

OTHER PUBLICATIONS

New Zealand Examination Report mailed Jun. 28, 2010, for NZ Application No. 563940 filed May 8, 2006, 2 pages.
Berkin et al., Chemistry (2002) 8(19):4424-4433.
Bundle et al., J. Biol. Chem. (1974) 249:2275-2281.
Casero et al., Journal of Organic Chemistry (1996) 61(10):3428-3432.
International Search Report for PCT/IB2006/001703, mailed on May 8, 2007, 5 pages.
Plotkin and Orenstein, Vaccines, 4th ed., Saunders (2004), pp. 959-987.
Popelova et al., Carbohydrate Research (2005) 340:161-166.
Slattegard et al., Organic and Biomolecular Chemistry (2005) 3(20):3782-3787.
Torres-Sanchez et al., Synlett (2005) 7:1147-1151.
Written Opinion of the International Searching Authority for PCT/IB2006/001703, mailed on May 8, 2007, 11 pages.

* cited by examiner

*Primary Examiner* — Albert Navarro
(74) *Attorney, Agent, or Firm* — Morrison & Foerster LLP

(57) ABSTRACT

An oligosaccharide useful for a Meningitidis A vaccine contains a first mannose unit having a spacer in the alpha configuration at C-1, which spacer is capable of conjugating to a protein, and which is connected to a second mannose unit through a 1,6-linkage which connects C-6 of the first unit to C-1 of the second unit, wherein the 1,6-linkage comprises a phosphonate. Related methods of making such compounds, analogous compounds, or intermediates thereof are also disclosed.

43 Claims, 4 Drawing Sheets

The Natural Capsular Polysaccharide (CPS) of *N. meningitidis.*

R represents either H or Ac; approximately 70-80% of the natural capsular polysaccharide of *N. meningitidis* is acetylated at this position The Alpha and Beta Anomers of 2-Deoxy-2-Aza Substituted Mannose Units Alpha Anomer Beta Anomer The Elongation Sequence for Making Oligosaccharides of the Invention

IMMUNOGENS FOR MENINGITIDIS-A VACCINES

RELATED APPLICATION

This application claims benefit of U.S. application Ser. No. 60/678,289 filed May 6, 2005, which is incorporated herein by reference in its entirety.

TECHNICAL FIELD

The invention relates to a compound useful for a Meningitidis A vaccine. More particularly, the compound is an oligosaccharide that comprises a stabilized phosphorous-containing linkage, preferably a phosphonate linkage. The compound more preferably contains mannose units and may also contain a spacer in the alpha configuration at C-1 of the mannose unit. The invention also includes methods of making the oligosaccharide and improved methods of making mannose-containing compounds and intermediates.

BACKGROUND ART

Meningitis is an infection of the meninges, the thin lining that surrounds the brain and spinal cord. Several kinds of bacteria can cause meningitis, and *N. meningitidis* is one of the most important. Others are *Streptococcus pneumoniae* and *Haemophilus influenzae* type b. There are several subgroups of *N. meningitidis*, which are differentiated by the structure of the capsular polysaccharide that surrounds the bacterium.

Meningitis is caused by both viruses and bacteria. The two major types of bacteria causing meningitis are *Haemophilus influenzae* and *Neisseria meningitidis*. In the case of *H. influenzae* only one serotype, type b, is important, whereas with *N. meningitidis* twelve serogroups have been identified, of which groups A, B, C, and W135 are known to cause epidemics. The various serotypes have different geographical prevalence, e.g., type B and C are dominant in Europe and North America and Type A in Africa and South America. The serotyping is based on the structure and antigenicity of the capsular polysaccharide (CPS) surrounding the bacteria, and the CPS can also be used as a vaccine against the bacteria. Especially efficient vaccines (glycoconjugate vaccines) can be made by attaching the saccharide to a carrier protein. See Plotkin, S. A., and Orenstein, W. A., *Vaccines*, 4$^{th}$ ed., Saunders, pages 959-987 (2004), which is incorporated herein by reference. These glycoconjugates induce a T-cell dependent immune response with memory and effect also in small children, while the non-conjugated CPS generally fails to provide either a memory effect in adults or any substantial immunogenic effect in infants. The development of type A vaccines has been considered especially difficult, due to the inherent instability of the anomeric phosphate diester linkages that are part of the CPS. The repeating unit of type A is a monosaccharide, 2-acetamido-2-deoxy-α-D-mannopyranose linked 1→6 via a phosphodiester bridge (FIG. 1). In the native polysaccharide the 3-OH is acetylated to an extent of about 80%. The immunological importance of this acetylation has not been completely investigated, but there are indications that it is not of major significance.

*Neisseria meningitidis* serogroup A causes epidemic outbreaks of meningitis, mainly in parts of Africa south of the Sahara in the so-called meningitis belt. In the meningitis belt the estimated incidence for the period 1970-1992 was about 800,000 cases. See Plotkin, S. A., and Orenstein, W. A., *Vaccines*, 4$^{th}$ ed., Saunders, pages 959-987 (2004). The epidemic outbreaks of meningitis are devastating for the region, so an effective vaccine is urgently needed. The hope is of course, that the development of a good vaccine, in combination with efforts similar to the ones against smallpox performed by WHO in the 1960's and 70's could likewise eliminate meningitis caused by *N. meningitides* serotype A. Vaccinations are a much more cost effective way of controlling a disease than treatment with antibiotics and other therapies, and cost is especially important in the developing world.

Vaccines prepared from the polysaccharide coating on the bacterium, its capsular polysaccharide, are effective in adults. Exposure to this polysaccharide causes adults to develop an immunogenic response that protects against meningitis caused by *N. meningitidis*. A big limitation with such vaccines, though, is that the immune system of children under around two years of age does not respond to most polysaccharide antigens. Unfortunately, this is the age group at greatest risk for bacterial meningitis. Thus, the polysaccharide vaccines are of no use in young children. Furthermore, even in older children and adults, these vaccines induce only short-term immunity. Protection decreases rapidly and is generally gone by around two years after vaccination.

Polysaccharides like the *N. meningitidis* CPS are T-cell independent antigens, which means that they can give an immune response without the involvement of T-cells (thymus-derived cells). This response lacks several important properties that characterize the T-cell dependent immune response, such as immunological memory, class-switch from IgM to IgG, and affinity maturation. If the polysaccharide part is connected to a carrier protein, however, it triggers a cellular immune response that creates memory effect, and also gives protection in young children. Such polysaccharides linked to carrier proteins are often referred to as glycoconjugates, and are especially valuable as vaccines.

Glycoconjugate vaccines are so called because their production involves the conjugation of a polysaccharide antigen or other glycosidic antigen to a carrier protein. The saccharide moiety in glycoconjugate vaccines is usually a functionalized bacterial CPS, but it can also be synthetic. Synthetic carbohydrate structures have a number of potential advantages over those based on carbohydrates from natural sources. Naturally derived carbohydrates are heterogeneous mixtures and may include small amounts of natural impurities and contaminants. In contrast, synthetic carbohydrates can be produced as homogeneous single compounds in a controlled manner, with little or no batch-to-batch variability. Another advantage of synthetic structures is that they can be made to include functional groups for derivitization or modifications of the carbohydrate moiety that are difficult or impossible to perform on the native material. The carrier protein is an important factor in the modulation of the immunogenicity. Various carriers have been used for conjugation, and the best results have been achieved using detoxified versions of strongly immunogenic proteins like diphtheria and tetanus toxins, which have been approved for use in humans. See U.S. Pat. No. 4,354,170. It has also been shown that the immune system reacts more effectively when patients have already been immunized with the particular carrier protein.

A glycoconjugate vaccine is usually made by conjugating the native capsular polysaccharide structure of the bacterium to a suitable carrier protein. However there have been problems with that approach due to the properties of the polysaccharide that encapsulates *N. meningitidis*. Its phosphodiester linkage can degrade under the conditions necessary for attachment of the polysaccharide to proteins, and even after preparation, glycoconjugates of the native CPS tend to degrade during storage.

Phosphodiesters are normally quite stabile, but in the capsular polysaccharide of N. meningitidis, the phosphodiester is linked to the anomeric center of a carbohydrate residue. Thus one oxygen of the phosphodiester is also part of an acetal linkage, which makes it susceptible to hydrolytic cleavage catalyzed by electrophiles such as acid or metal ions. Cleavage of this bond breaks the polysaccharide down into smaller pieces. Unfortunately, during the manipulations required to form a glycoconjugate, or even in a vaccine formulation, the CPS of N. meningitidis A is subject to such degradation, rendering it difficult to make and store effective vaccines comprising this particular CPS.

One way of making the phosphodiester linkage more stable is to eliminate the oxygen between the phosphorus and the anomeric oxygen, so that portion of the linkage is no longer susceptible to cleavage by electrophilic hydrolysis. The exocyclic oxygen at the anomeric center can be replaced with an isosteric carbon atom, ($CH_2$), transforming the phosphodiester into its C-phosphonate analogue. This should produce a stabilized version of the antigenic polysaccharide. One investigation directed toward this approach has recently been published. Torres-Sanchez, M. I., et al., *Synlett* (2005) 7:1147-1151. However, the authors did not assess the activity of their compounds or disclose an oligomer of more than two mannose units. Furthermore, their synthesis approach provided only the beta anomer at the position where the oligosaccharide is intended to link to a protein, while the native CPS of N. meningitidis only contains alpha-linkages. Thus there remains a need for alpha-linked glycoconjugates having stabilized linkages between the mannose units and for methods to synthesize them.

Another approach is to stabilize the phosphodiester linkages using inductive effects from nearby substituents to reduce the electron density at the anomeric oxygens; this, too, should slow the anticipated electrophilic degradation mechanisms. The electron-attracting property of the substituents can be maintained while an oligosaccharide is constructed, and perhaps also while it is conjugated to a protein, then removed once the molecule no longer needs to be exposed to destructive conditions.

The present invention includes each of these approaches as well as combinations thereof. One aspect of the invention thus provides an efficient synthesis of a C-phosphonate analogue of an oligomeric form of the repeating unit of the *N. meningitidis* type A capsular polysaccharide, needed for vaccine development. See Bundle, D. R., et al., *J. Biol. Chem.* (1974) 249:2275-2281. The invention particularly provides methods for introducing a spacer moiety through which the oligosaccharides of the invention can be conjugated to a protein to make a glycoconjugate vaccine, and it orients the spacer moiety in the alpha anomeric configuration. FIG. 2 illustrates a compound having the desired alpha configuration at this center and one having the beta configuration. Since the natural CPS of the target organism is a fully alpha-linked oligomer of mannose units, it is especially desirable to provide the same alpha-linked configuration in a synthetic immunogen. Even if all of the linkages between mannose units in a synthetic oligomer portion of a glycoconjugate are in the alpha configuration, the configuration at the center through which the oligosaccharide is linked to the protein can be particularly influential on the immunogenic effects when the oligosaccharide portion of the glycoconjugate contains fewer than about 10 mannose units.

The present invention thus provides such compounds and methods for the preparation of these compounds. The crucial coupling step is often performed using a C-phosphonate mono-ester and Mitsunobu conditions. While it may be impractical to prepare polysaccharides rivaling the natural CPS in size, that is not necessary: even oligosaccharides only a few mannose-units in length can elicit an immune response. And synthetic oligosaccharides offer the advantages of selective linkage mechanisms and increased stability in vivo, each of which should enhance their immunogenic effectiveness in vivo.

Another aspect of the invention provides methods to stabilize the mannose units so that a phosphodiester linkage, the linkage present in the native capsular polysaccharide, can be used. It includes compounds and methods that provide stabilization to facilitate preparation of the protein conjugates of the oligosaccharides. The stabilization is provided by an electron-attracting group, an azide, at C-2 of at least one of the mannose units in a polysaccharide, which increases the polysaccharide's stability so that it can be conjugated to a protein. After conjugation, the stabilization is less important, and at that point the azide is typically reduced to an amine and acylated, which provides the 2-acetylamino group that is part of the recurring mannose unit in the *N. meningitidis* A capsular polysaccharide.

Where appropriate, it is also possible to mix the two stabilization methods; thus an oligosaccharide of the invention may include azide-containing mannose units that are linked by a phosphodiester at the adjacent anomeric center in combination with phosphonate-linked mannose units. This combination may provide additional stabilization, depending on the orientation of the phosphonate; or it may provide synthetic advantages such as increased yields and it may avoid complications that the acetylamine substituent can cause.

In other aspects, the invention provides methods to synthesize key precursors for these compounds, pharmaceutical compositions containing them, and methods to use them to manufacture a medicament. The compounds, compositions and medicaments may be administered to a subject to induce an immunogenic response in the subject, which is typically a human.

DISCLOSURE OF THE INVENTION

The invention provides immunogenic compounds that comprise a polysaccharide or oligosaccharide and methods to make these compounds, as well as methods to use them as vaccines to provide protection against infection by the *Neisseria meningitidis* A bacterium. The methods allow the preparation of oligosaccharides comprising at least two mannose units that are connected through a 1,6-linkage. This linkage is often a 1,6-alpha linkage, and the mannose units are sometimes N-substituted mannose groups such as those having 2-NHAc or 2-$N_3$ on one or more of the mannose units. The linkage may take various forms, but often it comprises a phosphonate or a phosphate. In some embodiments, the oligosaccharide comprises at least three mannose units linked in sequence, each of which is typically N-substituted. While the compounds may contain any number of mannose units, in preferred embodiments the oligosaccharide portion of the molecule has a molecular weight under 2000. Thus preferably the compounds of the invention include about two to ten mannose units linked in series, preferably about three to seven.

The compounds of the invention are adapted to be conjugated to a protein, since the glycoconjugate forms are much more effective immunogens for vaccination purposes: they elicit immunogenic responses in infants, and they elicit cellular responses that provide a memory effect to prolong the effectiveness of the vaccination. The compounds thus comprise a spacer moiety that is attached to the first mannose unit in a chain of mannose units. The spacer unit is specifically designed to provide a means for conjugation of the oligosaccharide to a protein, or to provide a means for capping the terminal saccharide unit, such that it is unreactive, for example to further chain elongation/modification reactions. Typically, this spacer moiety possesses an amine, carboxylate, or hydroxyl group for coupling to a complementary group on a protein carrier, but other groups known in the art to provide a way to conjugate an oligosaccharide to a protein are also included. Alternatively, the spacer moiety possesses a protecting or capping group, such as an alkyl, aryl, or acyl group, as well as others well know in the art and/or disclosed herein. In compounds of the invention, this spacer moiety is in the alpha configuration so that it most closely resembles the linkages in the natural CPS of *N. meningitidis* and does not interfere with the desired immunogenic effect, even in short oligosaccharides of the invention.

The compounds of the invention often comprise the structure shown in formula (1):

(1)

wherein each Az represents an aza substituent;

each $R^3$ and $R^4$ independently represents H or a protecting group;

$R^6$ represents H, a protecting group, or a linker attached to another saccharide unit;

one of W and X is O, and the other of W and X is $CH_2$;

n is 1 or 2;

$Y_n$ is OR when n is 1, and when n is 2, one Y is =O and the other Y is OR, wherein R is H, C1-C6 alkyl, or C6-C12 aryl, or C6-C12 arylalkyl, or R is M, where M is a cation; and Z is OR', SR', $NR'_2$, or halo, where each R' is independently H or an optionally substituted alkyl, acyl, aryl, arylalkyl, heteroalkyl, heteroacyl, heteroaryl, or heteroarylalkyl group;

or Z represents a linker attached to another saccharide unit or a spacer moiety conjugated to a protein.

Often in these compounds, X is O and W is $CH_2$, and Az is often $N_3$, $NH_2$ or NHAc; and often n is 2.

The compounds of the invention are synthesized in part by art-known methods, but a number of novel methods for forming these molecules are also part of the invention. For example, the 1,6-alpha linkage in a compound of formula (1) can be constructed with a Mitsunobu reaction as described herein. Also, the N-substituents such as Az can be inserted as an azide by methods provided herein, and can then be reduced to provide an amine or substituted amine, which is often at position 2 of a mannose unit, as shown in formula (1). Typical methods for reduction of the azide include catalytic hydrogenation and borohydride reduction, typically using catalytic amounts of a nickel salt.

The invention also provides a method to make phosphonate-substituted mannose units for assembling the oligosaccharides described herein. For example, a compound of formula (2), which is available from glucose, can be converted into a precursor for a phosphonate ester useful for forming the phosphonate-comprising 1,6-alpha-linkage shown in formula (1) where W is $CH_2$ and X is O. The method includes cyclizing a compound of formula (2) with an electrophile (2)

to form a compound of formula (3)

(3)

wherein each of $R^2$, $R^3$, $R^4$ and $R^6$ is independently H or a protecting group;

and El represents the residue of electrophile.

The residue of an electrophile, El, is the portion of the electrophilic reagent used to initiate cyclization that remains attached to the carbon. El can then be replaced, either directly or indirectly, by a phosphorus-containing groups such as a phosphonate group by the methods described herein. This provides a glucose derivative rather than an N-substituted mannose unit, i.e., it has the wrong stereochemistry at C-2; thus the invention further provides methods to convert $OR^2$ in formula (2) or formula (3) into an Az group having the proper stereochemistry by displacing an activated form of the oxygen of $OR^2$ with an azide. The method comprises a Mitsunobu reaction, which typically uses a phosphoryl azide as the azide source.

The invention also provides a method to prepare a 2-azido-2-deoxy-D-mannopyranose, which method comprises forming a triflate at position 2 of a 1,3,4,6-tetra-protected glucopyranose derivative; and displacing the triflate with an azide nucleophile. In some embodiments, the 1,3,4,6-tetra-protected glucose derivative is a 1,3,4,6-tetra-O-acyl glucopyranose, which is readily available. See, e.g., Helferich, B., et al., *Ber. Dtsch Chem. Ges.* (1962) 95:2604-2611. 1,3,4,6-Tetra-O-acetyl glucopyranose is sometimes preferred.

The immunogenic activity of compounds and compositions comprising the oligosaccharides described herein is often enhanced by conjugation of the oligosaccharide to a protein. Thus in many embodiments, the invention includes conjugating the oligosaccharide to a protein through a spacer moiety attached to the C-1 carbon of the first mannose unit in the chain. In some embodiments, the protein is one chosen for its ability to enhance the immunogenic response in a human, and the detoxified toxoids from diphtheria and tetanus are often used. Thus the compounds of the invention often include a spacer moiety, which may be Z in formula (1) or may be attached to any of the available hydroxyl groups or N-substituents on the mannose units, and which facilitates attachment to a protein. Typically, the connection to the protein is through Z, thus Z is often a spacer moiety that is capable of being conjugated to a protein. In many of the compounds of the invention, Z is in a protected form. Suitable protecting groups depend on the exact nature of Z, and selection and usage of such protecting groups is within the ordinary skill in the art. Examples of such protecting groups and details of their usage are available in, for example, Greene, T. W., and Wuts, P. G. M., *Protective Groups in Organic Synthesis*, 2d ed. (1991). Similarly, the invention provides methods to use Z to connect the oligosaccharide to a protein to produce an immunogenic composition.

The invention also provides vaccine compositions comprising an oligosaccharide of the invention, which are useful for eliciting an immunogenic response in a mammal. Typically the mammal is a human subject since *N. meningitidis* is believed to be pathogenic only in humans, but eliciting an immune response in other mammals is of value, too, and can be used to provide immune components such as antibodies. Thus the invention provides immunogenic compositions and methods to use these to elicit an immunogenic response in a mammal.

MODES OF CARRYING OUT THE INVENTION

Figure 1:
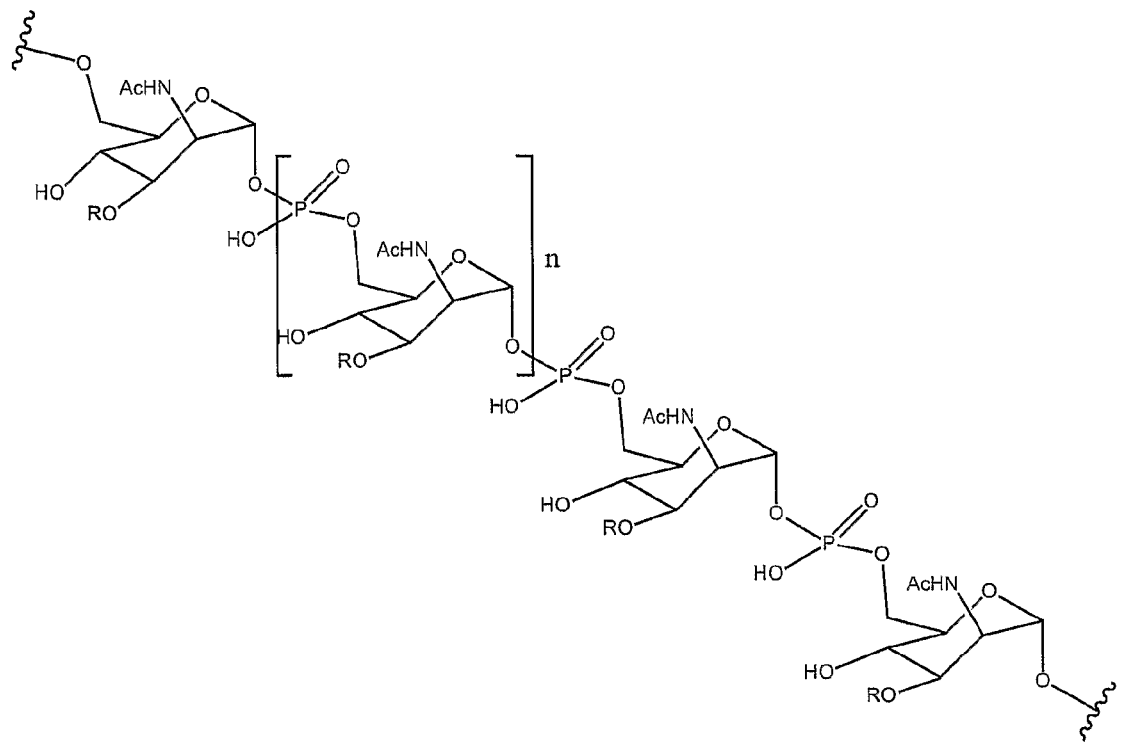
FIG. 1 shows the structure of the capsular polysaccharide of *N. meningitidis* A.
Figure 2:
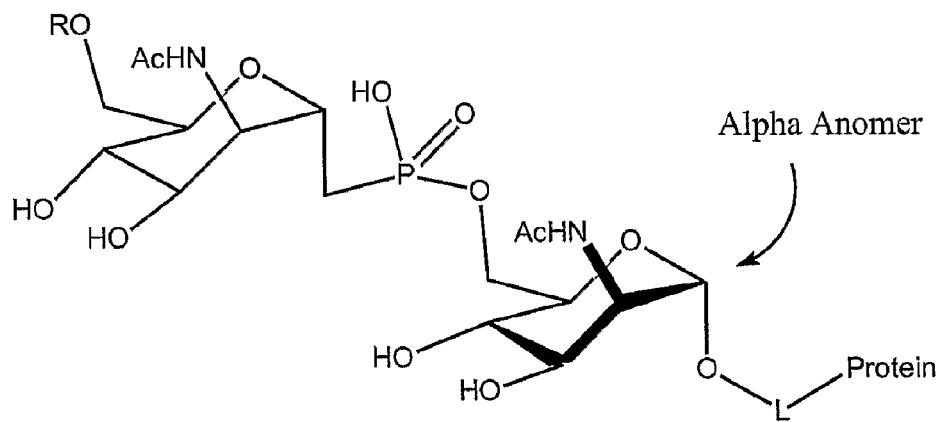
FIG. 2 is an illustration of the alpha and beta anomers at the center through which the oligosaccharide is conjugated to a protein to enhance its immunogenicity.
Figure 2:
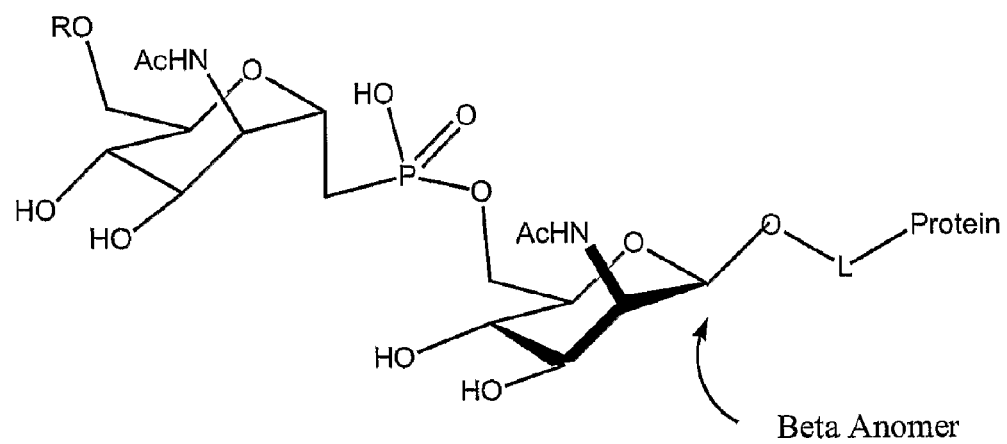

In one aspect, the invention provides an oligosaccharide comprising a first mannose unit and a second mannose unit, wherein the first mannose unit comprises a spacer in the alpha configuration at C-1. This spacer is capable of conjugating to a protein, and the first mannose unit is connected to the second mannose unit through a 1,6-linkage which connects C-6 of the first unit to C-1 of the second mannose unit. The 1,6-linkage comprises a phosphonate in some embodiments. In some embodiments, the 1,6-linkage is in the alpha configuration. In some of these embodiments, the first mannose unit is a 2-deoxy-2-aza substituted mannose derivative, and in some of the embodiments the second mannose unit is a 2-deoxy-2-aza substituted mannose derivative. Certain embodiments have two or three, or more than three of these 2-aza substituted mannose units.

In some of the embodiments of the invention, the 1,6-linkage is of the form [C-1 of second mannose unit]-$CH_2$—P—O—[C-6 of first mannose unit], i.e., the phosphonate carbon is connected to C-1 of the second mannose unit and a phosphonate ester oxygen is bonded to C-6 of the first mannose unit. These mannose units are optionally protected, and in many embodiments one or both of these two mannose units comprises a 2-aza substituent which is selected from $NH_2$, NHAc, and $N_3$. Where these embodiments include a third mannose unit, it is sometimes connected to the second mannose unit by a linkage which comprises phosphorus, and wherein the linkage connects C-6 of the second mannose unit to C-1 of the third mannose unit. This linkage often comprises a phosphonate, which is often lined to the second mannose unit through a phosphonate ester linkage, and to the third mannose unit through a P—C bond of the phosphonate.

In other aspects, the invention provides an oligosaccharide of formula (1):

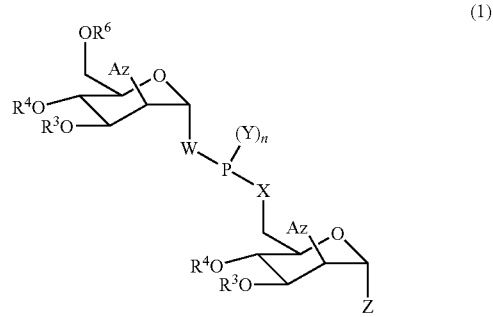

(1)

wherein each Az represents an aza substituent;
each $R^3$ and $R^4$ independently represents H or a protecting group;
$R^6$ represents H, a protecting group, or a linker attached to another saccharide unit;
one of W and X is O, and the other of W and X is $CH_2$;
n is 1 or 2;
$Y_n$ is OR when n is 1, and when n is 2, one Y is =O and the other Y is OR,
wherein R is H, C1-C6 alkyl, or C6-C12 aryl, or C6-C12 arylalkyl, or R is M, where M is a cation; and
Z is OR', SR', or $NR'_2$, where each R' is independently H or an optionally substituted alkyl, acyl, aryl, arylalkyl, heteroalkyl, heteroacyl, heteroaryl, or heteroarylalkyl group;
or Z represents a linker attached to another saccharide unit or a spacer moiety conjugated to a protein.

In some embodiments, compounds that comprise formula (1) are conjugated to a protein through an amide or ester linkage. Often in compounds of formula (1), W is $CH_2$ and X is O, and in many of such embodiments, Az is NHAc and n is 2. Also, in many embodiments of this aspect, R is M and Z comprises —O—$(CH_2)_n$—NH—, wherein n is 2-6. In embodiments of these compounds based on formula (1), each $R^3$ and $R^4$ is independently H or Ac. Often $R^3$ is Ac, and optionally both $R^3$ and $R^4$ are either H or Ac.

In other aspects, the invention provides methods to make an oligosaccharide, which methods comprise linking a first moiety which comprises at least one aza substituted mannose unit through a 1,6-linkage which comprises a phosphonate to a second moiety which comprises at least one aza substituted mannose unit. The first moiety in these embodiments often comprises a spacer moiety, which spacer moiety is linked to C-1 of a mannose unit in the alpha-configuration. In some embodiments of these methods, a Mitsunobu reaction is used to link C-6 of a mannose unit of the first moiety to C-1 of a mannose unit of the second moiety. In many of the embodiments of these methods, the 1,6-linkage is a 1,6-alpha linkage.

In some of these aspects, the linked aza substituted mannose units comprise the formula (1)

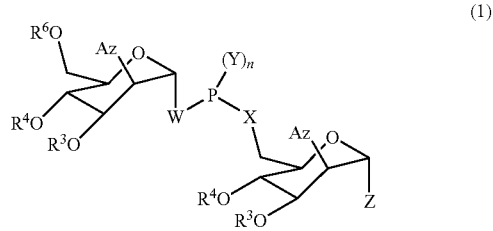

(1)

wherein each Az represents an aza substituent;
each $R^3$ and $R^4$ independently represents H or a protecting group;
$R^6$ represents H, a protecting group, or a linker attached to another saccharide unit;
one of W and X is O, and the other of W and X is $CH_2$;
n is 1 or 2;
$Y_n$ is OR when n is 1, and when n is 2, one Y is =O and the other Y is OR,
wherein R is H, C1-C6 alkyl, or C6-C12 aryl, or C6-C12 arylalkyl, or R is M, where M is a monovalent cation; and
Z represents a moiety capable of being conjugated to a protein, which may be in protected form.

In some embodiments of the method, in the compounds that comprise formula (1), X is $CH_2$ and W is O. In these embodiments, often at least one aza substituent on a mannose unit is an amine or substituted amine that is obtained by reduction of an azide ($N_3$) substituent. In preferred embodiments, the amine or substituted amine is at position 2 on a mannose unit. In some embodiments of these methods, the oligosaccharide comprises a spacer moiety which may be Z in a compound of formula (1), which is at the anomeric center of a mannose unit. This spacer unit may comprise an amine-substituted alkoxy group, which is optionally in protected form. For example, it may be of the formula —O—$(CH_2)_n$—NH—PG, where PG represents H or a protecting group; the protecting group is often an alkoxycarbonyl such as methoxy carbonyl; t-butyloxy carbonyl; or benzyloxycarbonyl. Thus NH—PG is often a carbamate group.

In some embodiments of these methods, the method further comprises linking the second mannose unit to an additional saccharide by forming a bond between the oxygen of $OR^6$ in formula (1) and the additional saccharide. This saccharide may be a mannose unit or comprise a mannose unit, and in many embodiments the additional saccharide is linked to the second mannose unit through a 1,6-alpha linkage. In these embodiments, often $R^6$ is H or Ac and the anomeric center of each mannose unit present is in the alpha configuration to most closely resemble the natural CPS of N. meningitidis.

In other aspects, the invention provides an oligosaccharide of the formula (1'):

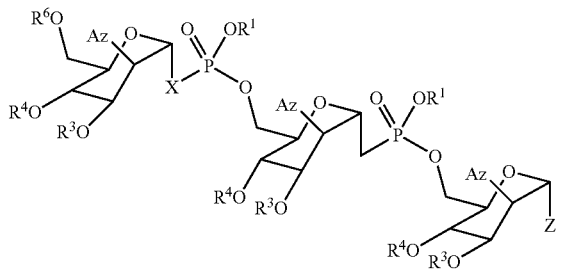

(1')

wherein each Az is independently selected from $NH_2$, NHAc, and $N_3$;
Z represents a spacer moiety that is capable of conjugating to a protein, and that may be in protected form or unprotected form and that may be conjugated to a protein;
each $R^1$ is independently H, optionally substituted C1-C6 alkyl, or M, where M represents a cation;
X is O or $CH_2$;
each $R^3$ and $R^4$ is independently selected from the group consisting of H, Ac, Bn, and other protecting groups;
and $R^6$ is H, or a protecting group, or a phosphate, or a linkage to an additional saccharide unit.

In this aspect of the invention, some embodiments comprise a protein that is conjugated to the oligosaccharide through a spacer moiety that is in the alpha-configuration at C-1 of the first mannose unit. The protein is sometimes an inactivated bacterial toxin selected from diphtheria toxoid, pertussis toxoid, E. coli LT, E. coli ST, Pseudomonas aeruginosa exotoxin (rEPA), or tetanus toxoid, or the protein may be CRM197. The protein in these embodiments may be linked to the oligosaccharide of formula (1) through a spacer moiety, which comprises a hydroxyl or an amine, either of which is optionally protected or is optionally conjugated to a protein. In some embodiments of this aspect, $R^3$ is an acyl group and $R^4$ is H. The alternate or preferred embodiments of formula (1) also apply to formula (1').

In certain aspects, the invention provides a method to synthesize an oligosaccharide of alpha-linked mannose units, which comprises combining a mannose unit comprising formula (2), wherein $R^6$ is C1-C6 acyl or H, and $R^1$, $R^3$, $R^4$, Az and Z are as defined in claim 15;

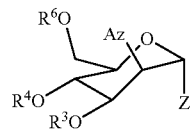

(2)

with an elongating monomer of formula (3), wherein $R^x$ represents a C1-C6 acyl group and M represents H or a cation;

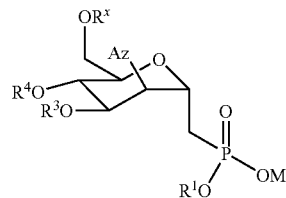

(3)

under Mitsunobu reaction conditions, to produce an oligosaccharide comprising at least two 2-aza substituted mannose units connected by a 1,6-alpha linkage. In some embodiments of this method, the Mitsunobu conditions include the use of either diisopropyl azodicarboxylate (DIAD) or diethyl azodicarboxylate (DEAD) and either triphenyl phosphine or a substituted triphenyl phosphine such as tris(p-chlorophenyl)phosphine. In some embodiments, DIAD and tris(p-chlorophenyl) phosphine are used, and triethylamine is used in excess. In certain embodiments, the Mitsunobu reaction conditions are maintained for a prolonged period of time, and the product is an oligosaccharide of formula (4),

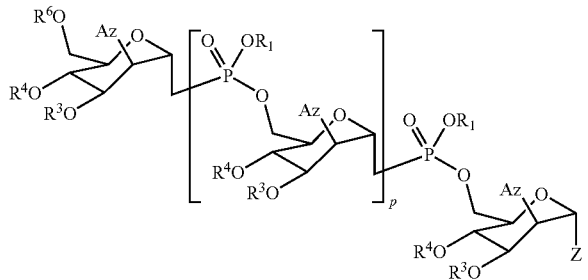

(4)

wherein p is an integer from 1 to 20.
In many of these embodiments, each Az represents either NHAc or $N_3$. In some of these embodiments, p is 1-10, and in others, p is about 1-5 or p is 2-4. In certain of these embodiments, the methods of the invention further include a method to conjugate the oligosaccharide of formula (4) to a protein. Optionally this is done through Z, which is often a spacer moiety selected to be capable of conjugating to such proteins. In some of these embodiments, the protein is an inactivated bacterial toxin selected from diphtheria toxoid, pertussis toxoid, E. coli LT, E. coli ST, Pseudomonas aeruginosa exotoxin (rEPA), or tetanus toxoid. In other embodiments, the protein is CRM197.

In other aspects, the invention provides an oligosaccharide that is prepared by the foregoing methods. The oligosaccharide compounds prepared by these methods are immunogenic compounds, and typically elicit an immunogenic response in a treated mammal which provides at least partial immunity to infections caused by N. meningitidis.

In still other aspects, the invention provides a method to use any oligosaccharide compounds of the invention to elicit an immunogenic response, typically by administration to a mammal. In many embodiments, these compounds are used as a Meningitidis A vaccine component; the methods thus often comprise administering an effective amount of the vaccine component to a subject, thereby providing an immunogenic response. The immunogenic response provides at least partial resistance or immunity in the subject to meningitis caused by N. meningitidis A.

The invention also provides pharmaceutical compositions comprising at least one oligosaccharide of the invention admixed with at least one pharmaceutically acceptable excipient to provide a pharmaceutical composition that is immunogenic. In some embodiments, these compositions are thus vaccines including a Meningitidis A vaccine comprising any compound of the invention. In many embodiments, the vaccine comprises at least one oligosaccharide conjugated to a protein.

In yet other aspects, the invention provides methods for making a mannose derivative useful for the preparation of an immunogenic oligosaccharide, including those of the invention. These methods comprise cyclizing a compound of formula (2) with an electrophile

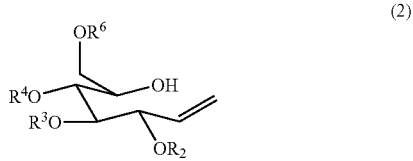

(2)

to form a compound of formula (3),

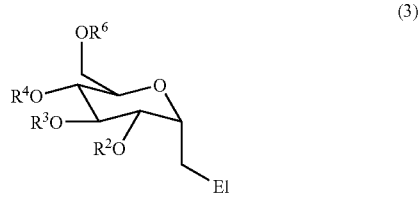

(3)

wherein each of $R^2$, $R^3$, $R^4$ and $R^6$ is independently H or a protecting group;
and El represents a residue derived from an electrophile.
In certain embodiments, the methods include an additional step that comprises the step of replacing El with a phosphorus group. The phosphorus group is typically a phosphonate. In some embodiments, the invention also provides methods for $OR^2$ in a compound of formula (2) or formula (3) with an azide. In preferred embodiments, the replacement of $OR^2$ comprises a Mitsunobu reaction. In some such embodiments, a phosphoryl azide provides the azide for the Mitsunobu reaction.

In still other aspects, the invention provides an improved method to prepare a 2-azido-2-deoxy-D-mannopyranose, which method comprises:
forming a triflate at position 2 of a 1,3,4,6-tetra-O-acyl glucopyranose derivative; and
displacing the triflate with an azide nucleophile.

Other methods for making such compounds may be used, and the present improved method provides for precautions to minimize exposure to moisture during work-up and isolation of the product. This resulted in greatly improved yields over known methods, e.g., Popelova, et al., Carbohydrate Res. (2005) 340:161-166. In a preferred embodiment, the 1,3,4,6-tetra-O-acyl glucopyranose derivative is 1,3,4,6-tetra-O-acetyl glucopyranose, and the product is 2-azido-1,3,4,6-tetra-O-acyl mannopyranose.

In other aspects, the invention provides an immunogenic composition capable of eliciting protective antibodies against Meningitidis A, which comprises an oligosaccharide having at least two saccharide units, which are typically mannose units, covalently attached to each other through a stabilized phosphorous-containing linkage. In many such embodiments, at least one saccharide unit, which may be a mannose unit, comprises an alpha-linked spacer moiety at its anomeric center. The stabilized phosphorus-containing linkage can comprise a phosphonate. In certain embodiments, these oligosaccharides comprise at least two mannose units covalently attached to each other through a stabilized phosphorous-containing linkage. In many of the embodiments, the oligosaccharide is conjugated to a protein. Many proteins such as those described above as suitable carrier proteins can be used, but in preferred embodiments the protein is not albumin. In some embodiments, the immunogenic compositions of the invention comprise at least 2 different oligosaccharide moieties. In many of the embodiments, the stabilized phosphorus-containing linkage between two saccharides comprises a phosphonate. In many such embodiments, the phosphonate linkage is a 1,6-linkage, formed by a Mitsunobu reaction, and in certain embodiments, the oligosaccharide of any of the foregoing compositions comprises at least one mannose unit which comprises an alpha-linked spacer moiety at its anomeric center.

In some of the immunogenic compositions of the invention, the composition comprises at least two different oligosaccharides that are specific for at least two meningococcal immunotypes. The compositions may also include other antigenic compounds, and in some embodiments, the compositions further comprise a Streptococcus Pneumoniae antigen. This antigen is a polysaccharide in some embodiments, and in many of these embodiments the polysaccharide is conjugated to a protein.

In some embodiments, the compositions of the invention also comprise at least one antigen derived from a Meningitidis of serotypes A, B, C, W135, or Y. In some preferred embodiments, this antigen is derived from Meningitidis serotype C, W135, or Y. The compositions of the invention often further comprise an adjuvant, and in some of the embodiments the adjuvant is alum.

In many compositions of the invention, the oligosaccharide component is conjugated to a protein through a bifunctional reagent comprising a dicarboxylic acid or a derivative thereof. In many embodiments, this dicarboxylic acid comprises adipic acid or suberic acid or a derivative thereof. In other embodiments, the bifunctional reagent comprises a squarate.

The preparation of phosphonate-linked compounds within the scope of the invention can be accomplished by making an acceptor monomer and an elongating monomer, each of which is an appropriately modified mannopyranose ring, referred to as a mannose unit. The elongating monomer is attached to the acceptor through a phosphonate linkage to make a disaccharide. The elongating monomer can be adapted to allow its C6 hydroxyl to be deprotected selectively; thus, if a longer oligosaccharide is desired, the elongating monomer in the dimeric saccharide can become an acceptor. It can be deprotected without deprotecting the C3 and C4 hydroxyls, so the C6 hydroxyl can be linked to the phosphonate of another elongating monomer. This process can be iterated as many times as necessary to provide an oligosaccharide of the desired length.

Figure 3:
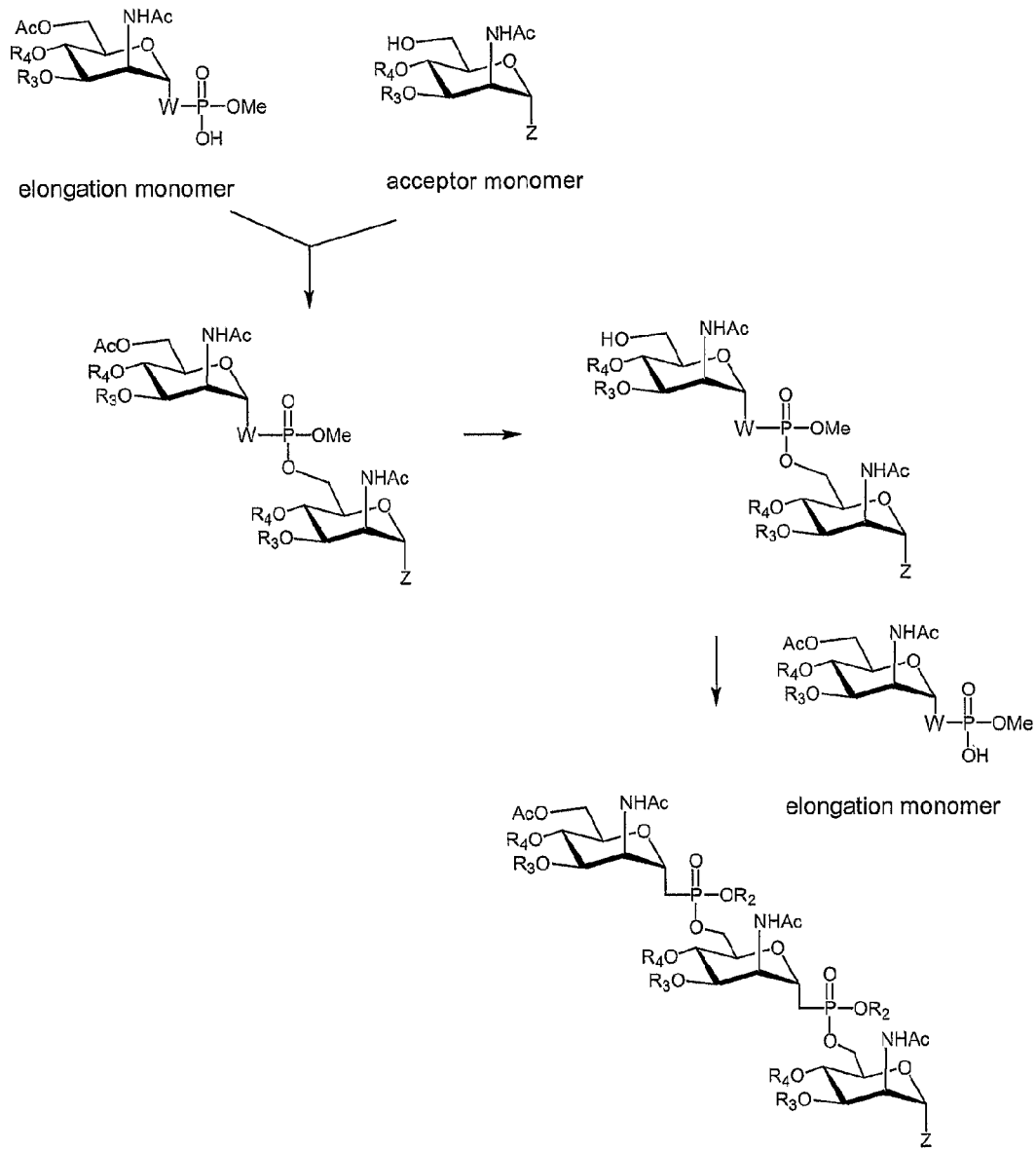
FIG. 3 shows the modular assembly strategy for the synthetic oligosaccharides.

FIG. 3 depicts how an acceptor monomer and an elongation monomer are linked to form an oligosaccharide having two mannose units (i.e., a disaccharide), and how this disaccharide can be extended further by deprotection of the C6 hydroxyl followed by attachment of another elongation monomer. Optionally, the acceptor monomer may be attached to a solid support by a cleavable linker to facilitate handling and isolation. In that case, the oligosaccharide can remain attached to the solid support through multiple iterations of the elongation process, and can eventually be cleaved to release a relatively pure oligosaccharide product of the desired length. The spacer moiety Z is sometimes used to link the oligosaccharide to the solid support during synthesis, and then used, optionally with modification, to conjugate the oligosaccharide to a protein.

The invention provides methods to make immunogenic oligosaccharides containing two or more modified mannose units, as well as longer oligosaccharide or polysaccharide molecules, and methods to make the oligo- and/or polysaccharides into more immunogenic materials by conjugating them to a protein. The mannose units are pyranose rings having the basic structure of a mannose ring, but having at least some structural modifications. In many embodiments, the invention includes at least one substituent where a nitrogen atom or other heteroatom is bonded to a ring carbon in place of one of the hydroxyl groups of mannose; as used herein, such substituted rings are considered mannose units as long as the array of substituents on the pyranose ring has the same relative stereochemistry as the array of stereocenters on mannose. Note that the mannose configuration does not define the stereochemistry at C-1; C-1, which is the anomeric center in a mannose unit, can be in either the alpha or the beta configuration. Thus a mannose unit can have a C, N, or S atom attached in place of one of the mannose hydroxyls, or can have two or more of such modifications. The structure and numbering of carbon atoms for D-mannose is provided here for reference.

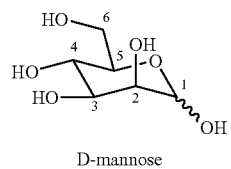

D-mannose

The methods of the invention can be used with mannose units having the absolute stereochemistry of either D-mannose or an L-mannose; in many embodiments the absolute stereochemistry is that of D-mannose. However, an oligosaccharide of the invention can include one or more mannose units having the L-mannose configuration. It can also, of course, be linked to additional saccharide or peptide moieties, for example, as long as it includes at least two mannose units linked as described herein.

The oligosaccharides of the invention include at least two pyranose rings linked together; if only two rings are included, the molecule can be described as a dimer; with three linked in sequence it can be described as a trimer; and so forth. However, the generic term oligosaccharide as used herein includes these smaller embodiments as well as longer polymer versions having three or more, five or more, seven or more, ten or more, fifteen or more, twenty or more, and more than 25 monomers in sequence. Versions having more than about five saccharide rings are sometimes referred to herein as polysaccharides. In many embodiments the oligosaccharide comprises at least three mannose units.

Regardless of the number of mannose units included, it is sometimes desirable to link the oligosaccharide to other molecular features, so the mannose units may be substituted with various groups, and the oligosaccharide may be linked through one or more mannose units, typically through one of the terminal mannose units, to another moiety. In some embodiments, it is beneficial to link the oligosaccharide to a protein, and these glycoconjugate forms are specifically included within the invention. Typically the glycoconjugate is formed by conjugation of the protein of interest to a functional group on the spacer moiety attached at C-1 of the first mannose in the oligosaccharide, and the spacer moiety is in the alpha configuration. In many embodiments, it is desirable to attach a protecting group or other functionality to one or more of the heteroatom substituents on the mannose unit. In some preferred embodiments, the heteroatom substituents are selected from OH, OAc, $NH_2$, $N_3$, NHAc, and an O, N, or S that is connected to a protecting group or to a protein.

The mannose units are typically connected by a 1,6-linkage. The 1,6 linkage means that the C-1 carbon, the anomeric center, of the second mannose unit is connected, either directly or indirectly, to the C-6 carbon of the first mannose unit by a linkage that includes no intervening saccharide rings. Typically the linkage between two mannose units will include at least two atoms, generally two or more non-carbon atoms, between the mannose unit carbon atoms. In many embodiments the linkage is of the general form:

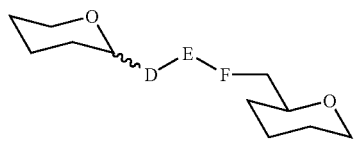

where each of D, E and F represents a heteroatom selected from O, N, S, Si, and P, and each of the tetrahydropyran rings represents the ring of a mannose unit. In some embodiments E represents a phosphorous atom, which is often in the oxidation state of a phosphate or a phosphonate. Typically, at least one of D and F in this formula is oxygen (O), and in some embodiments both D and F are oxygen. Particular embodiments include those wherein D-E-F represents O—P(O)—O or C—P(O)—O or O—P(O)—C. Sometimes D-E-F is preferably a linkage comprising —$CH_2$—P(O)—O—.

In some embodiments, the linkage between adjacent mannose units is a 1,6-alpha (1,6-α) linkage. For mannose units, the 1,6-alpha linkage means that the non-H substituent at C-1, which corresponds to the anomeric center carbon of mannose, is in an 'anti' relative stereochemical relationship to the non-H substituent at C-2. Alternatively, one or more mannose units in an oligosaccharide may be linked through a beta linkage. (The configuration having the linkage at the anomeric center 'syn' to the C-2 substituent in a mannose is referred to as a beta linkage.) However, typically the compounds are linked together in an alpha relationship, regardless of the nature of the linkage itself.

The following structures illustrate the difference between the alpha and beta linkage orientations.

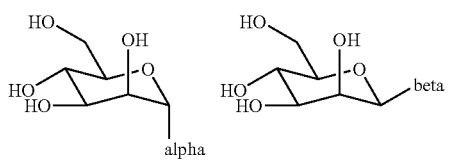

Many embodiments of the invention include an aza substituted mannose unit, which means that at least one of the mannose hydroxyls has been replaced with a substituent referred to herein as an "aza" substituent. This is a substituent wherein at least the atom linked directly to the mannose unit is nitrogen. Aza substituents include $NH_2$ and various substituted amines, including alkylated and dialkylated amines, and acylated and diacylated amines, where the acyl groups include heteroacyls such as benzyloxycarbonyl and methoxycarbonyl as well as such acyl groups as acetyl, formyl, and benzoyl. Other embodiments of the aza substituent include $NO_2$ and $N_3$. Some embodiments of the aza substituted mannose units of the invention have the aza substituent at C-2 of the mannose ring, and preferred embodiments include compounds and methods wherein the aza substituent on a mannose unit is $NH_2$, $N_3$, or NHAc.

Thus in some embodiments, the compounds and methods of the invention comprise a moiety of formula (1):

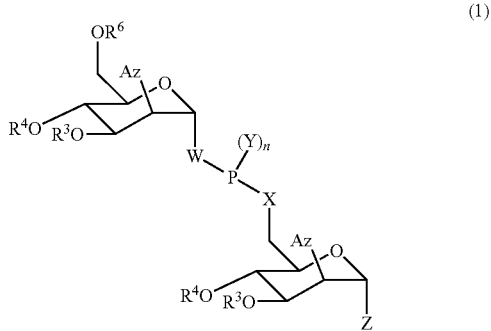

(1)

wherein each Az represents an aza substituent;
each $R^3$ and $R^4$ independently represents H or a protecting group;
$R^6$ represents H, a protecting group, or a linker attached to another saccharide unit;
one of W and X is O, and the other of W and X is $CH_2$;
n is 1 or 2;
$Y_n$ is OR when n is 1, and when n is 2, one Y is =O and the other Y is OR,
wherein R is H, C1-C6 alkyl, or C6-C12 aryl, or C6-C12 arylalkyl, or R is M, where M is a cation; and Z is OR', SR', NR'$_2$, or halo, where each R' is independently H or an optionally substituted alkyl, acyl, aryl, arylalkyl, heteroalkyl, heteroacyl, heteroaryl, or heteroarylalkyl group;
or Z represents a linker attached to another saccharide unit or a spacer moiety conjugated to a protein.

Preferred aza substituents are those in which a nitrogen atom is directly bonded to the mannose unit. Examples of such substituents include $N_3$, $NH_2$, NH-alkyl, NH-acyl, NH-aryl and the like. Each N in these substituents can optionally include one or two groups selected from alkyl, aryl, and acyl, where each alkyl, acyl and aryl is optionally substituted.

The term "protected" or a "protecting group" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, which can be added or removed using the procedures set forth therein. Examples of protected hydroxyl groups include, but are not limited to, silyl ethers, such as TBDMS or TBS, such as those obtained by reaction of a hydroxyl group with a reagent such as, but not limited to, t-butyldimethyl-chlorosilane, trimethylchlorosilane, triisopropylchlorosilane, and triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, and benzyl ether; esters such as, but not limited to, benzoyl, benzoylformate, formate, acetate, trichloroacetate, and trifluoracetate. Examples of protected amine groups include, but are not limited to, benzyl or dibenzyl, amides such as, formamide, acetamide, trifluoroacetamide, and benzamide; imides, such as phthalimide, and dithiosuccinimide; and others. In some embodiments, a protecting group for alcohols is a benzyl group or an acetyl group, and a typical protecting group for an amine herein is acetyl or a benzyl or t-butyl carbamate.

"Protecting group" as used herein include those moieties recognized in the art as protecting groups for the heteroatoms N, O and S, and are described, for example, in the reference book by Greene, T. W., and Wuts, P. G. M., *Protective Groups in Organic Synthesis,* 2d ed., Wiley and Sons (1991), which is incorporated herein by reference. Acetyl (Ac) is one such protecting group, and because the natural CPS of *N. meningitides* is often acetylated, particularly at C-3, in some embodiments of the invention, one or more of the protecting groups is Ac; and in some preferred embodiments, $R^3$ on at least one of the mannose units represents Ac.

In some of these compounds, one of X and W is $CH_2$, while the other one is O; for example, in some embodiments X and W are both O, and in others, W is $CH_2$ and X is O. Within a given compound of the invention that is oligomeric and contains three or more mannose units, different embodiments of the linkage may be present; thus two mannose units linked together by a linkage comprising a phosphonate may be linked to a third mannose unit via a phosphate diester linkage without departing from the invention.

It is often desirable to conjugate the oligosaccharides of the invention with another molecule, typically a protein. Conjugates made by such methods are within the scope of the invention. Thus conjugation of a saccharide to a protein is often accomplished by adding a reactive bi-functional molecule to the protein then exposing the derivatized protein to the saccharide, so that the saccharide becomes covalently linked through the linker provided by the bi-functional reagent, which often is attached to one of the hydroxyl groups of the saccharide. In the controlled synthesis of compounds of the invention, however, it is especially convenient to include a spacer moiety specifically designed for conjugating the oligosaccharide to a protein. Such a spacer moiety can be attached to any one of the mannose units in an oligosaccharide; however, typically it is on a terminal mannose unit, either the first 'acceptor' monomer, or the last 'elongation' monomer. Frequently it is at C-1 of the acceptor or C-6 of the elongation monomer, and in compounds of formula (1) it may be the group represented by Z or the one represented by $R^6$.

The spacer moiety for conjugating the oligosaccharide to a protein may comprise a multi-atom spacer moiety to make the immunogenic epitope of the oligosaccharide more available and thus more effective. Alternatively, for example, Z in a compound such as those represented by formula (1) can be a single atom such as O or N or S, and a space between the oligosaccharide and the protein may be provided by a bi-functional reagent used to link the oligosaccharide and a carrier protein together. The bifunctional reagents suitable for use in the glycoconjugates of the invention include those known in the art. Examples of such include di-carboxylic acids such as malonic, succinic, adipic and suberic acids or activated versions thereof, and squaric acid derivatives. These types of reagents are particularly convenient for linking a compound wherein the spacer moiety comprises an amine to a protein.

In some embodiments, the spacer moiety is at least two or three atoms in length, though it optionally may be a single atom or it may be much longer; one example is a compound of formula (1), wherein Z represents a 2-aminoethoxy group. The 2-aminoethoxy group or a homolog thereof can be introduced into the acceptor monomer before elongating monomers are attached, and is optionally introduced in protected form so it does not participate in the subsequent reactions. The spacer moiety must include at least one functional group that is capable of being used to link the oligosaccharide to a protein, and typically it includes a heteroatom, N, O or S, for this purpose, though other groups such as a diene or a dienophile for linkage through a Diels-Alder reaction, or a carboxylate group for conjugating the protein to the oligosaccharide through an ester or amide are also contemplated. In many embodiments such as the 2-aminoethoxy group discussed above, the spacer moiety includes a nitrogen for this purpose; the nitrogen may be protected when it is introduced and during construction of the oligosaccharide, but is capable of being selectively deprotected after the oligosaccharide has been constructed under conditions that do not destroy the oligosaccharide. The amine of the spacer moiety is then readily acylated or alkylated, for example, with a bi-functional reagent, the other end of which is similarly attached to a protein. The order of such attachment, i.e., which piece of the glycoconjugate is attached to the bi-functional reagent first, is unimportant and is determined by the judgment of the practitioner. Some typical, but non-limiting examples of spacer groups include -Het-$(CH_2)_n$-A, -Het-Ph-A, -Het-$(CH_2)_n$-Ph-$(CH_2)_n$-A and substituted forms thereof, wherein each Het represents a heteroatom, usually O, S or N; each Ph represents a phenyl group, optionally substituted; and each n represents an integer from 1-10; A represents a functional group or a residue thereof that is capable of or links the spacer to the protein, such as an N, O, or S, or ester, an amide, or other carboxyl-containing group, a diene, or a dienophile. Preferably, the spacer comprises OR', SR', or NR'$_2$, where each R' is independently H or an optionally substituted alkyl, acyl, aryl, arylalkyl, heteroalkyl, heteroacyl, heteroaryl, or heteroarylalkyl group and may further comprise A.

M in formula (1) can represent an alkali metal cation, selected from Li, Na, K, and Cs, or an ammonium salt $NR_4^+$, where each R is independently H or C1-C6 alkyl or C1-C6 heteroalkyl. Alternatively, it can represent any other pharmaceutically acceptable cationic species such as MgX or CaX, where X represents halo, hydroxyl, acetoxy, trifluoroacetoxy, bisulfate, bicarbonate, or any other suitable species. In some embodiments, M is a divalent cation, and is shared by two molecules of formula (1).

The methods of the invention provide ways to synthesize the oligosaccharide compounds within the invention. The methods include, for example, ways to link two mannose units together in a desired fashion, such as by forming a 1,6-alpha linkage between two mannose units. Where the 1,6-alpha linkage is a phosphate or phosphonate such as the compounds of formula (1) where X is O, the linkage can be created by a Mitsunobu reaction. The Mitsunobu reaction is described, for example, in Campbell, D. A., *J. Org. Chem.* (1992) 57:6331-6335, and involves an activation of an alcohol with a reagent such as an azodicarboxylate, e.g., DEAD or DIAD, and a phosphine (e.g., triphenyl phosphine or tris(p-chlorophenyl)phosphine), followed by displacement of the activated O by a nucleophilic species. In the case of compounds of formula (1) where X is O, the nucleophile is usually a P—O$^-$ species, typically a phosphonate or phosphate anion. In other aspects of this invention, a Mitsunobu reaction is employed to introduce an aza substituent to a saccharide group, in which case the conditions are similar except that the nucleophile is an azide, which may be supplied as an azide anion or as a trialkylsilyl azide or a phosphoryl azide.

The methods of the invention also provide ways to install and modify N-substituents (aza substituent) on the mannose units of compounds such as those of formula (1). Thus in some embodiments, the methods provide ways to insert an aza substituent into a mannose unit with the proper stereochemistry. One such method comprises displacing a C-2 hydroxyl on a pyranose ring with an N-substituent, typically $N_3$. It can be inserted with a nucleophilic displacement reaction, but in some embodiments it is inserted via a Mitsunobu-type reaction with the assistance of an activating group such as an azodicarboxylate, e.g., DEAD or DIAD. The nucleophile for this Mitsunobu reaction can be provided by a phosphoryl azide such as diphenyl phosphoryl azide. The particular improvement provided by the present invention in this reaction comprises the use of a phosphoryl azide as the source of the aza substituent, and the incorporation of substantially water-free work-up conditions to avoid decomposition of the product. Under the conditions described herein, the yield of the 2-azido derivative of a mannose unit is substantially improved over methods of the prior art.

In some preferred embodiments, at least one of the mannose units of an oligosaccharide of the invention is an aza-substituted mannose having an amine or acylated amine, which is often at C-2 of the mannose unit. In some embodiments of the methods of the invention, the aza substituent is inserted as $N_3$, which can be reduced to provide an amine, and the amine can be acylated under conditions such as those described in the Greene and Wuts book on protective groups referenced above. Reduction of the azide ($N_3$) to $NH_2$ is readily accomplished by typical methods, such as using nickel borohydride, which can be generated in situ from nickel chloride hexahydrate and sodium borohydride as described herein.

In some embodiments, the invention provides oligosaccharides and methods to make oligosaccharides, wherein the oligosaccharide comprises a repeating series of aza-substituted mannose units; in many embodiments, each of the mannose units has an aza substituent, typically $N_3$, $NH_2$ or NHAc, at C-2 of each mannose unit—e.g., in the compounds of formula (1), Az would be $N_3$, $NH_2$ or NHAc. Optionally, the linkage between at least two of the mannose units is a phosphonate linkage which may be a 1,6-alpha linkage such as the one in the compounds in formula (1), where W is $CH_2$ and X is O. Such 1,6-alpha linkages comprising a phosphate or a phosphonate, such as the compounds in formula (1) where W is either $CH_2$ or O and X is O, can be formed by the Mitsunobu reaction described above. Preferably, the Mitsunobu is done under modified conditions that are described by Campbell, as referenced above.

In another aspect, the invention provides an improved method to make certain saccharide molecules that are useful for synthesis of the oligosaccharides described above. Thus the invention provides methods to synthesize certain phosphonate-substituted monosaccharides. For example, a compound of formula (2), which is available from glucose, can be converted into a precursor for a phosphonate ester useful for forming the phosphonate-comprising 1,6-alpha-linkage shown in formula (1) where W is $CH_2$ and X is O. The method includes cyclizing a compound of formula (2) with an electrophile

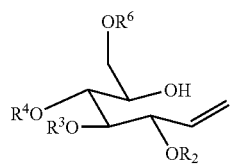

(2)

to form a compound of formula (3).

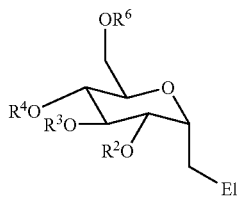

(3)

wherein each of $R^2$, $R^3$, $R^4$ and $R^6$ is independently H or a protecting group;
and El represents the residue of an electrophile.

The electrophile used to effect the cyclization may be a mercury salt, in which case after cyclization to the compound of formula (3), the residue of the electrophile is typically —HgX, where X is halo, acetoxy, or the like. The mercury can be replaced by treatment with iodine, giving a compound of formula (3) wherein El is I. The iodide can then be displaced with a phosphorus nucleophile; for example, treatment with trialkyl phosphite directly displaces the iodide and produces a dialkyl phosphonate. Other electrophiles may also be used to effect the cyclization; for example, halocyclizations are known, and would directly provide a halide as El, which could be displaced. Similarly, methods can be used whereby the olefin can be epoxidized with the correct stereochemistry so that opening of the epoxide can result in the pyranose ring, and a compound of formula (3), wherein El is OH. The OH can then be converted to a halide or a displaceable sulfonate such as a triflate, tosylate or mesylate, and the phosphorus can be introduced as described above with triethyl phosphite, or it can be introduced by direct nucleophilic substitution using an anionic P species such as the sodium anion of diethyl phosphite.

This provides a glucose derivative of formula (3) rather than an N-substituted mannose unit; thus the invention further provides methods to convert $OR^2$ in formula (2) or formula (3) into an aza substituent having the desired 'axial' orientation. This introduction of a nitrogen substituent is often accomplished by reacting a compound of formula (3) with an activating agent to form a compound wherein $R^2$ is a displaceable group, such as a triflate, tosylate or mesylate. Since such displacements in (2) would result in allylic rearrangement, this conversion is often done on a compound of formula (3). While it is possible to do this reaction by ordinary nucleophilic displacements, in one embodiment of the invention, this replacement of $OR^2$ with an aza substituent is done using a Mitsunobu reaction. In a preferred embodiment, the Mitsunobu reaction employs a phosphoryl azide as the source of the aza substituent. Thus, the reaction provides a very efficient way to convert a readily available glucose-derived compound such as (2) into a 2-deoxy-2-aza-substituted mannose derivative, wherein the 2-aza-substituent is an azide. The azide can then be reduced to an amine such as treatment with nickel borohydride; and the amine can be functionalized or protected as desired. In many embodiments of the invention, the amine is immediately acylated with a protecting group, often with acetyl (Ac), since the acetyl group can serve as a protecting group and also appears in the mannose unit of the CPS of *N. meningitidis*.

In another aspect, the invention provides a greatly improved method for making a 2-aza-substituted mannose derivative in protected form. The method comprises displacing the 2-hydroxyl group of an otherwise protected glucopyranose ring by conversion of the 2-hydroxyl to a triflate followed by displacement of the triflate with azide. The nucleophilic displacement inverts the center, thus converting the glucopyranose into a mannopyranose. While the displacement itself has been reported, it proceeds in very poor isolated yield using standard conditions. In the present invention, it has been found that a high yield of the desired product can be obtained using the readily available 1,3,4,6-tetra-O-acyl glucopyranose, as long as the work-up of the reaction is done substantially without water. Thus the triflate is displaced by azide anion in a polar aprotic solvent such as DMF or NMP; then, rather than using an ordinary aqueous/organic extractive workup to remove most of the solvent and salts, the reaction mixture may be partially concentrated before it is directly applied to a chromatography column. Using such a non-aqueous work-up, the product can be eluted from the column in high yield.

The following description provides more detail on the methods for making certain compounds of the invention.

One embodiment of a starting monomer acceptor, compound XIV shown below, is described in Berkin, A. et al., *Chem. Eur. J.* (2002) 8:4424-4433. As an alternative, the following sequence may be used:

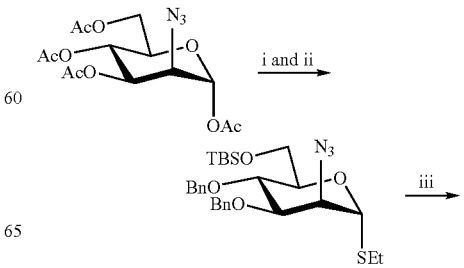

-continued

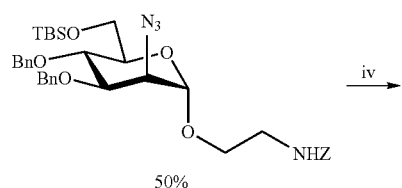

50%

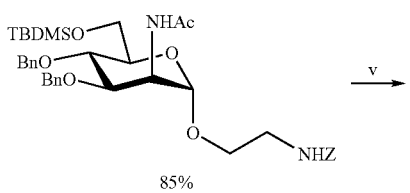

85%

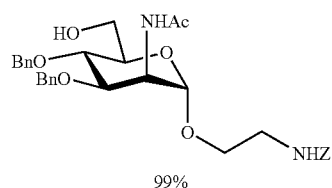

99%

(i) TBDMSCl, pyr
(ii) BnBr, NaH
(iii) NIS, AgOTf, HO(CH$_2$)$_2$NHZ
(iv) 1. NaBH$_4$, NiCl$_2$(H$_2$O)$_6$ 2. Ac$_2$O
(v) TBAF

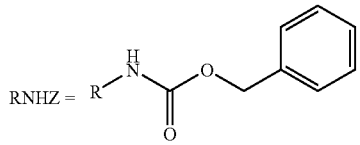

When the di-benzyl protected compound was used to introduce the spacer at the anomeric center, about a 1:1 mixture of anomers was obtained. If instead the benzyl ethers are replaced with acetate esters, only traces of the beta anomer are obtained, and an 86% isolated yield of the desired alpha anomer resulted. Thus, the method provides an efficient way to produce the desired alpha configuration at this center, which is often the center to which a spacer connecting the oligosaccharide to a carrier protein is attached. The alpha configuration is desired because it best matches the all-alpha skeleton of the natural CPS of the target organism. It was also found that the beta anomer was less reactive in the ethylthioglycoside replacement step. However, the acetates sometimes cause difficulties later in the sequence, so in some embodiments, the benzyl ethers were utilized for this step. The azido group of the fully protected 2-aza mannose intermediate was reduced to an amine again using NaBH$_4$/cat. NiCl$_2$-6H$_2$O, and the amine was acetylated with acetic anhydride in 85% yield over both steps. Finally, the silyl ether was removed with TBAF to obtain the starting building block acceptor in 99% yield.

A convenient synthesis of the desired elongation monomers is shown in Schemes 1-3 below, which allow one to prepare elongation monomers having different protecting groups, for example.

Scheme 1

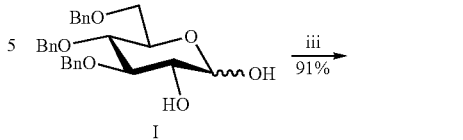

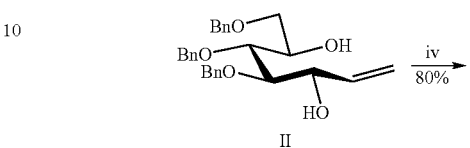

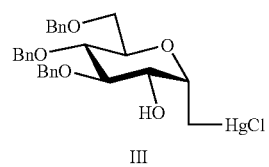

(i) MeOH/collidine
(ii) BnBr/KOH, HOAc (70%), NaOMe/MeOH
(iii) BuLi/methyl triphenylphosphonium bromide
(iv) Hg(OAc)$_2$, KCl Compound I was obtained and used as a mixture of anomers, and was obtained in seven steps from glucose. It was elongated via a Wittig reaction with methyl bromotriphenylphosphine, for example, to afford the alkene in 91% yield. Another preparation of this alkene from D-arabinose used a two carbon elongation that involves addition of divinylzinc. Mercury cyclization of compound II afforded exclusively the alpha-C-glycoside, though the corresponding tetra-O-benzyl protected alkene yields a mixture of anomers. Alternative methods for cyclizing such species, such as halo-etherification and epoxidation/electrophilic ring opening may be used. The mercury acetate compound was converted to the corresponding mercury chloride derivative, which was isolated. The mercury chloride was subsequently replaced with iodine in excellent yield by treatment with I$_2$.

Scheme 2

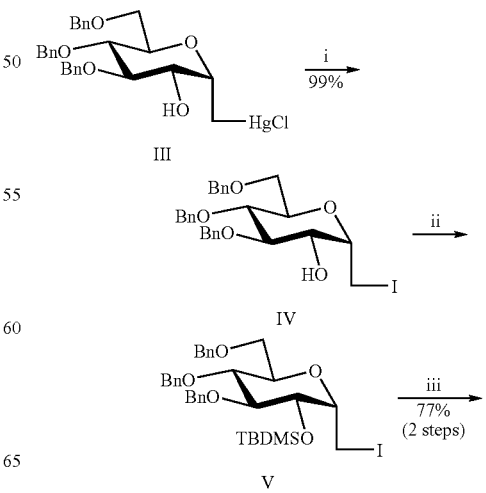

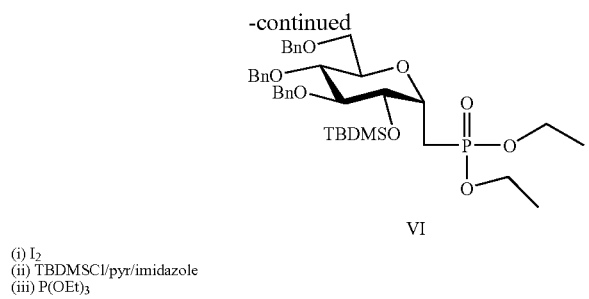

(i) $I_2$
(ii) TBDMSCl/pyr/imidazole
(iii) $P(OEt)_3$

To avoid formation of a cyclic phosphate in the next step, the C2 hydroxyl group was first protected as a silyl ether. The C-phosphonate VII was obtained by treatment of the primary iodide V with triethyl phosphite to give VI in 77% yield. The silyl ether was subsequently cleaved from the C2 hydroxyl using tetrabutylammonium fluoride (TBAF) in 99% yield.

The axial acetamido group was introduced by a displacement reaction with azide followed by reduction and acetylation as shown in Scheme 3. The displacement inverts the C-2 center, providing the axial orientation of the C-2 acetamide substituent that is found in the natural capsular polysaccharide. This azide was introduced in low yield by preparing a triflate of the C-2 hydroxyl and displacing it with azide anion. However, by using Mitsunobu conditions and diphenylphosphoryl azide (DPPA) as the azide source, a high yield (86%) of the azido derivative IX was obtained. To introduce a selectively removable protecting group at O-6, the primary benzyl ether of VIII was replaced with an acetate ester in 84% yield using standard acetolysis conditions; that step could be omitted, in which case all of the benzyl ethers could be cleaved at once. Omitting the acetolysis shortens the synthesis, but makes it more difficult to use the C-6 hydroxyl for further elongation or other functionalization, although exchange of the benzyl for an acetyl can also be done after an elongation step. The acetolysis reaction worked better when a mixture of acetic anhydride and acetic acid (1/1) was used together with sulphuric acid. The azide was reduced with sodium borohydride in the presence of nickel chloride hexahydrate, and the resulting amine was acetylated with acetic anhydride to give compound X in 69% yield.

Scheme 3 illustrates completion of an elongating monomer within the invention that is a 2-aza mannose unit. For the construction of the elongating C-phosphonate monomer a modified version of a published approach was used. See Casero, F., et al., *J. Org. Chem.* (1996) 61:3428-3432. After desilylation of precursor VI to afford the 2-OH compound VII, azide displacement using Mitsunobu conditions gave the 2-azido-2-deoxy-mannopyranoside VIII (86%). An orthogonal protecting group, to allow later 6-O elongation, was introduced by acetolysis to afford the 6-O-acetate IX (84%). Azide reduction followed by acetylation gave X (76%), from which the ethyl esters were removed to yield the elongating monomer XI with a free phosphonic acid. For many embodiments, it is preferred to couple a mono-ester of the phosphonic acid, so that the product remains protected as a phosphonate ester. These compounds can be prepared in two steps as shown below for conversion of XI to XIII. Note that the azide reduction can be postponed until additional mannose units have been installed if longer oligosaccharides are desired, so that all of the azides can be reduced and the resulting amines acetylated simultaneously.

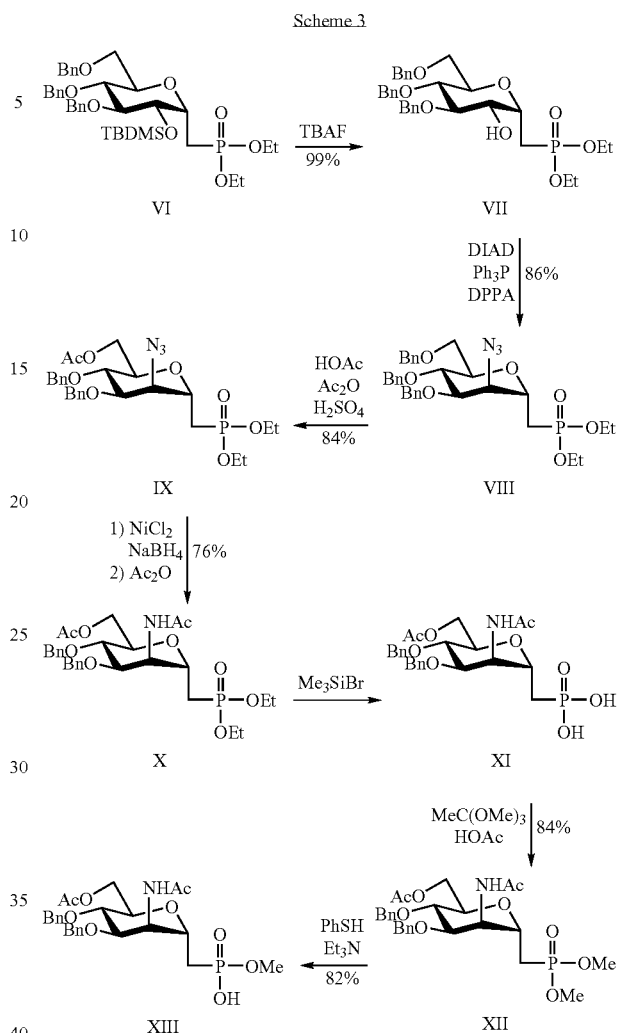

Scheme 3

The ethyl protecting groups on the phosphonic acid derivative were replaced with methyls as shown in Scheme 3 above to facilitate removal after an oligosaccharide has been constructed. Once the linked disaccharide has been formed, the linkage is relatively labile under the conditions needed to cleave the ethyl phosphonates. The ethyl groups were thus removed quantitatively by treatment with bromotrimethyl silane (TMSBr), and the phosphonic acid product was converted to its corresponding dimethyl phosphonate in 84% yield using acetic acid and trimethylorthoacetate. This reaction had to be carefully monitored since deacetylation is a competing side reaction during prolonged reaction times. Treatment of the dimethyl phosphonate with triethylamine (TEA) and phenyl mercaptan efficiently afforded the mono methyl phosphonate XIII in 82% yield.

Scheme 4 illustrates the coupling reaction to establish a phosphonate linkage between two mannose units. Both DCC and Mitsunobu conditions have been reported for coupling a phosphonate to an alcohol like the acceptor monomer, with yields in the range of 50-70%. Pozsgay, et al. (See, A. Berkin, B. Coxon and V. Pozsgay, *Chem. Eur. J*, 2002, 8, 4424.) However, when the acceptor already contained a phosphonate, the yields dropped sharply, which could limit the ability of such conditions to provide the desired trimers, tetramers, and other longer polysaccharides. Mitsunobu conditions in the present case, using Ph₃P and DIAD, gave a good yield (47%) of XV. However, substantially better yields were realized using a modified version of the Mitsunobu conditions, as described in Campbell, *J. Org. Chem.* (1992) 57:6331-6335. The conditions from Campbell, using tris(4-chlorophenyl) phosphine and a large excess of triethylamine, provided XV in an 88% yield. The best yields are obtained in this reaction when care is taken to exclude other nucleophilic species that could compete with the weakly-nucleophilic phosphonate anion.

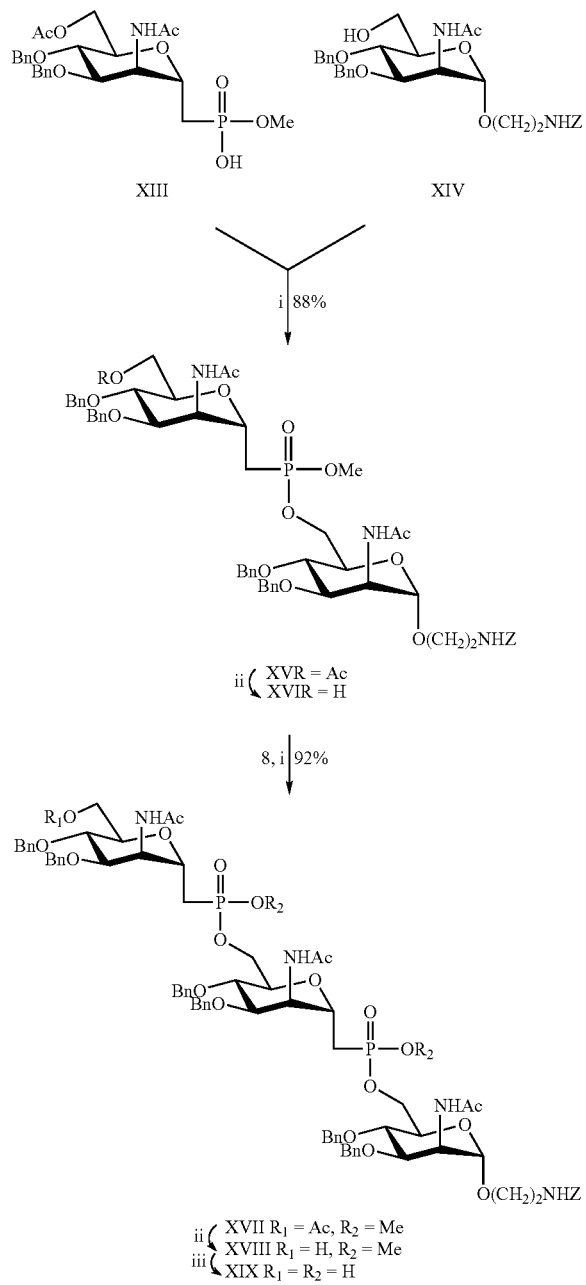

Key: i) (pClPh)₃P, DIAD, Et₃N, THF; ii) KOH, MeOH; iii) PhSH, DBU, CH₃CN.

Using the Mitsunobu conditions described above the yield in the trimer formation was found to be comparable and even higher than in the dimer formation. The dimer XV was transformed into a new acceptor (→XVI) by deacetylation. The modified Mitsunobu reaction between XVI and XIII then afforded the trimer XVII in a 92% yield. The identity of the products was proven by MS and NMR, the latter partly complex due to diastereomers phosphonate that result from the chirality of the phosphorus. Compound XVII was deacetylated, which creates a new acceptor XVIII which can be attached to another elongation monomer. After this and subsequent removal of the phosphonate methyl ester, the chirality of the phosphorus center was destroyed, and the NMR data for compound XIX reflected the absence of phosphorus diastereomers.

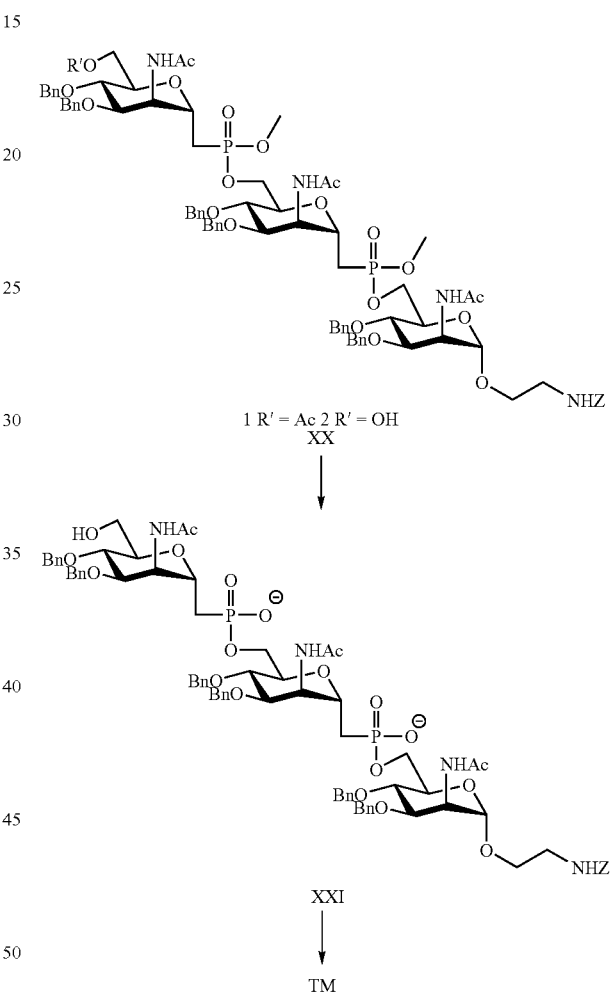

It was also found that by prolonging the exposure of the mixture of the acceptor XIV and elongation monomer XIII to the Mitsunobu conditions, and in the presence of some excess XIII, the reaction provides longer monomers. Thus under the reaction conditions, cleavage of the C-6 acetyl group from an incorporated elongation monomer occurs in situ at some rate; and this provides a new acceptor molecule. Thus to some degree, for example, conversion of XVI to XVI occurs by prolonged exposure to the Mitsunobu reaction, and under those conditions in the presence of excess XIII, it forms XVII; and so forth, to produce higher oligomers. This reaction thus provides a way to make oligomers containing multiple mannose units in protected form without requiring a stepwise deprotection/isolation process, and allows the synthesis of immunogenic oligosaccharides of the invention having a distribution of sizes. In some embodiments, this has been shown to provide primarily tetra- and penta-mannose oligosaccharides, with minor amounts of longer oligomers. It thus provides a highly efficient way to synthesized longer oligomeric compounds within the invention.

The invention also provides a simple and improved synthesis of 2-azido-2-deoxy-D-mannopyranose from a readily available precursor, 1,3,4,6-tetra-O-acetyl-glucopyranose, as illustrated in Scheme 5. This intermediate is useful for the synthesis of many of the mannose units of the present invention.

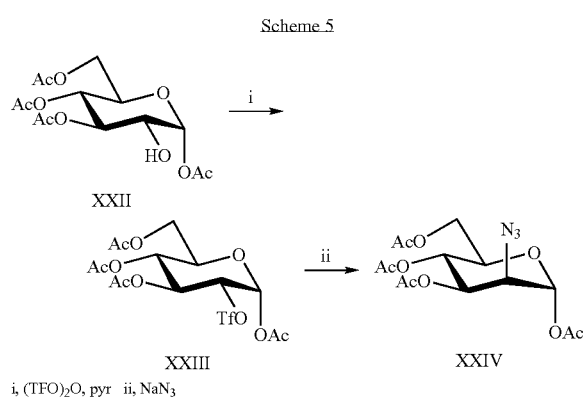

In an attempt to synthesize a protected 2-azido mannose compound, 1,3,4,6-tetra-O-acetyl glucopyranose was converted into its 2-O-triflate using triflic anhydride, and the triflate was treated with $NaN_3$. According to TLC and MALDI-TOF-ms, the 2-azido product forms in a high yield, but apparently it substantially decomposes during a typical aqueous workup, and the isolated yield was only 20%. However, when the reaction was worked up without using water, the yield was sharply improved. Thus most of the DMF used as the solvent for the displacement was removed under reduced pressure, and the residue was transferred to a dried column containing a slurry of pre-dried silica in dry toluene. The product was eluted using a gradient of increasing ethyl acetate in toluene. Once purified, the product was relatively stable. The 1,3,4,6-tetra-O-acetyl glucopyranose starting material is very easy to synthesize in large scale in a one pot synthesis from glucose, and the intermediate triflate was obtained using standard conditions in 97% yield. The isolated yield from the inversion as mentioned is strongly dependent on how water free the workup is: exclusion of water by using pre-dried glassware and pre-dried silica as described above is necessary for optimum yield. By minimizing exposure to moisture during work-up and during silica gel chromatography, reproducible yields of 60% or better were obtained.

The tetraacetate product shows some tendency to decompose during storage. However, once converted to its 1-ethylthio glycoside by treatment with $EtSH/BF_3$-$Et_2O$ it was quite stable. It was next treated with alkoxide to remove the acetate groups, as shown in Scheme 6, and the primary hydroxyl was selectively protected with a t-butyldimethylsilyl (TBS) group. The two secondary hydroxyls were protected as benzyl esters, but a variety of different protecting groups can be used here and in many other steps throughout this process. The —SEt group was then replaced by a linker, which can be used to conjugate the final oligosaccharide to a protein. Alternatively, it could be used to attach the acceptor monomer to a solid support while the oligosaccharide is assembled. In this case, a protected aminoethyl group was introduced at the anomeric position; however, a wide variety of linking groups that are suitable for conjugating the oligosaccharide may be used, and those of skill in the art can readily select and use others.

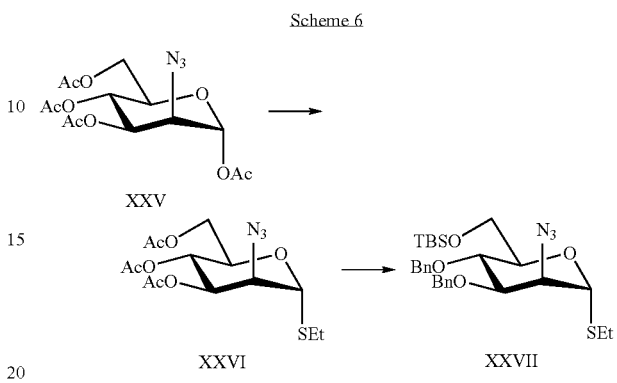

The dimer can be used as an immunogen without further elongation, or longer oligomers can be prepared and used. For both the dimer and the trimer, the acetyl group at C6 is removed by standard hydrolysis. The methyl esters of the phosphonate were cleaved using 1,8-diaza-7-bicyclo[5.4.0]undecene (DBU) as the base along with phenyl mercaptan, to effect a nucleophilic demethylation. The benzyl ethers were then cleaved along with the benzyloxycarbonyl via a standard reductive hydrogenation, using palladium on activated charcoal as the catalyst. To get the reaction to go to completion, aqueous HCl was added so that the resulting amine is protonated to form the hydrochloride, which reduces its tendency to poison the catalyst.

The oligosaccharides of the invention can be administered to a mammal to elicit an immunogenic response; they may be used as described above, typically after at least partial deprotection. They may also be partly or entirely acetylated to broaden the spectrum of the immune response elicited. The CPS of the target organism is substantially acetylated on the C-3 hydroxyl; thus the flexibility of the present synthetic method makes it possible to prepare compounds containing one or more acetyl groups, and particularly to prepare dimers, trimers, and higher oligomers that are partially or entirely acetylated at C-3 hydroxyl, or mixtures of these.

Instead of, or in addition to, using phosphonate linkages to stabilize the phosphodiester, as described above it is possible to stabilize the phosphodiester to a useful degree by incorporating an azide group as the C-2 aza substituent during synthetic manipulations up to and optionally during the step of conjugating the oligosaccharide to a protein. This stabilization is inductive, but is adequate to improve the working stability of the intermediates over that of the corresponding NHAc compounds. Once the azide has served its purpose, it can be reduced with nickel borohydride and acetylated with acetic anhydride or similar acylating agents as described herein. The oligomeric compounds of the invention can thus incorporate phosphodiester linkages to some degree as described above, and the phosphodiesters can be incorporated by typical methods and those described herein.

To have the option to get both the target molecules with or without acetates, the protecting group strategy was based on acetates as permanent protecting groups. To stabilize the anomeric phosphodiester linkage azide was used as a precursor for the acetamido group as far as possible into the synthesis, as illustrated in Scheme 7 below. The electron withdrawing properties and the lack of participating effect of the azide strongly protects the linkage. And after initial problems with the use of dimethoxy trityl as a temporary protecting group for the 6-OH we used TBDMS (t-butyl dimethylsilyl ether, sometimes referred to as TBS). The TBDMS ethers were cleaved off in good yield with minimal problems due to acetyl migration or cleavage of the labile phosphodiester linkage. TBAF which was successfully used for deprotection of TBDMS ethers in the previous C-phosphonate synthesis could not be used due to acetyl migration so the rather slow (especially when having azide in pos 2) but reliable if TREAT-HF was used.

Donor 1 was synthesized by first hydrolyzing the thioglycoside using a glycosylation with NIS as promoter and water as acceptor at −20° C. The desired alpha-anomer was obtained exclusively in 82% yield. If the reaction is carried out at room temperature, a large percentage of beta is formed. This compound was then phosphonylated using $PCl_3$/imidazole giving XXX in 97% yield. Thus, the invention includes preparing alpha-anomers at low temperatures such as lower

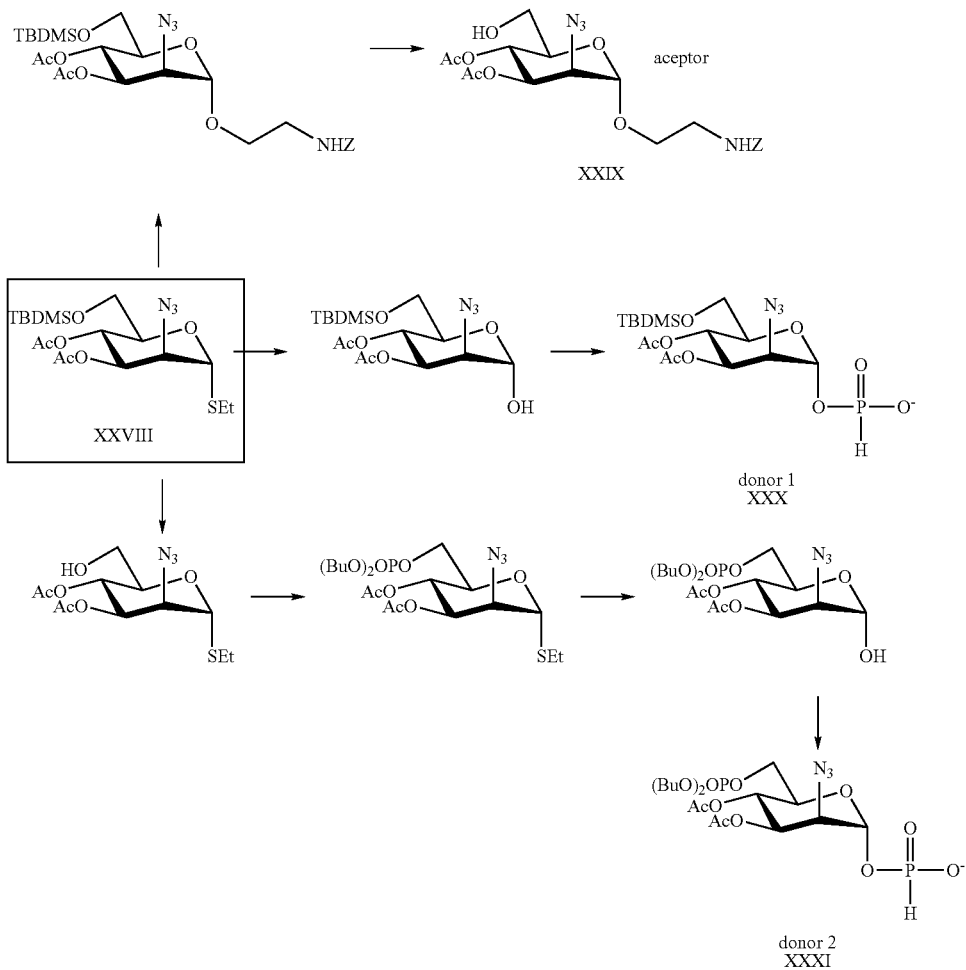

Scheme 7

For an efficient modular synthesis, three monosaccharide building blocks were needed; a spacer equipped starting monomer 6-OH acceptor, an alpha-H-phosphonate elongating monomer with temporary 6-OH protection (donor 1) and a terminating alpha-H-phosphonate monomer phosphorylated in the primary position (donor 2). To achieve the target molecules with a phosphate at C-6, as exemplified here as trimeric oligosaccharides, a donor containing a dibenzyl protected phosphate was used because an attempt at post-linkage modification of the C-6 hydroxyl using amidite chemistry was unsuccessful.

To simplify the synthesis all three units were synthesized from the same precursor, XXVIII, as shown in Scheme 7 above. The starting material was synthesized using conventional methods. To make the acceptor, it was coupled to a benzyloxycarbonyl protected ethanolamine spacer in 86% yield and the TBDMS-ether removed using TREAT-HF to give the acceptor XXIX in 97% yield.

than room temperature, preferably lower than 0° C., more preferably lower than −10° C., such as −20° C. or less.

To synthesize donor mannose units having the H-phosphonate, which is useful to add mannose units linked to an oligosaccharide of the invention through a phosphodiester linkage, the TBDMS-ether was cleaved in 75% yield and the hydroxyl was phosphorylated using amidite chemistry to give a benzyl protected phosphate at C-6 (67%). The ethyl thio glycoside was hydrolyzed in the same fashion as for donor 1 by coupling to water (79%) and then phosphonylated to give the H-phosphonate donor mannose unit XXXI in 92% yield.

The coupling of the elongating monomer to the acceptor was carried out using conventional H-phosphonate chemistry with a pivaloyl chloride-promoted condensation as illustrated in Scheme 8 below. The H-phosphonate diester was oxidized using elemental iodine and water to provide the phosphate diester. The dimer was obtained in a good yield (96%).

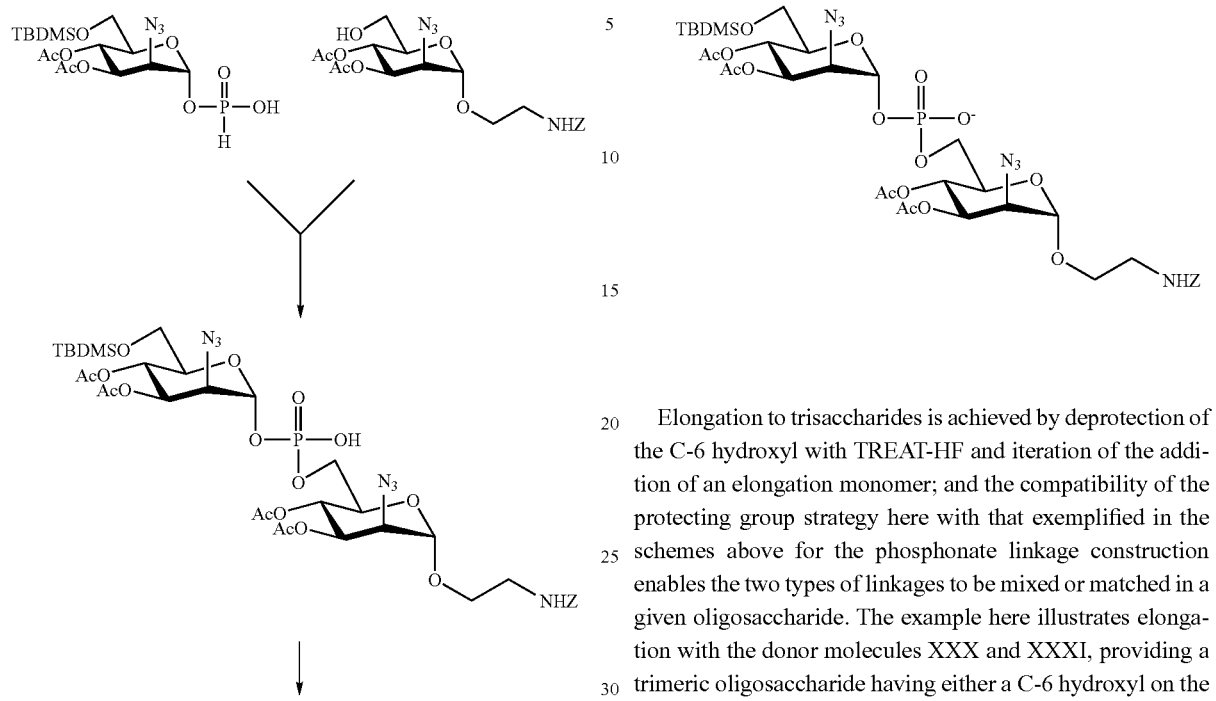

Elongation to trisaccharides is achieved by deprotection of the C-6 hydroxyl with TREAT-HF and iteration of the addition of an elongation monomer; and the compatibility of the protecting group strategy here with that exemplified in the schemes above for the phosphonate linkage construction enables the two types of linkages to be mixed or matched in a given oligosaccharide. The example here illustrates elongation with the donor molecules XXX and XXXI, providing a trimeric oligosaccharide having either a C-6 hydroxyl on the last mannose unit, or a C-6 O-phosphate in that position.

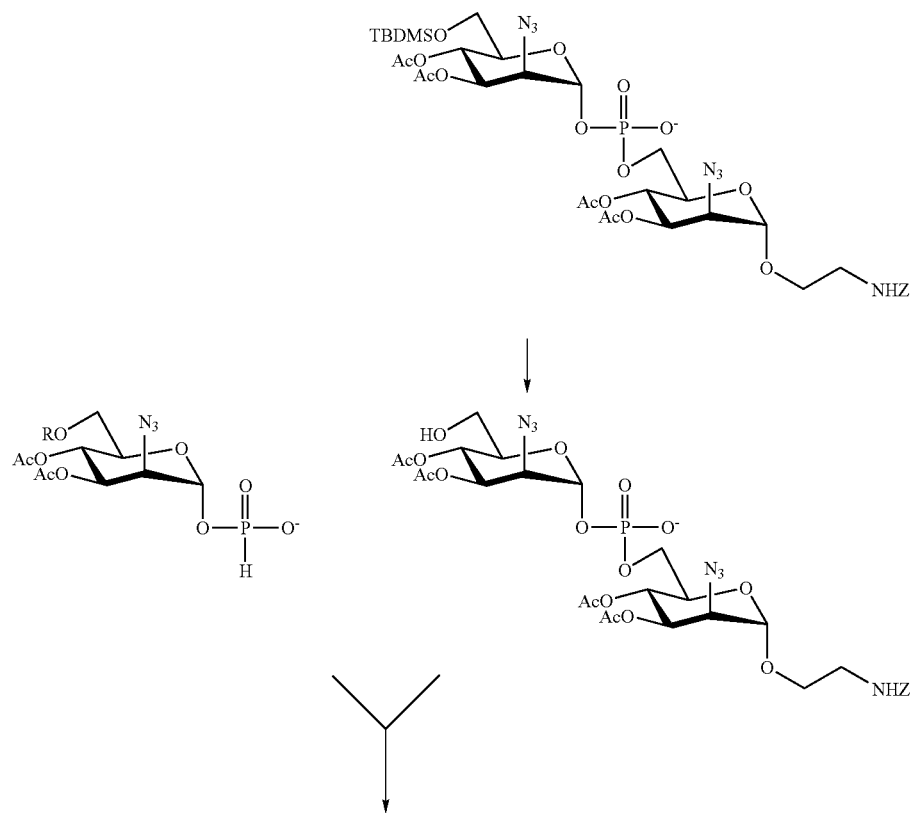

-continued

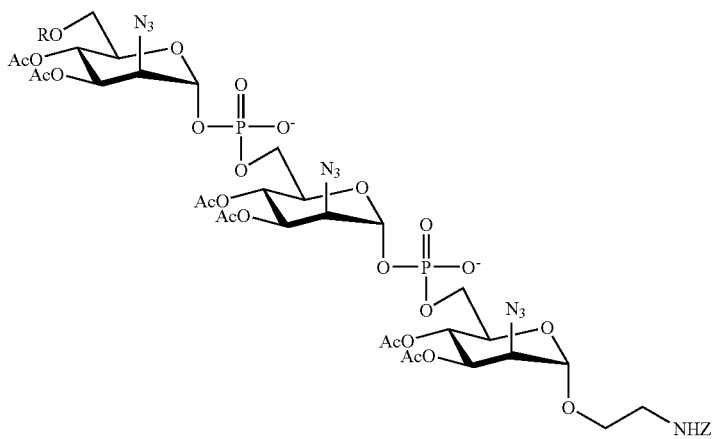

Where R is either OH or dibenzyl phosphate

To obtain the trisaccharide, the TBDMS-ether on the disaccharide was removed in 91% yield, again using TREAT-HF. Subsequent coupling of the two donors using the same conditions as employed for the coupling to the disaccharide, resulted in the formation of the two trisaccharides in 62% and 59% yield respectively. The yields obtained during the second or subsequent couplings were lower than that obtained from the first coupling step, as observed by Pozsgay, et al. (See, A. Berkin, B. Coxon and V. Pozsgay, *Chem. Eur. J.,* 2002, 8, 4424.) Thus in preferred embodiments at least some of the linkages between adjacent mannose units in an oligosaccharide typically comprise a phosphonate instead of a phosphodiester.

The azides on both forms of the oligomers of the invention may also comprise an additional phosphate in protected form at R' or its equivalent position, e.g., the $R^6$ group in dimers and trimers of the phosphonate oligomers. This is optionally introduced because the terminal mannose units in the natural CPS may be phosphorylated, and the corresponding phosphoryl group can be introduced as a dibenzyl phosphate ester using conventional chemistry. The benzyl groups can then be removed along with the benzyl ethers at C-3 and/or C-4, for example, or along with reductive cleavage of a benzyloxycarbonyl group that may be used to protect an amine group in the spacer moiety at position 1 of the first mannose unit. The benzyl phosphonate does not interfere with the other reactions needed to produce the oligomers. For example, the azides in certain compounds containing this group were successfully reduced to amines using sodium borohydride and a catalytic amount of nickel chloride hexahydrate, and the resulting amines were acetylated with acetic anhydride giving the corresponding aminoacyl derivatives. This reaction proceeded in 89% yield when the terminal group on a mannose unit in a trimeric phosphodiester-linked compound was OTBDMS, and in 64% yield when that terminal group was a dibenzyl phosphate.

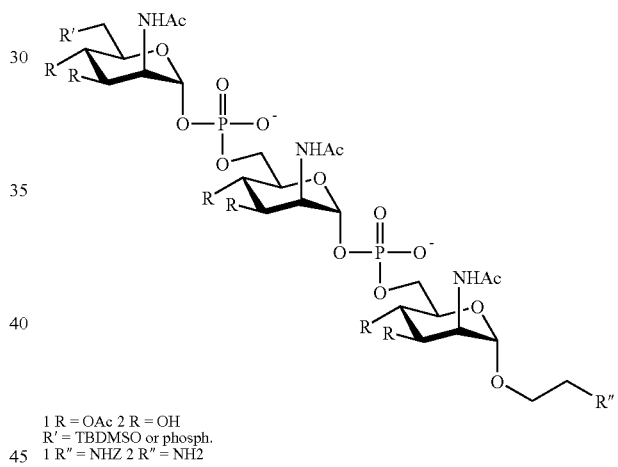

1 R = OAc 2 R = OH
R' = TBDMSO or phosph.
1 R" = NHZ 2 R" = NH2

The two trisaccharides were deprotected in a different order. To achieve the target molecules 1 and 2 first the Z-group was deprotected using reductive hydrogenation (83%). To avoid problems with degradation of the phosphodiester linkage during reductive hydrogenation, basic ion exchange resin were added to the mixture with good result. The TBDMS-ether was removed again using TREAT-HF giving 1 in 85% yield. The acetate was cleaved under standard sodium methoxide/methanol conditions. For target molecule 3 the Z was removed in the same way as in the previous deprotection of 1 (85%) and to achieve 4 the acetates were removed (80%) prior to the reductive hydrogenation (64%).

The methods described in the schemes above may also be used to make compounds having a C-phosphonate, such as those compounds of formula (1) or (1'), described herein.

Use of the Compounds as Antigens

The oligosaccharides prepared by the above methods are immunogenic and are useful to elicit an immune response that protects against infection by *N. meningitidis*, as in a vaccine. In particular, an oligosaccharide having the structure shown in formula (1) above is capable of eliciting an immunogenic response if administered to a mammal, and therefore administering composition comprising an oligosaccharide of formula (1) is useful to elicit the formation of antibodies and/or to provide an immunogenic response and to provide at least partial resistance or partial immunity to infection by *N. meningitidis* A. The antibodies and/or immunogenic response provide protection against infection by *N. meningitidis* A. Compounds comprising the moiety in formula (1), especially those wherein W is $CH_2$ or O, X is O, and Az is NHAc, are useful as vaccine components, as are compounds of formula (4).

These compounds are especially useful when conjugated to a protein, and optionally the Z group of formula (1) may be used to link the oligosaccharide of formula (1) to a protein. Likewise, in other compounds of the formula, the corresponding group at C-1 of the first mannose unit in an oligosaccharide of the invention may be a moiety capable of being used to conjugate the compound to a carrier protein to improve its immunogenic properties. Notwithstanding the option of linking through Z, however, the compounds of the invention and specifically compounds comprising the structure in formula (1) or formula (4) can be linked by other means to a carrier protein, such as through one or more of the hydroxyl groups or through an acyl group attached in place of an acetyl group on one of the acetylamines on one of the mannose units. Such alternative conjugation mechanisms are within the scope of the invention, as long as the C-1 (anomeric) center of the oligosaccharide remains in the desired alpha configuration. Preferably such oligosaccharides comprise at least one phosphonate linkage between two mannose units.

Accordingly, an aspect the present invention is directed to vaccines which contain as an active ingredient an immunogenically effective amount of an immunogenic oligosaccharide as described herein. The oligosaccharide(s) may be introduced into a host, including humans, either alone or linked to a carrier such as a protein or as a homopolymer or heteropolymer of mannose units or of other saccharides. In some embodiments, they are used as glycoconjugates, and the protein to which the oligosaccharide is conjugated is selected for its ability to enhance the immunogenic response to the oligosaccharide antigen: proteins that have elicited an immune response in the mammal to be treated are sometimes preferred. The glycoconjugates have the advantage of increased immunological activity and the additional ability to induce antibodies and/or CTLs that react with different antigenic determinants of the virus or tumor cells.

The immunogenic compositions of the invention include at least one compound of the invention, and may optionally include more than one such compound. Thus it is sometimes desirable to mix together two or more compounds of the invention to broaden the immunogenic response elicited. For example, it is often desirable to combine a compound wherein $R^3$ is H with a compound wherein $R^3$ is Ac, since the CPS of the target organism is partially, but not fully, acetylated at this position. Thus in some embodiments, the immunogenic compositions comprise at least two and optionally three or more of such immunogenic compounds and/or protein conjugates of such compounds.

Similarly, the carrier proteins may influence the immunogenic response and even affect the precise nature of the antibodies that result from treatment of a mammal with one or more compounds of the invention when delivered as glycoconjugates. Therefore, the invention includes compositions that comprise more than one carrier protein, whether or not they comprise two or more oligosaccharides.

Useful carrier proteins are well known in the art, and include, e.g., thyroglobulin, albumins such as human serum albumin, tetanus toxoid, diphtheria toxoid, polyamino acids such as poly(lysine:glutamic acid), influenza, hepatitis B virus core protein, hepatitis B virus recombinant vaccine and the like. Bacterial outer membrane proteins such as, outer membrane complex c (OMPC), porins, transferrin binding proteins, pneumolysis, pneumococcal surface protein A (PspA), or pneumococcal adhesin protein (PsaA), could also be used. Other proteins, such as ovalbumin, keyhole limpet hemocyanin (KLH), bovine serum albumin (BSA) or purified protein derivative of tuberculin (PPD) may also be used as carrier proteins. Carrier proteins are preferably proteins that are non-toxic and non-reactogenic and obtainable in sufficient amount and purity.

Carrier proteins should be amenable to standard conjugation procedures. In a preferred embodiment of the present invention diphtheria toxin purified from cultures of *Corynebacteria diphtheriae* and chemically detoxified using formaldehyde is used as the carrier protein. In other embodiments, CRM197 was used.

Methods for attaching an oligosaccharide to a carrier protein are conventional, and a skilled practitioner can create glycoconjugates comprising the compounds of the invention using conventional methods. Guidance is also available in many publications and in, for example, U.S. Pat. Nos. 4,356,170; 4,619,828; 5,153,312; 5,422,427; and 5,445,817.

In one such embodiment, using 2-aminoethoxy as the spacer moiety at C-1 of the first mannose unit and a phosphodiester linkage, and using either suberic acid or squarate as the bi-functional reagent to connect the spacer moiety to the carrier protein, and using CRM197 as the carrier protein, glycoconjugates were prepared. According to MALDI-TOF mass spectral analysis, these conjugates contained about five oligosaccharide molecules, on average, per carrier protein molecule. However, oligosaccharide:carrier protein ratios of about 0.1 to about one on a molar ratio are often desirable, and molar ratios of about 1-30:1 or about 1-10:1 are within the scope of the invention, regardless of which carrier protein is utilized. The ratio of oligosaccharide to carrier protein may also be characterized as a weight ratio between the two; ratios of about 1:1 to 1:500 are often preferred. The precise ratio depends upon the ratio of the molecular weight of the protein and the oligosaccharide; for smaller oligosaccharides, a weight ratio of 1:5 to 1:200 is sometimes used.

After conjugation of the capsular polysaccharide to the carrier protein, the polysaccharide-protein conjugates may be purified (enriched with respect to the amount of polysaccharide-protein conjugate) by a variety of techniques. One goal of the purification step is to remove the unbound polysaccharide from the polysaccharide-protein conjugate. One method for purification, involving ultrafiltration in the presence of ammonium sulfate, is described in U.S. Pat. No. 6,146,902. Alternatively, conjugates can be purified away from unreacted protein and polysaccharide by any number of standard techniques including, inter alia, size exclusion chromatography, density gradient centrifugation, hydrophobic interaction chromatography or ammonium sulfate fractionation. See, e.g., Anderson, P. W., et al., *J. Immunol.* (1986) 137:1181-1186. See also Jennings, H. J., et al., *J. Immunol.* (1981) 127:1011-1018.

The vaccines of the invention comprise at least one immunogenic compound of the invention, and can also contain a physiologically tolerable (acceptable) diluent such as water, phosphate buffered saline, or saline, and further typically include an adjuvant. U.S. Pat. No. 6,869,607 provides nonionic adjuvants for protein-conjugated immunogens and discusses other suitable adjuvants, and is incorporated by reference for its description of such adjuvants. Materials such as incomplete Freund's adjuvant, aluminum phosphate, aluminum hydroxide or alum, aluminum sulfate, aluminum phosphate, and combinations thereof are materials well known in the art as adjuvants. Also useful are BAY, DC-chol, pcpp, monophosphoryl lipid A, CpG, QS-21, cholera toxin, and formyl methionyl peptide, as well as emulsion formulations including MF59, SAF, squalane, Tween, pluronic-blocked polymer L121, and components such as monophosphorylipid A, trehalose dimycolate, and cell wall skeleton. Cytokines such as IL-1, IL-2, IL-4, IL-5, IL-6. IL-7, IL-12, interferons, and tumor necrosis factor (TNF) may also be included. In some preferred embodiments of the invention, alum is used as the adjuvant.

Upon immunization with a composition as described herein, via injection, aerosol, oral, transdermal or other route, the immune system of the host responds to the vaccine by producing large amounts of CTLs specific for the desired antigen, and the host becomes at least partially immune to later infection by the *N. meningitidis* pathogen.

The vaccines and pharmaceutical compositions of the invention are intended for parenteral, topical, oral or local administration. Preferably, they are administered parenterally, e.g., intravenously, subcutaneously, intradermally, or intramuscularly. Thus, the invention provides compositions for parenteral administration which comprise a solution of the immunogenic moiety dissolved or suspended in an acceptable carrier, preferably a primarily aqueous carrier. A variety of aqueous carriers may be used, e.g., water, buffered water, 0.8% saline, 0.3% glycine, hyaluronic acid and the like. These compositions may be sterilized by conventional sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. The preparation of such pharmaceutical compositions is within the ordinary skill in the art, and may be guided by standard reference books such as *Remington's Pharmaceutical Science*, latest ed., which is incorporated herein by reference.

In preferred embodiments, a vaccine composition comprising at least one moiety of formula (1) or formula (4) in a substantially aqueous mixture is formulated as a sterile, pyrogen-free buffered saline or phosphate-containing solution, which may include a preservative or may be preservative free. Suitable preservatives include benzyl alcohol, parabens, thimerosal, chlorobutanol, and benzalkonium chloride, for example. The solution is preferably approximately isotonic, and its tonicity may be adjusted with agents such as sodium tartrate, sodium chloride, propylene glycol, and sodium phosphate.

The concentration of the immunogenic oligosaccharides of the invention in the pharmaceutical formulations can vary widely, i.e., from less than about 0.1%, usually at or at least about 0.1% to as much as 20% to 50% or more by weight, and will be selected primarily by fluid volumes, viscosities, etc., and in accordance with the particular mode of administration selected. A human unit dose form of the compounds and composition is typically included in a pharmaceutical composition that comprises a human unit dose of an acceptable carrier, preferably an aqueous carrier, and is administered in a volume of fluid that is known by those of skill in the art to be used for administration of such compositions to humans, and is adjusted according to commonly understood principles for a particular subject to be treated. Thus in one embodiment, the invention provides a unit dosage of the vaccine components of the invention in a suitable amount of an aqueous solution, such as 0.1-3 ml, preferably 0.2-2 mL.

The immunogens of the invention may also be administered via liposomes, which can serve to concentrate them in a particular tissue, such as lymphoid tissue, or to enhance their activity or delivery characteristics. A variety of methods are available for preparing liposomes, as described in, e.g., Szoka, et al., *Ann. Rev. Biophys. Bioeng*. (1980) 9:467, U.S. Pat. Nos. 4,235,871, 4,501,728, 4,837,028, and 5,019,369.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and a unit dosage of an active ingredient, that is, one or more compounds of the invention, whether conjugated to a protein or not.

For aerosol administration, the immunogenic compounds are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

Amounts effective for this use will depend on, e.g., the oligosaccharide composition, whether it is conjugated to a protein, the manner of administration, the weight and general state of health of the patient, and the judgment of the prescribing physician, but generally range for the initial immunization (that is for a prophylactic administration) from about 1.0 μg to about 5,000 μg of peptide for a 70 kg patient, (e.g., 1.0 μg, 1.5 μg, 2.0 μg, 2.5 μg, 3.0 μg, 3.5 μg, 4.0 μg, 4.5 μg, 5.0 μg, 7.5 μg, 10 μg, 12.5 μg, 15 μg, 17.5 μg, 20 μg, 25 μg, 30 μg, 35 μg, 40 μg, 45 μg, 50 μg, 75 μg, 100 μg, 250 μg, 500 μg, 750 μg, 1,000 μg, 1,500 μg, 2,000 μg, 2,500 μg, 3,000 μg, 3,500 μg, 4,000 μg, 4,500 μg or 5,000 μg). The actual dose administered to a subject is often determined according to an appropriate amount per kg of the subject's body weight. For example, an effective amount may be about 0.1 to 5 μg/kg body weight.

A primary dose may optionally be followed by boosting dosages of from about 1.0 μg to about 1,000 μg of peptide (e.g., 1.0 μg, 2.0 μg, 2.5 μg, 3.0 μg, 3.5 μg, 4.0 μg, 4.5 μg, 5.0 μg, 7.5 μg, 10 μg, 12.5 μg, 15 μg, 17.5 μg, 20 μg, 25 μg, 30 μg, 35 μg, 40 μg, 45 μg, 50 μg, 75 μg, 100 μg, 250 μg, 500 μg, 750 μg, 1,000 μg, 1,500 μg, 2,000 μg, 2,500 μg, 3,000 μg, 3,500 μg, 4,000 μg, 4,500 μg or 5,000 μg) pursuant to a boosting regimen over weeks to months depending upon the patient's response and condition by measuring specific T cell activity in the patient's blood.

The immunogenic compositions comprising a compound of the invention are suitable for use in adult humans or in children, and in some embodiments they are administered to young children, who are at risk for contracting meningitis caused by *N. meningitidis*. Optionally such a composition may be administered in combination with other pharmaceutically active substances, and frequently it will be administered in combination with other vaccines as part of a childhood vaccination program. Compositions for administration may beneficially include other types of immunogenic compounds such as glycoconjugates that elicit an immune response to provide protection against other meningitis pathogens, also. Thus in some embodiments, the vaccine compositions of the invention include at least one antigen derived from another Meningitidis serotype, typically from at least one of serotypes A, B, C, W135, and Y. Preferred embodiments often comprise antigens to at least one and often two or all of serotypes C, Y and W135 in combination with at least one and optionally two or more compounds comprising an oligosaccharide of the present invention.

EXAMPLES

The following examples illustrate certain embodiments of the invention, but in no way limit its scope. Other variations of the exemplified reactions and formulations will be apparent to those skilled in the art, and are also within the scope of the invention. For example, changing the order of steps, or modifying the protecting group strategy selected often represent typical choices made by the ordinary practitioner. The numbering of compounds in the following section does not correlate to the numbering of compounds in the reaction schemes provided above, and is provided for the convenience of the reader.

General Methods.

TLC was carried out on Merck precoated 60 $F_{254}$ plates using AMC (ammonium molybdate-cerium(IV) sulfate-10% sulphuric acid 100 g:2 g:2 L) or 8% $H_2SO_4$ for visualization. Column chromatography was performed on silica gel (0.040-0.063 mm, Amicon) or reversed phase gel (C18 60A 40-63 μm). NMR spectra were recorded in $CDCl_3$ (external $Me_4Si$, δ=0.00) or $D_2O$ (internal acetone $^{13}C$ δ=30.89, $^1H$=2.22) at 25° C. on a Varian 300 MHz or 400 MHz instrument. Organic solutions were concentrated at 30° C. under reduced pressure.

Example 1

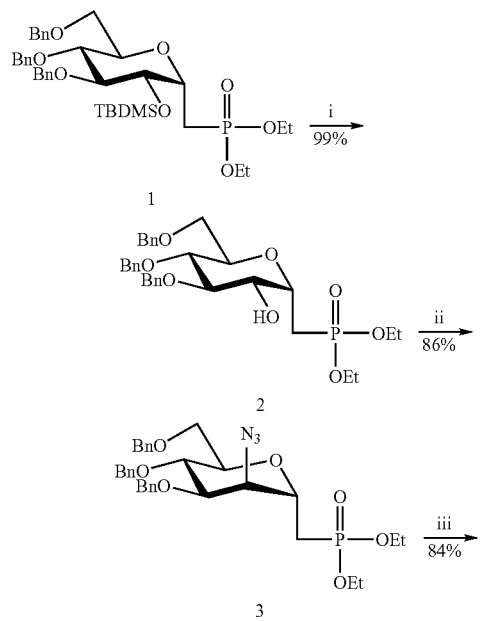

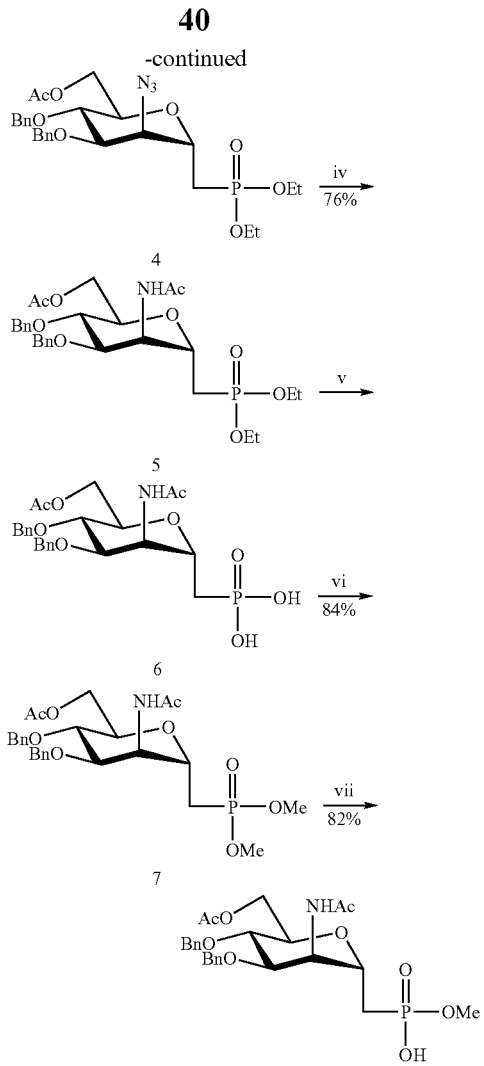

Key: i) TBAF; ii) Ph$_3$P, DIAD, DPPA, THF; iii) HOAc, Ac$_2$O, H$_2$SO$_4$; iv) a. NaBH$_4$, NiCl$_2$x6H$_2$O, b. Ac$_2$O; v) Me$_3$SiBr; vi) MeC(OMe)$_3$, HOAc; vii) PhSH, Et$_3$N.

Diethyl C-(3,4,6-tri-O-benzyl-α-D-glucopyranosyl)methanephosphonate (2) TBAF (2.6 g 1.3 eq) was added to a solution of diethyl C-(2-O-tertbutyldimethylsilyl-3,4,6-tri-O-benzyl-α-D-glucopyranosyl)methanephosphonate (1, 5.36 g, 7.7 mmol) in THF (150 mL). After 20 min the solvent was removed under reduced pressure and the product was purified by silica gel column chromatography to give 2 (4.44 g, 7.6 mmol, 99%).

Diethyl C-(2-azido-3,4,6-tri-O-benzyl-2-deoxy-α-D-mannopyranosyl)methanephosphonate (3). DIAD (2.4 mL, 12.4 mmol) was added dropwise to a cooled (−5° C.) solution of Ph$_3$P (3.1 g, 11.7 mmol) in THF (50 mL). After 30 min, a solution of 2 (5.57 g, 9.5 mmol) in THF (20 mL) was added. After an additional 10 min, diphenyl phosphorazidate (DPPA; 2.4 mL, 11.31 mmol) was added and the reaction mixture was allowed to attain rt. After stirring overnight, the solvent was evaporated and the residue was purified by silica gel chromatography to give 3 (5.0 g, 8.2 mmol, 86%) as a colorless oil. $^{13}$C-NMR (CDCl$_3$) 138.17, 137.92, 137.38, 128.6-127.7, 78.2, 74.3, 73.9, 73.7, 73.5, 72.4, 69.5, 68.8, 62.2, 62.1, 62.0, 61.9, 61.0, 60.9, 27.9 (d, J=141 Hz), 16.5, 16.4; $^{31}$P-NMR (CDCl$_3$) 27.9.

Diethyl C-(6-O-acetyl-2-azido-3,4-di-O-benzyl-2-deoxy-α-D-mannopyranosyl)methanephosphonate (4). Compound 3 (3.2 g, 5.2 mmol) was dissolved in HOAc/Ac$_2$O (1:1, 32 mL). Ten drops of 1% H$_2$SO$_4$ in Ac$_2$O was added. After stirring overnight the mixture was poured into a separation funnel containing ice and CH$_2$Cl$_2$. The organic phase was separated, filtered through a plug of silica and concentrated. The residue was purified by column chromatography to give 4 (2.48 g, 4.4 mmol, 84%). $^{13}$C-NMR (CDCl$_3$) 170.41, 137.41, 136.95, 128.34-127.75, 77.77, 77.60, 74.01, 73.39, 72.17, 71.89, 69.26, 62.47, 61.82, 61.73, 60.50, 60.37, 27.57 (d, J=141 Hz), 20.59, 16.27, 16.19; $^{31}$P-NMR (CDCl$_3$) 27.50; $[\alpha]_D$+37 (c 1.0, CHCl$_3$).

Diethyl C-(6-O-acetyl-2-acetamido-3,4-di-O-benzyl-2-deoxy-α-D-mannopyranosyl)methanephosphonate (5). To a stirred solution of 4 (2.50 g, 4.45 mmol) in MeOH (125 mL) a catalytic amount of NiCl$_2$×6H$_2$O was added followed by portions of NaBH$_4$ (in total 0.34 g, 8.9 mmol) every 10 min until no starting material was observed on TLC (system). Ac$_2$O (3 mL) was added after 50 min and the reaction mixture was diluted with toluene, filtered through a plug of silica and concentrated. The residue was purified by silica gel chromatography to give 5 (1.95 g, 3.4 mmol, 76%). $^{13}$C-NMR (CDCl$_3$) 170.4, 169.7, 137.3, 137.0 remaining aromatic C 128.5-127.7, 75.3, 72.6, 72.4, 72.1, 72.0, 67.1, 61.91, 61.8, 61.8, 61.3, 61.2, 48.8, 48.6, 28.5 (d, J=142 Hz), 23.0, 20.6, 16.3, 16.2, 16.1; $^{31}$P-NMR (CDCl$_3$) 29.5.

Dimethyl C-(6-O-acetyl-2-acetamido-3,4-di-O-benzyl-2-deoxy-α-D-mannopyranosyl) methanephosphonate (7). To a solution of 5 (0.25 g, 0.43 mmol) in dry CH$_2$Cl$_2$ (5 mL) bromotrimethylsilane (0.28 mL, 2.2 mmol, 5 eq) was added at rt. After the addition was complete, the mixture was stirred at rt for 1 h. The solution was cooled to 0° C. and Et$_3$N (1 mL) was added followed by addition of water (1 mL). After 10 min the solvents were removed under reduced pressure and the residue desalted by RP-chromatography (water-water/MeOH 1:1). The product C-(6-O-acetyl-2-acetamido-3,4-di-O-benzyl-2-deoxy-α-D-mannopyranosyl)methanephosphonate (6) was methylated without further purification. To the product from the reaction described above were added AcOH (5.5 mL) and trimethylorthoacetate (11.5 mL). The mixture was heated at reflux for 30 min and then concentrated. The residue was purified by silica gel chromatography to give 7 (0.20 g, 0.36 mmol, 84% over two steps). (The reaction has to be monitored carefully and stopped exactly when the reaction is completed, otherwise the result is a mixture of the wanted product and the product where the 6-OAc is deprotected.) $^{13}$C-NMR (CDCl$_3$) 170.6, 170.0, 137.4, 137.1 remaining aromatic C 129.9-127.4, 75.3, 73.0, 72.5, 72.4, 72.0, 66.7, 61.8, 52.9, 52.8, 52.2, 52.1, 49.0, 48.7, 28.0 (d, J=1142 Hz), 23.2, 20.8; $^{31}$P-NMR (CDCl$_3$) 31.6.

Methyl C-(6-O-acetyl-2-acetamido-3,4-di-O-benzyl-2-deoxy-α-D-mannopyranosyl)methanephosphonate (8). To a solution of 7 (1.35 g, 2.46 mmol) in THF (2 mL) were added thiophenol (1.0 mL, 9.83 mmol) and Et$_3$N (2.0 mL, 14.7 mmol). After 48 h the reaction mixture was directly put on a silica gel column and first eluted with toluene and then with CHCl$_3$/MeOH 9:1 containing 1.5% TEA to give 8 (1.28 g, 2.01 mmol, 82%). $^{13}$C-NMR (CDCl$_3$) 169.5, 169.1, 137.1, 137.1, remaining aromatic C, 127.4-126.7, 75.0, 72.6, 72.1, 71.6, 71.2, 62.0, 51.7, 50.6, 50.5, 49.5, 28.6 (d, J=129 Hz), 22.4, 22.3, 19.9; $^{31}$P-NMR (CDCl$_3$) 20.4; $[\alpha]_D$+15 (c 1.0, CHCl$_3$).

The following scheme applies to the remainder of Example 1 and Example 2-6.

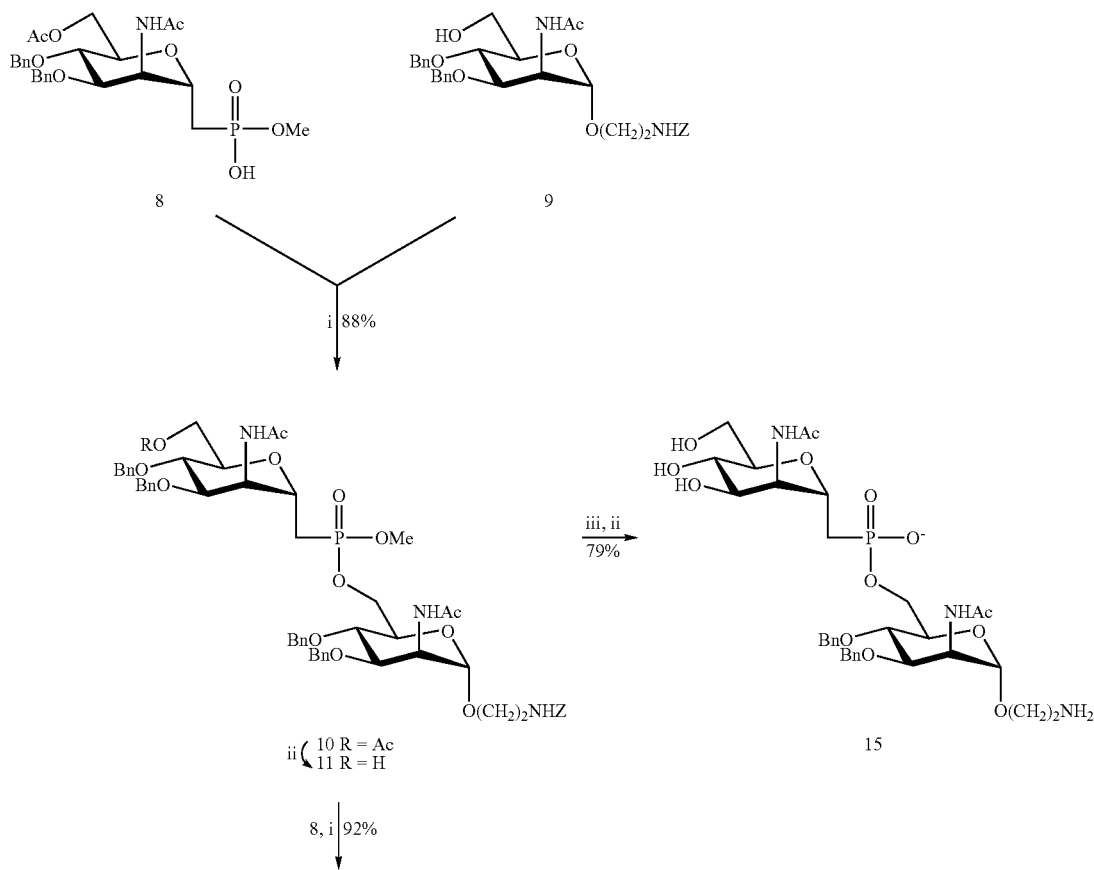

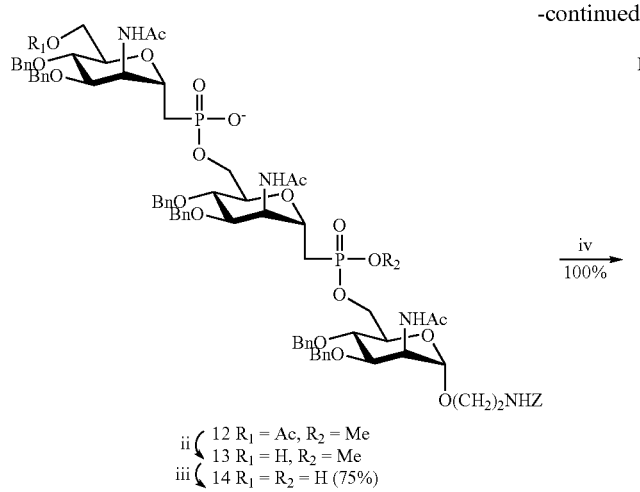 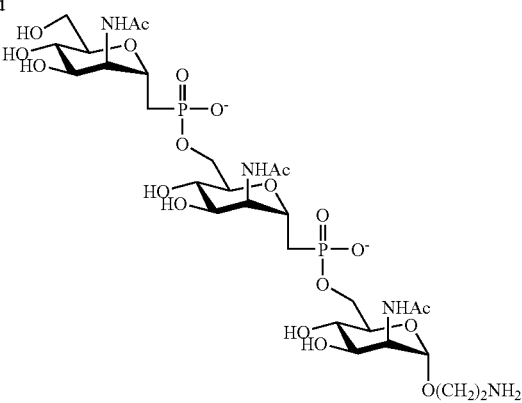

ii { 12 R₁ = Ac, R₂ = Me
    13 R₁ = H, R₂ = Me
iii { 14 R₁ = R₂ = H (75%)

Key: i) (pClPh)₃, DIAD, Et₃N, THF; ii) KOH, MeOH; iii) PhSH, DBU, CH₃CN; iv) H₂, Pd/C,HCl.

2-Carboxybenzylamidoethyl 6-O-[methyl C-(6-O-acetyl-2-acetamido-3,4-di-O-benzyl-2-deoxy-α-D-mannopyranosyl)methanephosphonate]-2-acetamido-3,4-di-O-benzyl-2-deoxy-α-D-mannopyranoside (10). To a solution of 8 (50 mg, 0.093 mmol), tris(4-chlorophenyl)phosphine (38 mg, 0.10 mmol), 2-carboxybenzylamidoethyl 2-acetamido-3,4-di-O-benzyl-2-deoxy-α-D-mannopyranoside (9, 42 mg, 0.072 mmol), Et₃N (0.050 mL, 0.36 mmol) in THF (0.5 mL), DIAD (0.021 mL, 10.4 mmol) was added. After 45 min the solvent was removed under reduced pressure and the residue purified by silica gel chromatography (EtOAc followed by CHCl₃/MeOH 9:1) followed by further purification on a LH-20 gel column (CH₂Cl₂/MeOH 4:1) to give the product 10 (70.1 mg, 0.064 mmol, 88%) as a diastereomeric mixture.

Example 2

2-Carboxybenzylamidoethyl 6-O-[methyl C-(2-acetamido-3,4-di-O-benzyl-2-deoxy-α-D-mannopyranosyl)methanephosphonate]-2-acetamido-3,4-di-O-benzyl-2-deoxy-α-D-mannopyranoside (11). To a solution of 10 (73 mg, 0.066 mmol) in MeOH (2 mL), KOH (7.4 mg, 0.13 mmol) from a stock solution of KOH dissolved in MeOH were added. After 25 min the reaction mixture was diluted with CH₂Cl₂, filtered through a plug of silica and the solvents were removed under reduced pressure. The residue was purified on a LH-20 gel column (CH₂Cl₂/MeOH 4:1) to give 11 (70 mg 0.066 mmol, 100%).

Example 3

2-Carboxybenzylamidoethyl 6-O-[methyl C-(6-O-[methyl C-(6-O-acetyl-2-acetamido-3,4-di-O-benzyl-2-deoxy-α-D-mannopyranosyl)methanephosphonate]-2-acetamido-3,4-di-O-benzyl-2-deoxy-α-D-mannopyranosyl)methanephosphonate]-2-acetamido-3,4-di-O-benzyl-2-deoxy-α-D-mannopyranoside (12). To a solution of 8 (27 mg, 0.051 mmol), tris(4-chlorophenyl)phosphine (19 mg, 0.052 mmol), 11 (38 mg, 0.036 mmol) and Et₃N (0.025 mL, 0.18 mmol) in THF (0.5 mL), DIAD (0.010 mL, 0.052 mmol) was added. After 40 min the reaction mixture was concentrated and purified by silica gel chromatography (EtOAc followed by CHCl₃/MeOH 9:1). The products were further purified on a LH-20 gel column (CH₂Cl₂/MeOH 4:1) to give 12 (52 mg, 0.033 mmol, 92%).

Example 4

2-Carboxybenzylamidoethyl 6-O-[methyl C-(6-O-[methyl C-(2-acetamido-3,4-di-O-benzyl-2-deoxy-α-D-mannopyranosyl) phosphonate]-2-acetamido-3,4-di-O-benzyl-2-deoxy-α-D-mannopyranosyl) phosphonate]-2-acetamido-3,4-di-O-benzyl-2-deoxy-α-D -mannopyranoside (14). To a solution of 12 (67 mg, 0.043 mmol) in MeOH (2 ml), KOH (4.7 mg, 0.085 mmol, 2 eq) from a stock solution of KOH dissolved in MeOH were added. After 25 min the reaction mixture was diluted with DCM, filtered through a plug of silica and the solvents were removed under reduced pressure. The residue was purified on a LH-20 gel column (CH₂Cl₂/MeOH 4:1) to give 13 (65 mg, 0.042 mmol, 100%). To a solution of 13 (36 mg, 0.024 mmol) in acetonitrile (0.5 ml), thiophenol (0.096 ml, 0.94 mmol, 40 eq) and DBU (0.070 ml, 0.47 mmol, 20 eq) were added. After 2.5 h the solvent was removed under reduced pressure and the product purified by silica gel chromatography (toluene followed by CHCl₃/MeOH 9:1+1.5% TEA). The products were further purified on a LH-20 gel column (MeOH+1.5% TEA) to give 14 (30 mg, 0.018 mmol, 75%). ³¹P NMR (CDCl₃): 21.2, 22.4.

Example 5

2-aminoethyl 6-O—[C-(2-acetamido-2-deoxy-α-D-manno mannopyranosyl)methanephosphonate]-2-acetamido-2-deoxy-α-D-mannopyranoside (15). To a solution of 11 (35.1 mg, 0.033 mmol) in acetonitrile (0.5 ml), thiophenol (0.066 ml, 0.64 mmol, 20 equiv.) and DBU (0.048 ml, 0.32 mmol, 10 equiv.) were added. After 2 h the solvent was removed under reduced pressure and the product purified by silica gel chromatography (toluene followed by CHCl₃/MeOH 20:1+1.5% TEA). The products were further purified on a LH-20 gel column (MeOH 1.5% TEA) to give 2-(benzyloxycarbonyl)aminoethyl 6-O—[C-(2-acetamido-3,4-di-O-benzyl-2-deoxy-α-D-mannopyranosyl)methanephosphonate]-2-acetamido-3,4-di-O-benzyl-2-deoxy-α-D-mamiopyra noside (30 mg, 2.63 mmol, 79%). ¹³C-NMR (CD₃OD) 173.55, 172.57, 158.72, 139.94, 139.66, 139.64, 139.39), 138.24, remaining aromatic C 130.36-125.05, 100.26, 78.86, 77.82, 76.03, 75.90, 75.18, 74.60, 74.19, 72.85, 72.27, 72.20, 71.97, 67.36, 67.25, 64.57, 61.09, 54.66, 51.28, 51.16, 50.56, 41.43, 29.94 (d, J=135 Hz), 22.59, 22.43. To a solution of this product (10 mg) in EtOH (4 ml), HCl in water (0.1 M, 0.25 ml) was added followed by a catalytic amount of Pd on carbon. After stirring over night under a 100 psi hydrogen atmosphere the solution was neutralized with sodium acetate. The reaction mixture were filtered through a plug of reversed-phase silica gel and $^{31}$P NMR showed full conversion of the starting material to a single product, which was further purified on a P2-Biogel column to give 15 (100%) after freeze-drying. NMR (D$_2$O): $^{31}$P 23.1; $^{13}$C 22.5, 22.6, 26.7, 28.5, 30.9, 39.5, 47.2, 52.8, 53.1, 53.3, 60.0, 63.6, 63.9, 66.8, 67.8, 69.1, 69.6, 72.0, 72.1, 73.1, 74.5, 99.3, 174.8, 175.4.

Example 6

2-aminoethyl 6-O—[C-(6-O—[C-(2-acetamido-2-deoxy-α-D-mannopyranosyl)methanephosphonate]-2-acetamido-2-deoxy-α-D-mannopyranosyl)methanephosphonate]-2-acetamido-2-deoxy-α-D-mannopyranoside (16). To a solution of 14 (12 mg) in EtOH (4 ml), HCl in water (0.1 M, 0.25 ml) was added followed by a catalytic amount of Pd on carbon. After stirring over night under a 100 psi hydrogen atmosphere the solution was neutralized with sodium acetate. The reaction mixture were filtered through a plug of reversed-phase silica gel and $^{31}$P NMR showed full conversion of the starting material to a single product, which was further purified on a P2-Biogel column to give 16 (100%). NMR (D$_2$O): $^{31}$P 22.72, 22.75; $^{13}$C 22.5, 22.7, 23.9, 26.9, 28.7, 30.9, 39.5, 47.1, 52.8, 53.2, 53.3, 60.9, 63.6, 64.0, 66.9, 67.3, 67.8, 69.2, 69.5, 69.7, 72.1, 72.2, 73.2, 74.2, 74.5, 99.4, 174.8, 175.4.

Example 7a

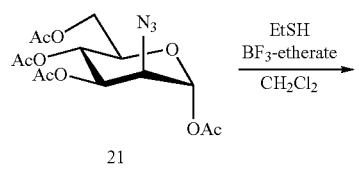

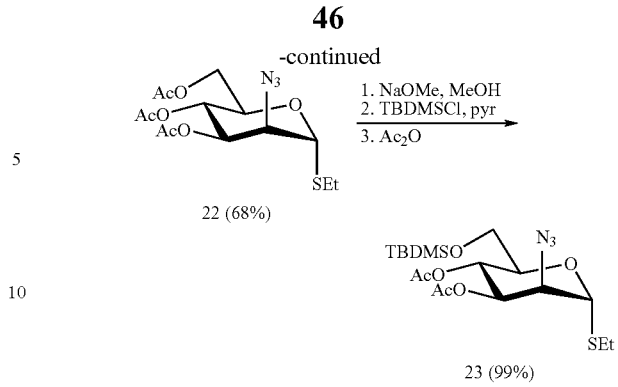

Ethyl 3,4,6-tri-O-acetyl-2-azido-2-deoxy-1-thio-α-D-mannopyranoside (22). To a solution of 1,3,4,6-tetra-O-acetyl-2-azido-2-deoxy-α-D-mannopyranoside (21) (5.04 g, 13.5 mmol) in CH$_2$Cl$_2$ (60 mL) was added EtSH (1.6 mL, 21.6 mmol) and MS (4 Å). The mixture was stirred under argon at rt for 30 min. BF$_3$-etherate (4.8 mL, 38.1 mmol) dissolved in CH$_2$Cl$_2$ (10 mL) was then added during 1 h. After 7 h the mixture was diluted with CH$_2$Cl$_2$, washed with saturated NaHCO$_3$, filtered (silica) and concentrated. Chromatography (1:0→1:1 toluene-EtOAc) gave 22 (3.46 g, 9.22 mmol, 68%); $^{13}$C NMR δ 14.8 (SCH$_2$CH$_3$), 20.6, 20.7, 20.8 (CH$_3$CO), 25.6 (SCH$_2$CH$_3$), 62.3, 62.9, 66.2, 69.0, 71.4 (C-2-6), 82.5 (C-1), 169.6, 170.0, 170.7 (CH$_3$CO).

Ethyl 3,4-di-O-acetyl-2-azido-6-O-(tert-butyldimethylsilyl)-2-deoxy-1-thio-α-D -mannopyranoside (23). To a solution of 22 (3.71 g, 9.88 mmol) in MeOH (30 mL) NaOMe (1 M) was added. The mixture was neutralized with AcOH after 1 h and concentrated. The dry residue was dissolved in pyridine (15 mL) and tert-butyldimethylsilyl chloride (1.94 g, 12.87 mmol) was added. The reaction mixture was stirred at rt overnight. Acetylation with acetic anhydride, dilution with toluene, filtration (silica), concentration and purification by chromatography (1:0→1:1 toluene-EtOAc) gave 23 (4.357 g, 9.73 mmol, 99%); [α]$_D$+109° (c 1.0, CHCl$_3$); $^{13}$C NMR δ −5.33, −5.28 (CH$_3$Si), 14.7 (SCH$_2$CH$_3$), 18.4 ((CH$_3$)$_3$CSi), 20.7, 20.9 (CH$_3$CO), 25.0 (SCH$_2$CH$_3$), 25.9 ((CH$_3$)$_3$CSi), 62.6, 62.9, 67.0, 71.7, 71.9 (C-2-6), 81.5 (C-1), 169.7, 170.1 (CH$_3$CO); $^1$H NMR δ 0.05 (s, 3H), 0.05 (s, 3H), 0.90 (s, 9H), 1.30 (t, 3H), 2.05 (s, 3H), 2.10 (s, 3H), 2.55-2.75 (m, 2H), 3.60-3.75 (m, 2H), 4.10 (m, 1H), 4.15-4.20 (m, 1H), 5.20-5.25 (m, 1H), 5.30-5.35 (m, 1H); HRMS calcd for C$_{18}$H$_{33}$N$_3$NaO$_6$SSi [M+Na]$^+$ 470.1757, found 470.1750.

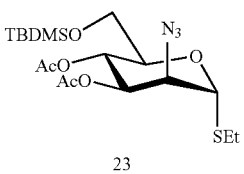

-continued

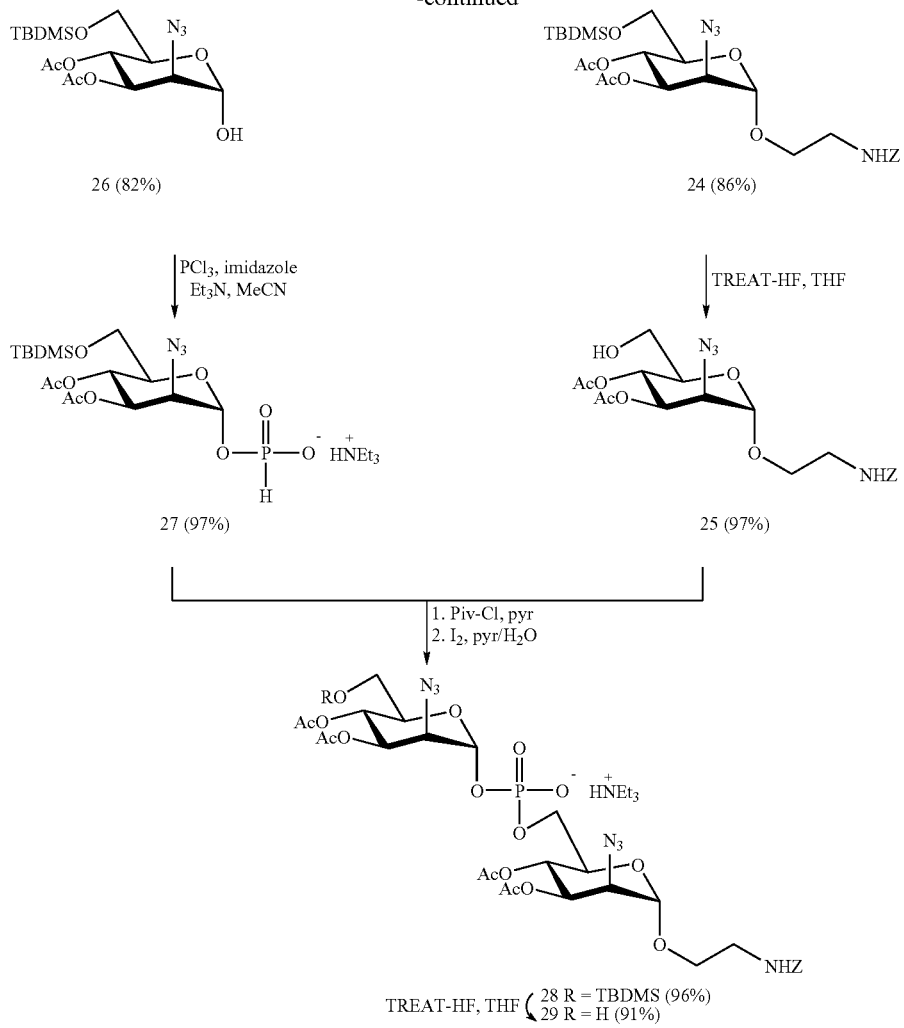

3,4-di-O-acetyl-2-azido-6-O-(tert-butyldimethylsilyl)-2-deoxy-α-D-mannopyranoside (26). NIS (394 mg, 1.75 mmol) and AgOTf (cat) was added to a solution of 23 (653 mg, 1.46 mmol) in wet $CH_2Cl_2$ (10 mL). The reaction mixture was stirred at –20° C. for 30 min. $CH_2Cl_2$ was added and the mixture was washed with $Na_2S_2O_3$ (10%), filtrated (silica) and concentrated. The residue was purified by chromatography (1:0→1:1 toluene-EtOAc) to give 26 (487 mg, 1.21 mmol, 82%); $^{13}C$ NMR δ –5.29, –5.22 ($CH_3Si$), 18.6 (($CH_3)_3CSi$), 20.7, 20.9 ($CH_3CO$), 26.0 (($CH_3)_3CSi$), 62.1, 63.2, 66.9 71.0, 71.6 (C-2-6), 92.7 (C-1), 169.8, 170.3 ($CH_3CO$); $^1H$ NMR δ 0.05 (s, 3H), 0.06 (s, 3H), 0.89 (s, 9H), 2.03 (s, 3H), 2.08 (s, 3H), 3.65-3.70 (m, 2H), 4.00-4.02 (m, 2H), 5.19-5.23 (m, 2H), 5.42-5.47 (m, 1H).

3,4-di-O-acetyl-2-azido-6-O-(tert-butyldimethylsilyl)-2-deoxy-α-D-mannopyran osyl hydrogen-phosphonate, triethylammonium salt (27). A mixture of imidazole (915 mg, 13.45 mmol), $PCl_3$ (335 µL, 3.84 mmol) and $Et_3N$ (2.0 mL, 14.35 mmol) in MeCN (25 mL) was stirred at 0° C. for 30 min. A solution of compound 26 (388 mg, 0.96 mmol) in MeCN (25 mL) was added during 30 min at 0° C. The reaction mixture was then stirred at rt for 10 min, quenched with TEAB (0.5 M) and concentrated. The residue was diluted ($CHCl_3$), washed with TEAB (0.5M), filtered (cotton) and concentrated. Chromatography (1:0→10:1 $CHCl_3$-MeOH+ 1.0% $Et_3N$) of the residue gave 27 (499 mg, 0.93 mmol, 97%); $[α]_D$+67° (c 1.0, $CHCl_3$); $^{13}C$ NMR δ –5.43, ($CH_3Si$), 8.98, 18.3 (($CH_3)_3CSi$), 20.6, 20.8 ($CH_3CO$), 25.8 (($CH_3)_3CSi$), 45.7, 62.4, 62.5, 66.5, 71.1, 72.1 (C-2-6), 93.1 (C-1), 169.4, 170.0 ($CH_3CO$); $^1H$ NMR δ –0.06 (s, 3H), –0.05 (s, 3H), 0.79 (s, 9H), 1.94 (s, 3H), 1.99 (s, 3H), 3.59-3.63 (m, 2H), 3.93-4.00 (m, 2H), 5.21-5.28 (m, 1H), 5.37-5.41 (m, 1H), 5.51-5.50 (m, 1H); $^{31}P$ NMR δ 0.28; HRMS calcd for $C_{16}H_{29}N_3O_9PSi$ [M]⁻ 466.1411, found 466.1400.

Example 7b 2-(benzyloxycarbonyl)aminoethyl 3,4-di-O-acetyl-2-azido-6-O-(tert-butyldimethylsilyl)-2-deoxy-α-D-mannopyranoside (24). Compound 23 (527 g, 1.18 mmol) was dissolved in $CH_2Cl_2$ (10 mL) containing MS (4 Å). Benzyl N-(2-hydroxyethyl) carbamate (300 mg, 1.54 mmol) was added and the mixture was stirred under argon at –20° C. for 30 min before NIS (345 mg, 1.53 mmol) and AgOTf (cat) was added. After 30 min the reaction mixture was neutralized with $Et_3N$, diluted with $CH_2Cl_2$, washed with $Na_2S_2O_3$ (10%), filtered (silica) and concentrated. Chromatography (1:0→1:1 toluene-EtOAc) gave 24 (595 mg, 1.02 mmol, 86%); $[α]_D$+ 46° (c 1.0, $CHCl_3$); $^{13}C$ NMR δ –5.38, –5.34 ($CH_3Si$), 18.4 (($CH_3)_3CSi$), 20.6, 20.8 ($CH_3CO$), 25.9 (($CH_3)_3CSi$), 40.7

(HOCH$_2$CH$_2$NH), 61.6, 62.6, 66.6, 66.9, 67.6, 71.3, 71.8 (C-2-6, PhCH$_2$O, OCH$_2$CH$_2$N), 98.0 (C-1), 128.2, 128.3, 128.6, 136.5 (aromatic C), 156.4 (NHCOOCH$_2$), 169.6, 170.1 (CH$_3$CO); $^1$H NMR δ 0.03 (s, 3H), 0.04 (s, 3H), 0.89 (s, 9H), 2.03 (s, 3H), 2.09 (s, 3H), 2.35 (s, 1H) 3.32-3.40 (m, 1H), 3.44-3.52 (m, 1H), 3.58-3.66 (m, 3H), 3.72-3.80 (m, 2H), 3.98-4.00 (m, 1H), 5.11 (s, 2H), 5.18-5.23 (m, 1H), 5.32-5.36 (m, 1H), 7.16-7.36 (m, 5H).

2-(benzyloxycarbonyl)aminoethyl 3,4-di-O-acetyl-2-azido-2-deoxy-α-D-mannopyranoside (25). To a solution of compound 24 (575 mg, 0.99 mmol) in THF (5 mL), TREAT-HF (0.81 mL, 4.97 mmol) was added. The mixture was stirred under argon at rt overnight. Concentration and chromatography (2:1→0:1 toluene-EtOAc) gave 25 (448 mg, 0.96 mmol, 97%); [α]$_D$+60° (c 1.0, CHCl$_3$); $^{13}$C NMR δ 20.7, 20.8 (CH$_3$CO), 40.7 (HOCH$_2$CH$_2$NH), 61.4, 61.6, 66.4, 67.0, 67.5, 70.9, 71.0 (C-2-6, PhCH$_2$O, OCH$_2$CH$_2$N), 98.2 (C-1), 128.3, 128.3, 128.7, 136.5 (aromatic C), 156.5 (NHCOOBn), 170.1, 170.5 (CH$_3$CO); $^1$H NMR δ 2.04 (s, 3H), 2.1 (s, 3H), 3.32-3.46 (m, 2H), 3.54-3.60 (m, 2H), 3.62-3.78 (m, 3H), 4.02-4.04 (m, 1H), 5.06-5.18 (m, 3H), 5.22-5.28 (m, 1H), 5.36-5.40 (m, 1H), 7.28-7.38 (m, 5H); HRMS calcd for C$_{20}$H$_{26}$N$_4$NaO$_9$ [M+Na]$^+$ 489.1597, found 489.1574.

Example 7c (3,4-di-O-acetyl-2-azido-6-O-(tert-butyldimethylsilyl)-2-deoxy-α-D-mannopyranosyl phosphate)-(1→6)-(2-(Benzyloxycarbonyl)aminoethyl 3,4-di-O-acetyl-2-azido-2-deoxy-α-D-mannopyranoside) triethylammonium salt (28). A mixture of 25 (325 mg, 0.60 mmol) and 27 (217 mg, 0.47 mmol) was dissolved in pyridine (3 mL). Pivaloyl chloride (144 µL, 1.18 mmol) was added and the mixture was stirred under argon at rt for 1 h. The reaction mixture was cooled to −40° C. and a solution of I$_2$ (143 mg, 0.56 mmol) in pyridine-H$_2$O (3 mL 49:1) was added. The oxidation was completed at 0° C. and the mixture was diluted with CHCl$_3$, washed with Na$_2$S$_2$O$_3$ (10%) and cold TEAB (0.5 M). Filtration (cotton), concentration and chromatography (1:0→10:1 CHCl$_3$-MeOH+0.5% Et$_3$N) gave 28 (469 mg, 0.45 mmol, 96%); [α]$_D$+52° (c 1.0, CHCl$_3$); $^{13}$C NMR δ −5.48, −5.38 (CH$_3$Si), 9.27, 18.4 ((CH$_3$)$_3$CSi), 20.6, 20.7, 20.8, 20.8 (CH$_3$CO), 25.9 ((CH$_3$)$_3$CSi), 40.7 (HOCH$_2$CH$_2$NH), 45.8, 61.7, 62.2, 64.5, 66.3, 66.6, 66.7, 67.3, 69.8, 69.9, 71.2, 71.3, 71.8 (C-2-6, 2'-6', PhCH$_2$O, OCH$_2$CH$_2$N) 94.1, 97.9 (C-1, -1'), 128.1, 128.2, 128.6, 136.8 (aromatic C), 156.7 (NHCOOBn), 169.3, 169.7, 170.0, 170.1 (CH$_3$CO); $^1$H NMR δ 0.00 (s, 3H), 0.02 (s, 3H), 0.88 (s, 9H), 1.98 (s, 3H), 2.00 (s, 3H), 2.06 (s, 3H), 2.08 (s, 3H), 3.30-3.38 (m, 1H), 3.42-3.52 (m, 1H), 3.56-3.64 (m, 1H), 3.66-3.68 (m, 2H), 3.74-3.80 (m, 1H), 3.90-4.04 (m, 5H), 4.12-4.14 (m, 1H), 5.1 (s, 2H), 2.16-2.22 (m, 1H), 5.29 (m, 1H), 5.32-5.47 (m, 3H), 5.51-5.54 (m, 1H), 5.63-5.68 (m, 1H), 7.28-7.38 (m, 5H); $^{31}$P NMR δ −3.61.

Example 7d (3,4-di-O-acetyl-2-azido-2-deoxy-α-D-mannopyranosyl phosphate)-(1→6)-(2-(benzyloxycarbonyl)aminoethyl 3,4-di-O-acetyl-2-azido-2-deoxy-α-D-mannopyranoside) triethylammonium salt (29). Compound 28 (472 mg, 0.46 mmol) was dissolved in THF (10 mL) and TREAT-HF (372 µL, 2.28 mmol) was added. The mixture was stirred at rt for 24 h followed by concentration and purification on silica gel (1:0→5:1 CHCl$_3$-MeOH+0.5% Et$_3$N) to give 29 (390 mg, 0.42 mmol, 91%); [α]$_D$+34° (c 1.0, CHCl$_3$); $^{13}$C NMR δ 10.6, 20.6, 20.8, 20.8, (CH$_3$CO), 40.7 (HOCH$_2$CH$_2$NH), 46.1, 61.5, 61.7, 62.2, 62.3, 64.6, 66.6, 66.6, 66.8, 67.4, 69.9, 70.0, 70.9, 71.2, 71.9, (C-2-6, 2'-6', PhCH$_2$O, OCH$_2$CH$_2$N), 94.0, 98.0 (C-1, -1'), 128.1, 128.2, 128.6, 136.6 (aromatic C), 156.6 (NHCOOBn), 169.9, 170.3 (CH$_3$CO); $^{31}$P NMR δ −3.51; HRMS calcd for C$_{30}$H$_{39}$N$_7$O$_{18}$P [M]$^−$ 816.2089, found 816.2078.

The following schemes apply to Examples 8-12.

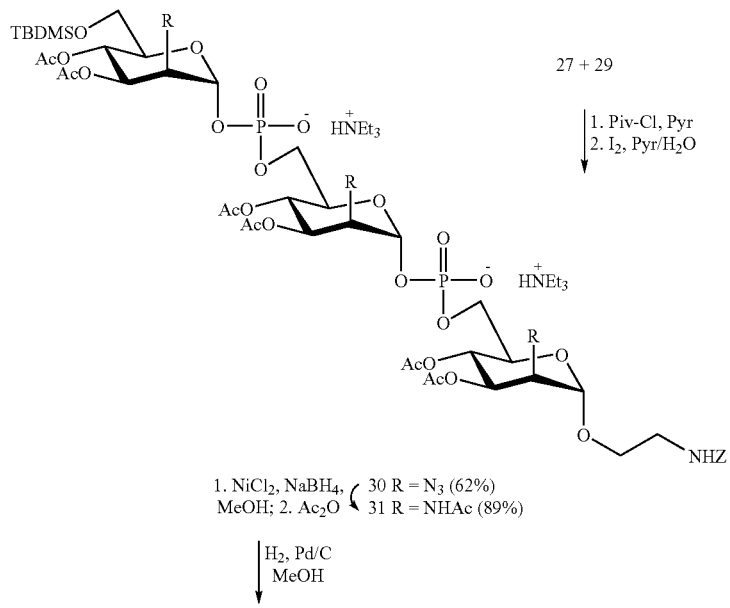

-continued

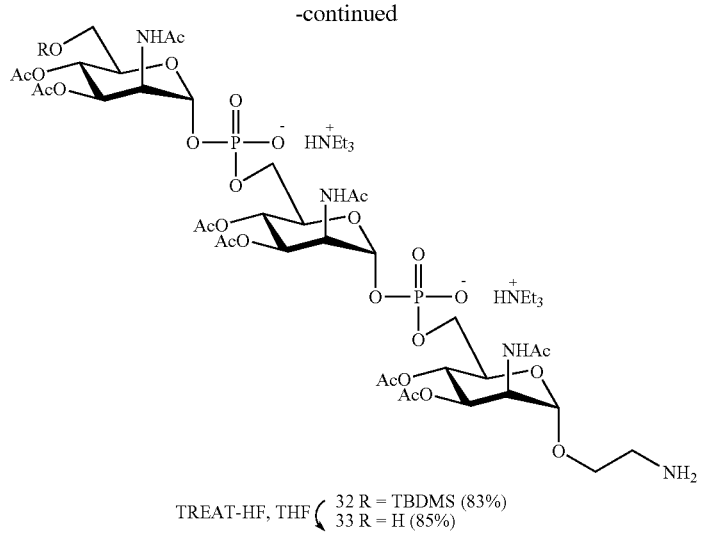

TREAT-HF, THF ( 32 R = TBDMS (83%)
33 R = H (85%)

NaOMe, MeOH ↓

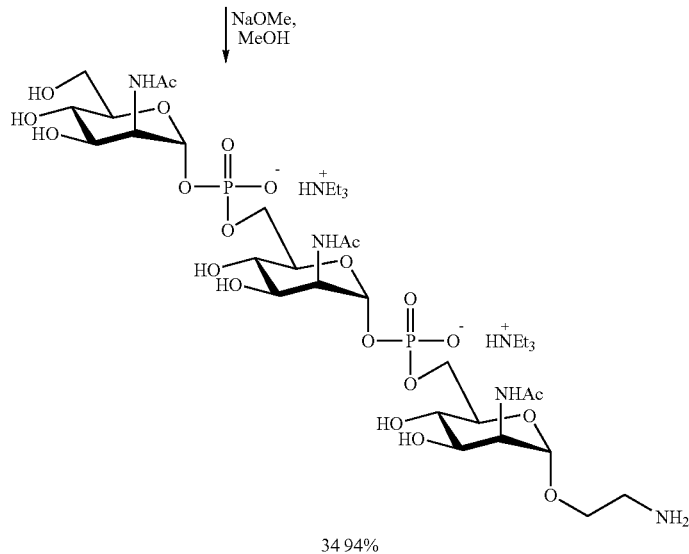

34 94%

Example 7

(3,4-di-O-acetyl-2-azido-6-O-(tert-butyldimethylsilyl)-2-deoxy-α-D-mannopyran osyl phosphate)-(1→6)-(3,4-di-O-acetyl-2-azido-2-deoxy-α-D-mannopyranosyl phosphate)-(1→6)-(2-(Benzyloxycarbonyl)aminoethyl 3,4-di-O-acetyl-2-azido-2-deoxy-α-D -mannopyranoside) bis-triethylammonium salt (30). To a mixture of 27 (273 mg, 0.51 mmol) and 29 (357 mg, 0.39 mmol) in pyridine (3 mL) was added Pivaloyl chloride (119 μL, 0.97 mmol). After 2 h the mixture was cooled to −40° C. and a solution of $I_2$ (119 mg, 0.47 mmol) in pyridine-$H_2O$ (3 mL 49:1) was added. The mixture was diluted with $CHCl_3$ when the temperature reached −10° C. Extraction with $Na_2S_2O_3$ (10%), cold TEAB (0.5 M), filtration (cotton) and chromatography (1:0→5:1 $CHCl_3$-MeOH+0.5% $Et_3N$) gave 30 (351 mg, 0.24 mmol, 62%); $[α]_D$+68° (c 1.0, $CHCl_3$); $^{13}$C NMR δ −5.53, −5.42 ($CH_3Si$), 10.1, 18.3 (($CH_3)_3CSi$), 20.5, 20.6, 20.6, 20.8 ($CH_3CO$), 25.9 (($CH_3)_3CSi$), 40.6 ($HOCH_2CH_2NH$), 45.9, 61.7, 62.1, 62.3, 64.2, 66.2, 66.4, 66.5, 67.1, 69.7, 70.4, 71.0, 71.2, 71.4, 71.6, 77.4 (C-2-6, 2'-6', 2"-6", $PhCH_2O$, $OCH_2CH_2N$), 93.8, 94.0, 97.8 (C-1, -1', -1"), 128.0, 128.2, 128.5, 136.9 (aromatic C), 156.8 (NHCOOBn), 169.3, 169.6, 169.7, 169.8, 169.9, 170.0 ($CH_3CO$); $^1$H NMR δ −0.05 (s, 3H), −0.03 (s, 3H), 0.80 (s, 9H), 1.90-2.00 (m, 18H), 3.23-3.31 (m, 1H), 3.36-3.45 (m, 1H), 3.50-3.64 (m, 4H), 3.69-3.76 (m, 1H), 3.79-3.97 (m, 7H), 4.02-4.15 (m, 3H), 5.00-5.06 (m, 2H), 5.12-5.21 (m, 2H), 5.24-5.31 (m, 1H), 5.33-5.37 (m, 2H), 5.38-5.45 (m, 3H), 6.04-6.10 (m, 1H), 7.18-7.30 (m, 5H); $^{31}$P NMR δ −3.89, −3.56; HRMS calcd for $C_{46}H_{66}N_{10}NaO_{27}P_2Si$ [M+Na]$^-$ 1303.3241, found 1303.3197.

Example 8

(2-acetamido-3,4-di-O-acetyl-6-O-(tert-butyldimethylsilyl)-2-deoxy-α-D-mannopyranosyl phosphate)-(1→6)-(2-acetamido-3,4-di-O-acetyl-2-deoxy-α-D-mannopyranosyl phosphate)-(1→6)-(2-(benzyloxycarbonyl)aminoethyl 2-acetamido-3,4-di-O-acetyl-2-deoxy-α-D-mannopyranoside) bis-triethylammonium salt (31). Compound 30 (83 mg, 0.056 mmol) was dissolved in MeOH (3 mL) and $NiCl_2(H_2O)_6$ was added (cat). Reduction was performed by adding NaBH$_4$ in small amounts over a period of 1 h at 0° C. The mixture was then subjected to acetic anhydride followed by dilution (MeOH) and concentration. The residue was purified on silica gel (1:0→5:1 CHCl$_3$-MeOH+0.5% Et$_3$N) and on LH-20 gel (MeOH+1.5% Et$_3$N), to give compound 31 (76 mg, 0.050 mmol, 89%); [α]$_D$+63° (c 1.0, CHCl$_3$); $^{13}$C NMR δ −5.44, −5.38 (CH$_3$Si), 8.46, 18.4 ((CH$_3$)$_3$CSi), 20.9, 21.0, 21.0, 21.1, 23.0, 23.0, 23.0, 23.3, 23.9 (CH$_3$CO, CH$_3$CONH), 26.0 ((CH$_3$)$_3$CSi), 40.8 (HOCH$_2$CH$_2$NH), 46.1, 50.1, 50.4, 50.7 (C-2, -2', -2''), 59.1, 61.6, 64.5, 65.0, 65.7, 65.9, 66.7, 67.1, 70.0, 70.2, 70.3, 71.3, 77.4 (C-3-6, 3'-6', 3''-6'', PhCH$_2$O, OCH$_2$CH$_2$N), 94.9, 95.1, 99.1 (C-1, -1', -1''), 128.0, 128.1, 128.6, 136.8 (aromatic C), 156.6 (NHCOOBn), 169.5, 169.6, 170.0, 170.5, 170.6, 170.8, 171.3 (CH$_3$CO, CH$_3$CONH); $^{31}$P NMR δ −3.75, −3.39; HRMS calcd for C$_{52}$H$_{79}$N$_4$O$_{30}$P$_2$Si [M+H]$^-$ 1329.4024, found 1329.3984.

Example 9

2-Aminoethyl-(2-acetamido-3,4-di-O-acetyl-6-O-(tert-butyldimethylsilyl)-2-deoxy-α-D-mannopyranosyl phosphate)-(1→6)-(2-acetamido-3,4-di-O-acetyl-2-deoxy-α-D -mannopyranosyl phosphate)-(1→6)-(2-acetamido-3,4-di-O-acetyl-2-deoxy-α-D -mannopyranoside) bis-triethylammonium salt (32). To a solution of compound 31 (37 mg, 0.024 mmol) in MeOH (1.5 mL) was added Amberlite IR −45 (OH$^-$) resin (40 mg) and palladium on activated carbon. The mixture was hydrogenolysed at 100 psi over night, diluted (MeOH), centrifuged and concentrated. Purification on reversed phase gel (1:0→0:1 H$_2$O-MeOH) gave 32 (28 mg, 0.020 mmol, 83%); [α]$_D$+60° (c 1.0, MeOH); $^{13}$C NMR (D$_2$O) δ −5.9, −5.4 (CH$_3$Si), 8.89, 18.7 ((CH$_3$)$_3$CSi), 20.9, 21.0, 22.4, 22.5 (CH$_3$CO, CH$_3$CONH), 26.0 ((CH$_3$)$_3$CSi), 39.7 (HOCH$_2$CH$_2$NH), 47.3, 50.6, 51.4 (C-2, -2', -2''), 62.4, 64.4, 64.7, 64.9, 65.9, 66.2, 66.6, 70.1, 70.8, 71.0, 71.2, 71.5 (C-3-6, 3'-6', 3''-6'', OCH$_2$CH$_2$N), 95.4, 95.5, 99.1 (C-1, -1', -1''), 173.1, 173.3, 173.5, 173.6, 173.8, 174.9, 175.1, 175.2 (CH$_3$CO, CH$_3$CONH); $^{31}$P NMR (D$_2$O) δ −3.04, −2.87; HRMS calcd for C$_{44}$H$_{72}$N$_4$O$_{28}$P$_2$Si [M+H]$^-$ 1195.3656, found 1195.3567.

Example 10

2-aminoethyl(2-acetamido-3,4-di-O-acetyl-2-deoxy-α-D-mannopyranosyl phosphate)-(1→6)-(2-acetamido-3,4-di-O-acetyl-2-deoxy-α-D-mannopyranosyl phosphate)-(1→6)-(2-acetamido-3,4-di-O-acetyl-2-deoxy-α-D-mannopyranoside) bis-triethylammonium salt (33). A solution of TREAT-HF (17 μL, 0.10 mmol) in THF (1.5 mL) was treated with Et$_3$N (17 μL, 0.12 mmol). This solution was added to compound 32 (28 mg, 0.020 mmol). After 30 minutes of stirring at rt the mixture was concentrated and purified on reversed phase gel (1:0→0:1 H$_2$O-MeOH) which gave 33 (22 mg, 0.017 mmol, 85%); [α]$_D$+45° (c 1.0, MeOH); $^{13}$C NMR (D$_2$O) δ 8.87, 20.9, 20.9, 22.3, 22.4 (CH$_3$CO, CH$_3$CONH), 39.6 (HOCH$_2$CH$_2$NH), 47.3, 50.6, 51.3, 51.4 (C-2, -2', -2''), 60.2, 64.3, 64.5, 64.9, 66.2, 66.4, 69.9, 70.0, 70.5, 70.5, 70.7, 70.8, 71.0, 71.6 (C-3-6,3'-6', 3''-6'', OCH$_2$CH$_2$N), 95.3, 95.3, 99.5 (C-1, -1', -1''), 173.3, 173.3, 173.6, 173.7, 173.8, 175.0, 175.1, 175.3 (CH$_3$CO, CH$_3$CONH); $^1$H NMR δ (D$_2$O) 2.03 (s, 3H), 2.08 (s, 3H), 2.09 (s, 3H), 2.14 (s, 3H), 2.14 (s, 3H), 2.18 (s, 3H), 2.24 (s, 3H), 2.24 (s, 3H), 2.24 (s, 3H), 3.28-3.36 (m, 2H), 3.68-3.84 (m, 3H), 4.00-4.18 (m, 5H), 4.27-4.33 (m, 1H), 4.57-4.64 (m, 2H), 5.22-5.30 (m, 1H), 5.31-5.37 (m, 2H), 5.44-5.49 (m, 1H); $^{31}$P NMR (D$_2$O) δ −3.02, −2.95; HRMS calcd for C$_{38}$H$_{58}$N$_4$NaO$_{28}$P$_2$ [M+Na]-1103.261, found 1103.2642.

Example 11

2-aminoethyl(2-acetamido-2-deoxy-α-D-mannopyranosyl phosphate)-(1→6)-(2-acetamido-2-deoxy-α-D-mannopyranosyl phosphate)-(1→6)-(2-acetamido-2-deoxy-α-D-mannopyranoside) bis-triethylammonium salt (34). Compound 33 (22 mg, 0.017 mmol) was dissolved in MeOH (1 mL) and NaOMe (1M) was added. The mixture was concentrated after 30 min and the residue was purified on reversed phase gel (H$_2$O→MeOH). The fractions containing the product were freeze dried to give 34 (14 mg, 0.016 mmol, 94%); [α]$_D$+12.4° (c 0.5, MeOH); $^{13}$C NMR (D$_2$O) δ 22.6 (CH$_3$CONH), 40.1 (HOCH$_2$CH$_2$NH), 53.1, 53.8, 53.9 (C-2, -2', -2''), 60.8, 65.3, 66.6, 67.0, 69.1, 69.3, 69.5, 72.2, 73.0, 74.1 (C-3-6, 3'-6', 3''-6'', OCH$_2$CH$_2$N), 95.8, 95.8, 99.6 (C-1, -1', -1''), 175.5, 175.5, 175.6 (CH$_3$CONH); $^{31}$P NMR (D$_2$O) δ −2.36, −2.22; HRMS calcd for C$_{26}$H$_{47}$N$_4$O$_{22}$P$_2$ [M+H]$^-$ 829.2157, found 829.2064.

Example 13a

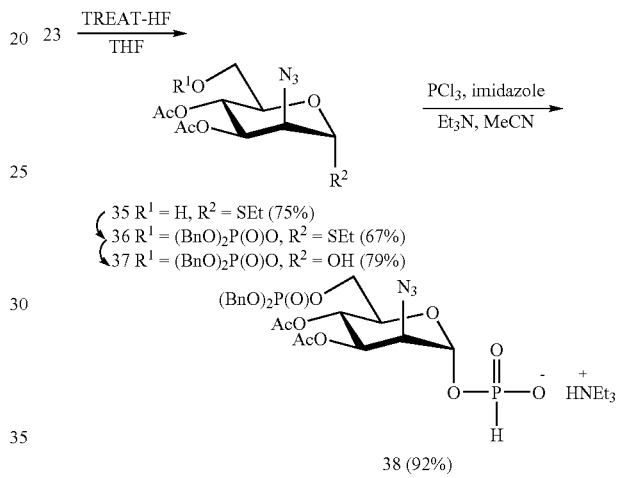

38 (92%)

Ethyl 3,4-di-O-acetyl-2-azido-2-deoxy-1-thio-α-D-mannopyranoside (35). To compound 23 (305 mg, 0.68 mmol) dissolved in THF (6 mL), TREAT-HF (0.55 ml, 3.38 mmol) was added. The mixture was stirred at rt overnight. Concentration and chromatography (10:1→0:1 toluene-EtOAc) gave 35 (171 mg, 0.51 mmol, 75%); $^{13}$C NMR δ 14.7 (SCH$_2$CH$_3$), 20.6, 20.8 (CH$_3$CO), 25.4 (SCH$_2$CH$_3$), 61.3, 63.0, 66.6, 71.1, 71.3 (C-2-6), 82.2 (C-1), 170.0, 170.6 (CH$_3$CO); $^1$H NMR δ 1.26-1.30 (t, 3H), 2.05 (s, 3H), 2.08 (s, 3H), 2.32 (s, 1H), 2.56-2.68 (m, 2H), 3.58-3.67 (m, 2H), 4.09-4.14 (m, 2H), 5.24-5.35 (m, 3H).

Example 13b

Ethyl 3,4-di-O-acetyl-2-azido-2-deoxy-6-O-dibenzylphosphate-1-thio-α-D -mannopyranoside (36). To compound 35 (171 mg, 0.51 mmol) dissolved in CH$_2$Cl$_2$ (10 mL), tetrazole (125 mg, 1.78 mmol) and N—N-diisopropylphosphoramidate (264 μL, 0.76 mmol) was added. The reaction mixture was stirred for 30 min at rt. mCPBA (176 mg, 1.02 mmol) was added at 0° C. and stirring was continued for 30 min. The mixture was diluted (CH$_2$Cl$_2$), washed with Na$_2$S$_2$O$_3$ (10%) and NaHCO$_3$. Filtration (Na$_2$SO$_4$), concentration and chromatography (10:1→2:1 toluene-EtOAc) gave 36 (200 mg, 0.34 mmol, 67%); [α]$_D$+92° (c 1.0, CHCl$_3$); $^{13}$C NMR δ 14.6 (SCH$_2$CH$_3$), 20.5, 20.6 (CH$_3$CO), 25.3 (SCH$_2$CH$_3$), 62.9, 65.7, 66.1, 69.4, 69.4, 69.5, 71.4, (C-2-6, PhCH$_2$O), 82.0 (C-1), 127.9, 128.0, 128.5, 128.5, 128.6, 128.6, 128.7, 135.8, 135.9 (aromatic C), 169.5, 169.9 (CH$_3$CO); $^{31}$P NMR δ −1.36; HRMS calcd for C$_{26}$H$_{32}$N$_3$NaO$_9$PS [M+Na]$^+$ 616.1495, found 616.1487.

Example 13c 3,4-di-O-acetyl-2-azido-2-deoxy-6-O-dibenzylphosphate-α-D-mannopyranoside (37). Compound 36 (281 mg, 0.47 mmol) was dissolved in wet CH$_2$Cl$_2$ (10 mL) and cooled to −20° C. NIS (137 mg, 0.61 mmol) and AgOTf (cat) was added and the mixture was stirred for 30 min at −20° C. The mixture was diluted (CH$_2$Cl$_2$), washed with Na$_2$S$_2$O$_3$ (10%), filtered (Na$_2$SO$_4$) and concentrated. Chromatography (2:1→0:1 toluene-EtOAc) gave 17 (201 mg, 0.37 mmol, 79%); $^{13}$C NMR δ 20.7, 20.7, 62.5, 66.2, 66.3, 66.4, 68.6, 68.7, 69.6, 69.7, 69.8, 69.8, 71.0 (C-2-6, PhCH$_2$O), 92.5 (C-1), 128.0, 128.1, 128.3, 128.6, 128.7, 128.7, 135.6, 135.7 (aromatic C), 169.8, 170.1 (CH$_3$CO); $^{31}$P NMR δ −1.87.

Example 13d 3,4-di-O-acetyl-2-azido-2-deoxy-6-O-dibenzylphosphate-α-D-mannopyranosyl-hydrogen-phosphonate, triethylammonium salt (38). A mixture of imidazole (349 mg, 5.13 mmol), PCl$_3$ (128 μL, 1.47 mmol) and Et$_3$N (765 μL, 5.49 mmol) in MeCN (10 mL) was stirred at 0° C. for 30 min. A solution of compound 37 (201 mg, 0.37 mmol) in MeCN (10 mL) was added during 30 min at 0° C. The reaction mixture was then stirred at rt for 10 min, quenched with TEAB (0.5 M) and concentrated. The residue was diluted (CHCl$_3$), washed with TEAB (0.5 M), filtered (cotton) and concentrated. Chromatography (1:0→10:1 CHCl$_3$-MeOH+ 1.0% Et$_3$N) of the residue gave 38 (243 mg, 0.34 mmol, 92%); [α]$_D$ +55° (c 1.0, CHCl$_3$); $^{13}$C NMR δ 9.34, 20.6, 20.7 (CH$_3$CO), 45.9, 62.4, 62.5, 65.6, 65.7, 69.4, 69.5, 69.9, 70.0, 70.9 (C-2-6, PhCH$_2$O), 93.0 (C-1), 128.0, 128.0, 128.1, 128.5, 128.5, 128.6, 135.8 (aromatic C), 169.5, 169.9 (CH$_3$CO); $^{31}$P NMR δ −1.32, 0.29; HRMS calcd for C$_{24}$H$_{28}$N$_3$O$_{12}$P$_2$ [M]$^-$ 612.1148, found 612.1129.

The following scheme applies to Examples 13e and 14-17.

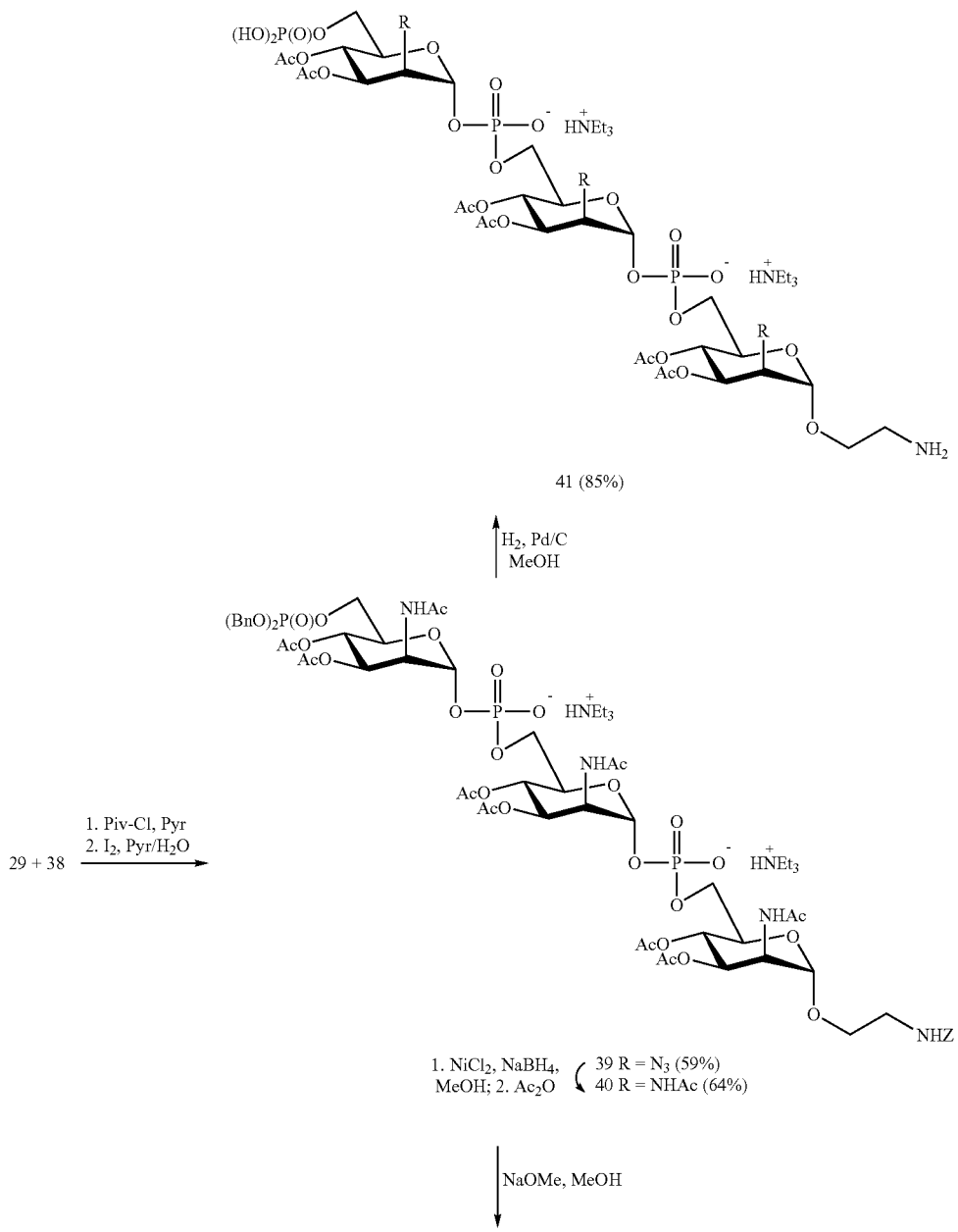

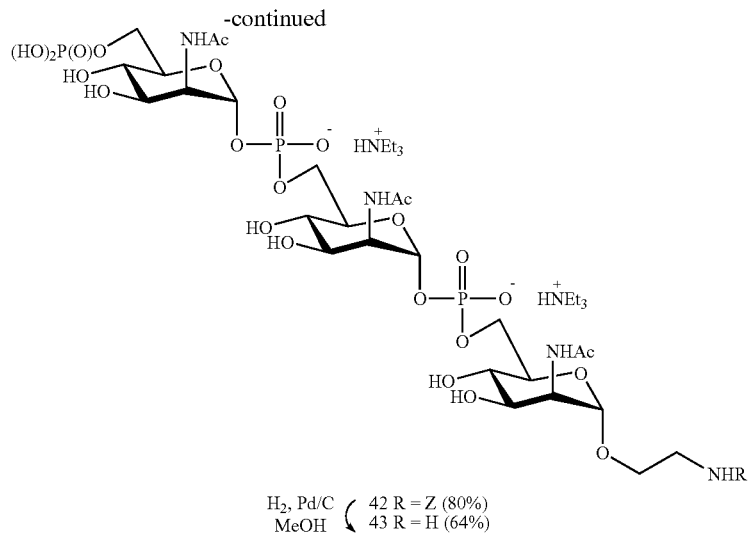

H₂, Pd/C  42 R = Z (80%)
MeOH     43 R = H (64%)

Example 13e 2-(Benzyloxycarbonyl)aminoethyl(3,4-di-O-acetyl-2-azido-2-deoxy-6-O-dibenzylphosphate-α-D-mannopyranosyl phosphate)-(1→6)-(3,4-di-O-acetyl-2-azido-2-deoxy-α-D-mannopyranosyl phosphate)-(1→6)-(3,4-di-O-acetyl-2-azido-2-deoxy-α-D -mannopyranoside) bis-triethylammonium salt (39). A mixture of 38 (96 mg, 0.13 mmol) and 29 (103 mg, 0.11 mmol) was dissolved in pyridine (3 mL). Pivaloyl chloride (34 μL, 0.28 mmol) was added and the mixture was stirred under argon at rt for 2 h. The mixture was cooled to −40° C. and a solution of I₂ (34 mg, 0.13 mmol) in pyridine-H₂O (3 mL 49:1) was added. The oxidation was completed at −10° C. and the mixture was diluted with CHCl₃, washed with Na₂S₂O₃ (10%) and cold TEAB (0.5 M). Filtration (cotton), concentration and chromatography (1:0→5:1 CHCl₃-MeOH+0.5% Et₃N) gave 39 (106 mg, 0.065 mmol, 59%); [α]$_D$+80° (c 1.0, CHCl₃); $^{13}$C NMR δ 10.2, 20.6, 20.7, 20.8 (CH₃CO), 40.6 (HOCH₂CH₂NH), 45.9, 57.9, 61.7, 62.3, 64.4, 65.5, 65.7, 66.1, 66.5, 66.6, 67.2, 69.4, 69.5, 70.3, 71.0, 71.4 (C-2-6, 2'-6', 2''-6'', PhCH₂O, OCH₂CH₂N), 93.9, 94.0, 97.8 (C-1, -1', -1''), 128.0, 128.1, 128.2, 128.5, 128.6, 136.0, 136.9 (aromatic C), 156.8 (NHCOOBn), 169.6, 169.7, 169.8, 169.9 (CH₃CO); $^{31}$P NMR δ −4.13, −3.58, −1.52.

Example 12

2-(Benzyloxycarbonyl)aminoethyl(2-acetamido-3,4-di-O-acetyl-2-azido-2-deoxy-6-O-dibenzylphosphate-α-D-mannopyranosyl phosphate)-(1→6)-(2-acetamido-3,4-di-O-acetyl-2-azido-2-deoxy-α-D-mannopyranosyl phosphate)-(1→6)-(2-acetamido-3,4-di-O-acetyl-2-azido-2-deoxy-α-D-mannopyranoside) bis-triethylammonium salt (40). Compound 39 (76 mg, 0.047 mmol) was dissolved in MeOH (3 mL) and NiCl₂(H₂O)₆ was added (cat). Reduction was performed by adding NaBH₄ in small amounts over a period of 30 min at 0° C. The mixture was then subjected to acetic anhydride followed by dilution (MeOH) and concentration. The residue was purified on silica gel (1:0→5:1 CHCl₃-MeOH+0.5% Et₃N) and on LH-20 gel (MeOH+1.5% Et₃N), to give compound 40 (50 mg, 0.030 mmol, 64%); $^{13}$C NMR (D₂O) δ 8.89, 20.7, 20.8, 22.4 (CH₃CO, CH₃CONH), 40.7 (HOCH₂CH₂NH), 47.3, 50.7, 51.4 (C-2, -2', -2''), 64.5, 65.9, 66.1, 66.5, 66.6, 67.2, 67.3, 69.7, 69.8, 70.5, 70.8, 70.9, 71.1 (C-3-6, 3'-6', 3''-6'', PhCH₂O, OCH₂CH₂N), 95.2, 95.3, 98.8 (C-1, -1', -1''), 128.2, 128.9, 129.0, 129.3, 129.5, 129.7, 135.7, 135.8, 137.1 (aromatic C), 158.7 (NHCOOBn), 172.8, 172.9, 173.2, 173.3, 173.4, 173.4, 174.8, 174.9, 175.0 (CH₃CO, CH₃CONH); $^{31}$P NMR (D₂O) δ −3.05, −2.75, −1.20.

Example 13

2-aminoethyl(2-acetamido-3,4-di-O-acetyl-2-azido-2-deoxy-6-O-phosphate-α-D -mannopyranosyl phosphate)-(1→6)-(2-acetamido-3,4-di-O-acetyl-2-azido-2-deoxy-α-D -mannopyranosyl phosphate)-(1→6)-(2-acetamido-3,4-di-O-acetyl-2-azido-2-deoxy-α-D -mannopyranoside) tris-triethylammonium salt (41). To a solution of compound 40 (46 mg, 0.027 mmol) in MeOH (2 mL) was added amberlite IR −45 (OH⁻) resin (46 mg) and palladium on activated carbon. The mixture was hydrogenolysed at 100 psi over night, diluted (MeOH), centrifuged and concentrated. Purification on reversed phase gel (1:0→0:1 H₂O-MeOH) gave 41 (34 mg, 0.023 mmol, 85%); [α]$_D$+43° (c 1.0, MeOH); $^{13}$C NMR (D₂O) δ 8.89, 20.9, 20.9, 22.4, 22.4 (CH₃CO, CH₃CONH), 39.6, (HOCH₂CH₂NH), 47.3, 50.6, 51.3, 51.4 (C-2, -2', -2''), 63.6, 64.4, 64.8, 66.1, 66.2, 66.4, 69.9, 70.0, 70.6, 70.7, 71.0 (C-3-6, 3'-6', 3''-6'', OCH₂CH₂N), 95.3, 95.4, 99.1 (C-1, -1', -1''), 173.2, 173.3, 173.4, 173.6, 173.7, 173.7, 175.0, 175.1, 175.2 (CH₃CO, CH₃CONH); $^{31}$P NMR (D₂O) δ −3.08, −2.95, 0.05; HRMS calcd for $C_{38}H_{59}N_4O_{31}P_3$ [M/2+H]⁻ 580.1188, found 580.1142.

Example 14

2-(Benzyloxycarbonyl)aminoethyl(2-acetamido-2-azido-2-deoxy-6-O-dibenzylphosphate-α-D-mannopyranosyl phosphate)-(1→6)-(2-acetamido-2-azido-2-deoxy-α-D-mannopyranosyl phosphate)-(1→6)-(2-acetamido-2-azido-2-deoxy-α-D -mannopyranoside) bis-sodium salt (42). Compound 40 (50 mg, 0.030 mmol) was dissolved in MeOH (3 mL) and NaOMe (1M) was added. The reaction mixture was stirred for 1 h at rt. Concentration and purification on reversed phase gel (1:0→0:1 H₂O-MeOH) gave 42 (30 mg, 0.024 mmol, 80%); $^{13}$C NMR (D₂O) δ 22.6 (CH₃CONH), 40.7 (HOCH₂CH₂NH), 53.1, 53.8, 54.0 (C-2, -2', -2''), 65.1, 66.4, 66.5, 66.8, 67.5, 68.9, 69.1, 69.6, 71.0, 71.1, 71.9, 72.0, 72.3 73.1 (C-3-6, 3'-6', 3"-6", PhCH$_2$O, OCH$_2$CH$_2$N), 95.6, 95.8, 99.4 (C-1, -1', -1"), 128.1, 128.4, 129.0, 129.0, 129.4, 129.5, 129.8, 135.7, 135.8, 137.1 (aromatic C), 158.8 (NHCOOBn), 175.3 (CH$_3$CONH); $^{31}$P NMR (D$_2$O) δ −2.35, −2.23, −0.96.

Example 15

2-aminoethyl(2-acetamido-2-azido-2-deoxy-6-O-phosphate-α-D-mannopyranosyl phosphate)-(1→6)-(2-acetamido-2-azido-2-deoxy-α-D-mannopyranosyl phosphate)-(1→6)-(2-acetamido-2-azido-2-deoxy-α-D-mannopyranoside) tris-sodium salt (43). Compound 42 (30 mg, 0.024 mmol) was dissolved in MeOH (2 mL). Amberlite IR −45(OH$^-$) resin (30 mg) and palladium on activated carbon were added. The mixture was hydrogenolysed at 100 psi over night, diluted (MeOH), centrifuged and concentrated. Purification on reversed phase gel (1:0→0:1 H$_2$O-MeOH) gave 43 (15 mg, 0.015 mmol, 64%); [α]$_D$+13.6° (c 0.5, MeOH); $^{13}$C NMR (D$_2$O) δ 22.6, 22.6, 22.6 (CH$_3$CONH), 39.7 (HOCH$_2$CH$_2$NH), 49.5, 53.0, 53.7, 53.8 (C-2, -2', -2"), 63.8, 64.2, 65.1, 65.2, 65.4, 66.5, 66.7, 67.0, 68.9, 69.2, 69.5, 72.2, 72.3, 72.9, 73.1, 73.2, 73.4, 73.4 (C-3-6, 3'-6', 3"-6", OCH$_2$CH$_2$N), 95.9, 99.6 (C-1, -1', -1"), 175.4, 175.5, 175.5 (CH$_3$CONH); $^{31}$P NMR (D$_2$O) δ −2.35, −2.30, 2.2; HRMS calcd for C$_{26}$H$_{46}$N$_4$Na$_2$O$_{25}$P$_3$ [M+2Na]$^-$ 953.1459, found 953.1440.

Example 16

To study the influence of C-phosphonate in place of phosphodiester on the immunogenicity and stability of the MenA saccharide, a synthetic oligosaccharide analogous to trimers of the repeating unit of Neisseria meningitidis group A polysaccharide was synthesized and conjugated to the carrier protein CRM197. The glycoconjugate was analyzed in order to verify physicochemical characteristics and immunogenicity in mice. The structure of the conjugate is below.

This compound was obtained by replacing the phosphodiester groups linking the monosaccharides, with a C-phosphonate group in the non-acetylated and non-phosphorylated base molecule.

a) Physicochemical Characterization of CRM-MenAsynth Glycoconjugates

The conjugate was characterized for content of saccharide, proteins, unbound (free) saccharide. Furthermore SDS_Page and Western Blot against specific anti MenA antibodies were performed.

Saccharide and Protein Concentrations

The freeze dried product as reconstituted with saline (final concentration=0.8 mg/ml) and assayed by calorimetric test for total phosphorus and protein content (MicroBCA assay). The phosphorus content was then converted to total saccharide content using the appropriate converting factor.

Because some precipitate was generated during storage of the conjugate, a concentrate phosphate buffer (Na phosphate 100 mM pH 7.5) was added to reach 10 mM as final concentration. Then the concentration was recalculated considering the dilution factor. The conjugates had a total saccharide content of 97.10 μg/ml and protein content of 215.63 μg/ml after dilution with phosphate buffer.

b) Immunogenicity in Mice

The immunogenicity of the conjugate with the synthetic oligosaccharide was analyzed in ELISA and bactericidal assays. BALB/c mice (8/group) were immunized with the purified glycoconjugates formulated with and without alum phosphate as adjuvant. The immunisation protocol, shown in Table 1, included three doses (200 ng each) at days 0, 14 and 28 with a final bleeding at day 42. Post 1, post 2 and post 3 dose sera were analyzed to determine specific total IgG and the corresponding antibody functional activity. MenA-CRM 2011 is the wild type MenA conjugate.

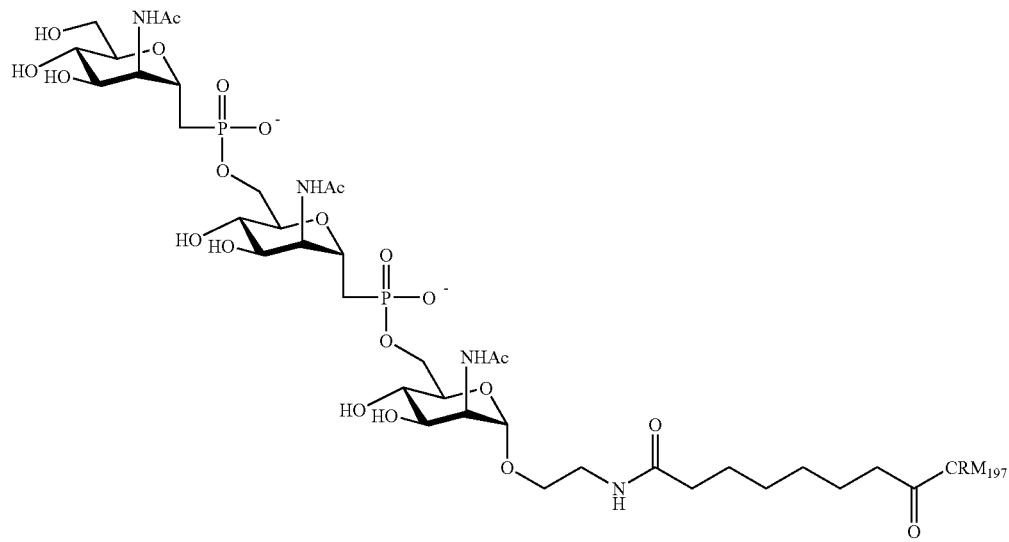

TABLE 1

Scheme of immunization groups and treatment regimen

| Vaccine | n° Doses | Dilution | Dose (µg) | Formul. | n° Mouse | Administr. |
|---|---|---|---|---|---|---|
| MenA-CRM phosphonate conj. | 3 | 1/5 | 0.2 | AlPO$_4$ | 33-40 | 0.5 ml s.c. |
| MenA-CRM phosphonate conj. | 3 | 1/5 | 0.2 | NO AlPO$_4$ | 73-80 | 0.5 ml s.c. |
| MenA-CRM 2011 | 3 | 1/5 | 0.2 | AlPO$_4$ | 81-88 | 0.5 ml s.c. |
| MenA-CRM 2011 | 3 | 1/5 | 0.2 | NO AlPO$_4$ | 89-96 | 0.5 ml s.c. |

ELISA Assay

Sera were analyzed in ELISA assay for specific determination of IgG antibody responses in mice sera. Total IgG titres against A, C, W135 and Y polysaccharide antigens (MenA, MenC, MenW, MenY) were calculated by linear regression curves and expressed as ELISA units/ml (EU/ml). Sera titres resulted from the comparison to the titration curve of a standard serum.

Microtitre plates were coated with a mixture of capsular polysaccharide and methylated human serum albumin at a final concentration of 5.0 µg/ml each, in PBS pH 7.4. Plates were sealed, incubated overnight at 2°-8° C., then washed and saturated with a buffer containing 5% fetal calf serum, as blocking reagent, in PBS pH 7.4. After one hour incubation at room temperature, plates were washed and diluted test sera were added to wells in row 1. Sera were analyzed by a titration curve with a two-fold dilution step. After overnight incubation at 2°-8° C., plates were washed and a goat anti-mouse antibody conjugated to alkaline phosphatase was diluted 1:2000 in saturation buffer and added to the plates. The secondary antibody was incubated for 2 hours at 37° C. and, after washing, plates were added with chromogenic substrate solution (1 mg/ml p-nitro phenyl phosphate in 1 M diethanolamine buffer pH 9.8, 0.5 mM MgCl$_2$, 0.02% NaN$_3$). Reactions were incubated for 30 min at room temperature and absorbance values were read at 405-620 nm wavelength.

Sera with absorbance values of first point superior to that of the standard were retested using a higher initial dilution.

Mice with negative antibody response (O.D. values of first point lower than 0.300 at dilution 1:100) were assigned a titre of 2 EU/ml and classified as "non-responders".

Serum Bactericidal Antibody (SBAb) Assay

Functional antibodies induced by vaccine immunizations were analyzed by measuring complement-mediated lysis in vitro of *Neisseria meningitidis* (Goldschneider, et al., 1969). A commercial lot of baby rabbit complement was used as source of complement (Pelfreeze lot No. 09958).

The assay protocol was based on the inoculum of the test strain in Mueller Hinton broth (Difco) with the addition of 0.25% glucose, starting from isolated colonies grown on agar chocolate. Bacterial culture was incubated at 37° C. with 5% CO$_2$ and the growth stopped when bacteria reached early exponential phase (O.D.$_{600}$ 0.220-0.240). The culture was diluted to $10^{-4}$ Colony Forming Units (CFU)/ml in Gey's balanced salt solution with 1% BSA and incubated for 1 hour at 37° C. with 5% CO$_2$, in the presence of heat inactivated test sera pools and baby rabbit complement. Before (T0) and one hour after (T1) the incubation, reaction mixtures were plated onto Mueller Hinton agar (Difco). Plates were incubated overnight at 37° C. with 5% CO$_2$ and CFU/ml corresponding to T0 and T1 were counted.

Serum bactericidal antibody titres were expressed as reciprocal serum dilution yielding 50% of killing of bacteria.

Results

Physicochemical Characterization

The results of physicochemical analyses indicate that the glycosylation degree of the conjugate is very low. The low conjugation degree is indicated also by the modest signals obtained in Western Blot and by the small differences noticed in SDS-Page between the conjugates and the CRM reference. The conjugation conditions as well as the purification of the conjugates may be optimized.

ELISA results

Figure 4:
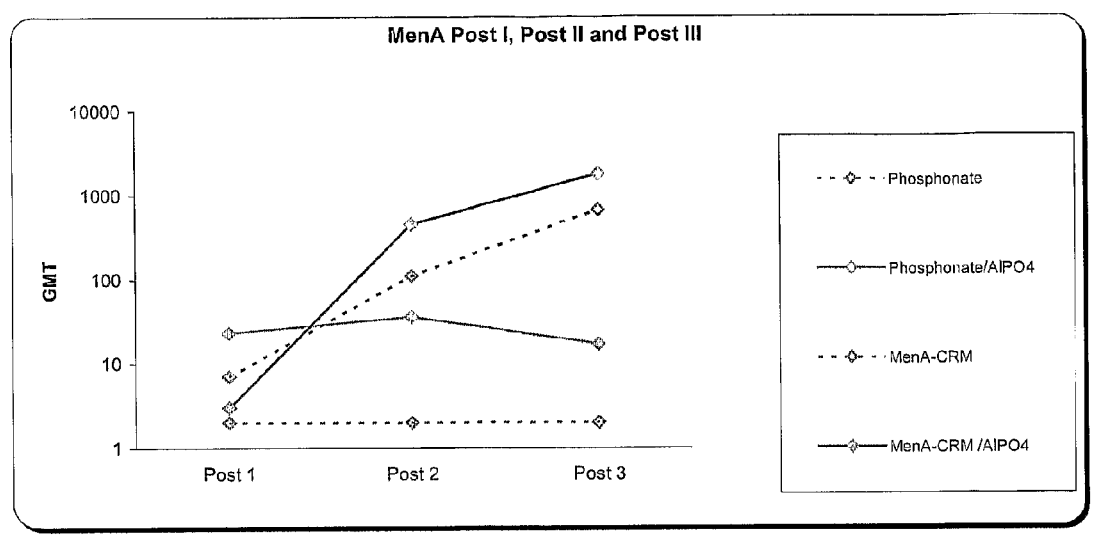
FIG. 4 shows the relationship between the specific antibody responses induced by synthetic glycoconjugate and the control oligosaccharide conjugate at different vaccine doses.

Results obtained are reported in Table 2 and FIG. 4. ELISA titres from each single animal were measured and are expressed in ELISA Unit/ml (EU/ml). The specific antibody response to each glycoconjugate was calculated as the Geometric Mean Titre (GMT) of the corresponding immunisation group.

Post 2 dose sera showed low titre in the synthetic conjugate formulated with the adjuvant and any titre in immunization groups treated without the adjuvant.

The conjugate did not show any titre with and without alum.

As expected, control groups treated with and without the adjuvant showed high responses.

TABLE 2

ELISA antibody titres against polysaccharide MenA determined in post 1, post 2 and post 3 dose mice sera.

| | | Post 1 | Post 2 | Post 3 |
|---|---|---|---|---|
| − | Phosphonate conjugate | 2 | 2 | 2 |
| + | Phosphonate conjugate/AlPO$_4$ | 23 | 36 | 17 |
| MenA lyo− | MenA-CRM | 7 | 110 | 672 |
| MenA lyo+ | MenA-CRM/AlPO$_4$ | 3 | 453 | 1796 |

Geometric Mean Titre calculated for each immunization group are reported.

SBAb Assay Results

Serum bactericidal titres were determined in sera pools prepared from each immunization group. The bactericidal titre is expressed as the reciprocal serum dilution resulting in 50% decrease in CFU/ml of reaction mixtures compared to the control CFU/ml measured at T0. Bactericidal titres were measured against the serogroup A strain F8238. SBAb antibody titres are reported in Table 3. (MenA-CRM is the wild type control.)

TABLE 3

Bactericidal activity in post 2 and post 3 dose sera pools.

| | | Post 2 | Post 3 |
|---|---|---|---|
| − | Phosphonate conjugate | <4 | <4 |
| + | Phosphonate conjugate/AlPO$_4$ | 64 | 256 |
| MenA lyo− | MenA-CRM | 2048 | 4096 |
| MenA lyo+ | MenA-CRM/AlPO$_4$ | 4096 | 8192 |

Conclusions

The conjugate was prepared and analyzed for physicochemical, immunochemical and immunological properties.

Both physicochemical and immunochemical analyses indicated glycosylation degrees of the conjugates.

In control groups, titres were high in response to immunizations either with or without the adjuvant.

In post 3 sera pools, titres increased compared to post 2 dose sera. In groups treated with the synthetic conjugate without alum titres were not measurable in immunizations with the adjuvanted conjugate titres were measurable but lower.

Titres of control immunizations performed with the oligo-conjugate were significantly higher.

The results give evidence that the synthetic MenA oligosaccharide conjugated to the protein carrier CRM197 is immunogenic in mice. The conjugates have C-phosphonate linkages that should be much more stable than the native phosphodiester bonds. The fact that some immunogenicity has been detected is promising.

It will be appreciated that the foregoing examples are provided to illustrate the invention, not to limit its scope. Various variations and combinations of the elements disclosed are viable as one of ordinary skill would recognize, and these are also within the scope of the invention. For example, a wide array of protecting groups for amine and hydroxyl groups are well known, and many of these can be used in place of the ones specifically recited herein without departing from the spirit of the invention.

The invention claimed is:

1. An oligosaccharide comprising a first mannose unit and a second mannose unit, wherein the first mannose unit comprises a spacer moiety in the alpha configuration at C-1, which spacer is capable of conjugating to a protein,
wherein the first mannose unit is connected to the second mannose unit through a 1,6-linkage which connects C-6 of the first unit to C-1 of the second unit,
and wherein the 1,6-linkage comprises a phosphonate.

2. The oligosaccharide of claim 1, wherein the 1,6-linkage is in the alpha configuration.

3. The oligosaccharide of claim 1 or 2, wherein the first mannose unit is a 2-deoxy-2-aza substituted mannose derivative.

4. The oligosaccharide of claim 1 or 2, wherein the second mannose unit is a 2-deoxy-2-aza substituted mannose derivative.

5. The oligosaccharide of claim 1 or 2, comprising at least three mannose units.

6. The oligosaccharide of claim 1 or 2, wherein the 1,6-linkage is of the form [C-1 of second mannose unit]-$CH_2$—P—O—[C-6 of first mannose unit].

7. The oligosaccharide of claim 1 or 2, wherein each 2-aza substituent present is selected from $NH_2$, NHAc, and $N_3$.

8. The oligosaccharide of claim 1, wherein a third mannose unit is connected to the second mannose unit by a linkage which comprises phosphorus, and wherein the linkage connects C-6 of the second mannose unit to C-1 of the third mannose unit.

9. The oligosaccharide of claim 8, wherein the linkage that connects C-6 of the second mannose unit to C-1 of the third mannose unit comprises a phosphonate.

10. The oligosaccharide of claim 8 or 9, which is of the formula:

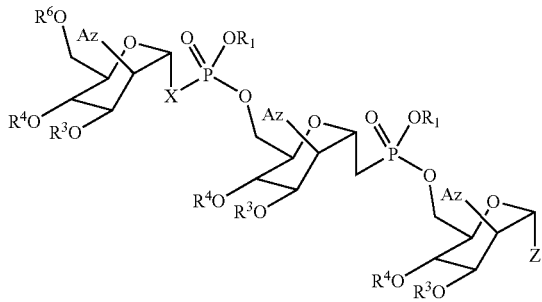

wherein each Az is independently selected from $NH_2$, NHAc, and $N_3$;

Z represents the spacer moiety that is capable of conjugating to a protein, and that may be in protected form or unprotected or that may be conjugated to a protein;
each $R^1$ is independently H, optionally substituted C1-C6 alkyl, or M, where M represents a cation;
X is O or $CH_2$;
each $R^3$ and $R^4$ is independently selected from the group consisting of H, Ac, Bn, and other protecting group;
and $R^6$ is H, or a protecting group, or a phosphate, or a linkage to an additional saccharide unit.

11. The oligosaccharide of claim 1 or 8, further comprising a protein that is conjugated to the oligosaccharide through the spacer moiety that is in the alpha-configuration at C-1 of the first mannose unit.

12. The oligosaccharide of claim 11, wherein the protein is an inactivated bacterial toxin selected from diphtheria toxoid, pertussis toxoid, E. coli LT, E. coli ST, Pseudomonas aeruginosa exotoxin (rEPA), or tetanus toxoid, or wherein the protein is CRM 197.

13. The oligosaccharide of claim 1 or 8, wherein the spacer moiety comprises a hydroxyl or an amine, either of which is optionally protected or is optionally conjugated to a protein.

14. The oligosaccharide of claim 10, wherein $R^3$ is an acyl group and $R^4$ is H.

15. The oligosaccharide of claim 1, which comprises the formula:

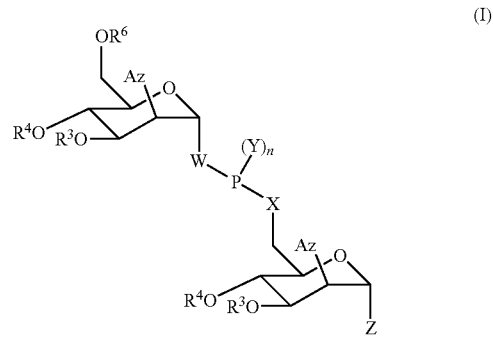

wherein each Az represents an aza substituent;
each $R^3$ and $R^4$ independently represents H or a protecting group;
$R^6$ represents H, a protecting group, or a linker attached to another saccharide unit;
one of W and X is O, and the other of W and X is $CN_2$;
n is 1 or 2;
$Y_n$ is OR when n is 1, and when n is 2, one Y is =O and the other Y is OR,
wherein R is H, C1-C6 alkyl, or C6-C12 aryl, or C6-C12 arylalkyl, or R is M, where M is a cation; and
Z is OR', SR', or NR'2, where each R' is independently H or an optionally substituted alkyl, acyl, aryl, arylalkyl, heteroalkyl, heteroacyl, heteroaryl, or heteroarylalkyl group;
or Z represents a linker attached to another saccharide unit or the spacer moiety conjugated to a protein.

16. The oligosaccharide of claim 15, wherein a protein is conjugated to the oligosaccharide through an amide or ester linkage.

17. The oligosaccharide of claim 15, wherein W is $CH_2$, X is O, Az is NHAc and n is 2.

18. The oligosaccharide of claim 15 or 16, wherein R is M and Z comprises —O—$(CH2)_n$—NH—, wherein n is 2-6.

19. The oligosaccharide of claim 15 or 16, wherein each $R^3$ and $R^4$ is independently H or Ac.

20. A method to make an oligosaccharide, which method comprises:
   linking a first moiety which comprises at least one aza substituted mannose unit through a 1,6-linkage which comprises a phosphonate to a second moiety which comprises at least one aza substituted mannose unit,
   wherein the first moiety comprises a spacer moiety, which spacer moiety is linked to C-1 of a mannose unit in the alpha-configuration.

21. The method of claim 20, wherein a Mitsunobu reaction is used to link C-6 of a mannose unit of the first moiety to C-1 of a mannose unit of the second moiety.

22. The method of any of claims 20-21, wherein the 1,6-linkage is a 1,6-alpha linkage.

23. The method of any of claims 20-21, wherein the linked N-substituted mannose units comprise the formula (1)

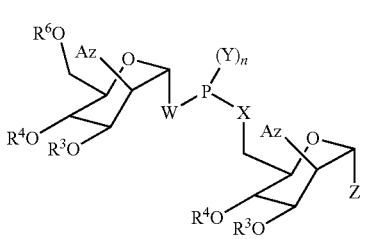

(I)

wherein each Az represents an aza substituent;
each $R^3$ and $R^4$ independently represents H or a protecting group;
$R^6$ represents H, a protecting group, or a linker attached to another saccharide unit; one of W and X is O, and the other of W and X is $CH_2$;
n is 1 or 2;
$Y_n$ is OR when n is 1, and when n is 2, one Y is =O and the other Y is OR,
wherein R is H, C1-C6 alkyl, or C6-C12 aryl, or C6-C12 arylalkyl, or R is M, where M is a monovalent cation; and
Z represents a moiety capable of being conjugated to a protein, which may be in protected form.

24. The method of claim 23, wherein X is $CH_2$ and W is O.

25. The method of claim 23, wherein at least one aza substituent on a mannose unit is an amine or substituted amine that is obtained by reduction of an azide ($N_3$) substituent.

26. The method of claim 25, wherein the amine or substituted amine is at position 2 on a mannose unit.

27. The method of claim 25, wherein Z or the spacer moiety at the anomeric center comprises an amine-substituted alkoxy group.

28. The method of claim 23, further comprising linking the second mannose unit to an additional saccharide by forming a bond between the oxygen of $OR^6$ in formula (1) and the additional saccharide.

29. The method of claim 28, wherein the additional saccharide comprises at least one mannose unit.

30. The method of claim 29, wherein the additional saccharide is linked to the second mannose unit through a 1,6-alpha linkage.

31. The method of claim 28, wherein R6 is H or Ac and the anomeric center of each mannose unit present is in the alpha configuration.

32. A method for synthesizing an oligosaccharide of alpha-linked mannose units, said method comprising:
   combining a mannose unit comprising formula (2), wherein $R^6$ is C1-C6 acyl or H, and $R^1$, $R^3$, $R^4$, Az and Z are as defined in claim 15;

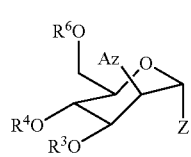

(2)

with an elongating monomer of formula (3), wherein $R^x$ represents a C1-C6 acyl group and M represents H or a cation;

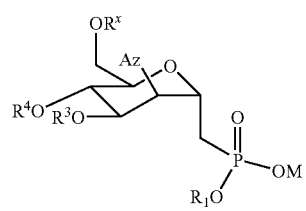

(3)

under Mitsunobu reaction conditions, whereby an oligosaccharide comprising at least two 2-aza substituted mannose units connected by a 1,6-alpha linkage is obtained.

33. The method of claim 32, wherein the Mitsunobu reaction conditions are maintained for a prolonged period of time, whereby an oligosaccharide of formula (4),

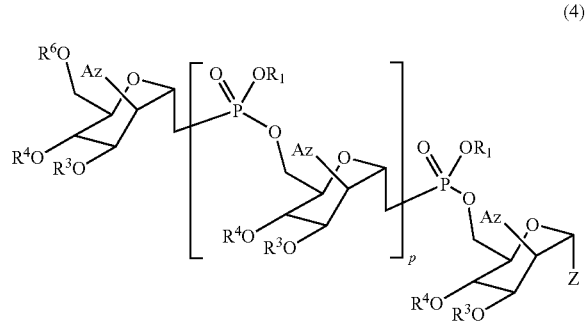

(4)

wherein p is an integer from 1 to 20, is obtained.

34. The method of claim 32 or 33, wherein each Az represents NHAc or $N_3$.

35. The method of claim 34, wherein p is 1-5.

36. The method of claim 34, wherein p is 2-10.

37. The method of claim 32, further comprising conjugating the oligosaccharide to a protein.

38. The method of claim 37, wherein the protein is an inactivated bacterial toxin selected from diphtheria toxoid, pertussis toxoid, E. coli LT, E. coli ST, Pseudomonas aeruginosa exotoxin (rEPA), or tetanus toxoid.

39. The method of claim 37, wherein the protein is CRM197.

40. A pharmaceutical composition comprising at least one oligosaccharide of claim 1, and at least one pharmaceutically acceptable excipient.

41. An immunogenic composition comprising at least one compound of claim 1.

42. A Meningitidis A vaccine comprising at least one compound of claim 1.

43. The Meningitidis A vaccine of claim 42, comprising an oligosaccharide conjugated to a protein.

* * * * *